(12) United States Patent
Koswara et al.

US010766014B2

(10) Patent No.: US 10,766,014 B2
(45) Date of Patent: Sep. 8, 2020

(54) SYSTEMS WITH ANTI-FOULING CONTROL AND METHODS FOR CONTROLLING FOULING WITHIN A CHANNEL OF A PLUG FLOW CRYSTALLIZER

(71) Applicant: Purdue Research Foundation, West Lafayette, IN (US)

(72) Inventors: Andy Koswara, West Lafayette, IN (US); Zoltan Kalman Nagy, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 284 days.

(21) Appl. No.: 15/496,355

(22) Filed: Apr. 25, 2017

(65) Prior Publication Data

US 2017/0312795 A1   Nov. 2, 2017

Related U.S. Application Data

(60) Provisional application No. 62/329,289, filed on Apr. 29, 2016.

(51) Int. Cl.
*C30B 29/54* (2006.01)
*B01J 19/00* (2006.01)
(Continued)

(52) U.S. Cl.
CPC ........ *B01J 19/0013* (2013.01); *B01D 9/0013* (2013.01); *B01D 9/0036* (2013.01); *B01D 9/0054* (2013.01); *B01D 9/0059* (2013.01); *B01D 9/0063* (2013.01); *B08B 7/0064* (2013.01); *B08B 17/00* (2013.01); *C07C 227/42* (2013.01); *C07C 231/24* (2013.01); *C30B 7/08* (2013.01); *C30B 29/54* (2013.01); *B01D 9/0072* (2013.01); *B01D 9/0077* (2013.01)

(58) Field of Classification Search
CPC .............. C30B 29/54; C30B 7/08; C30B 7/00
See application file for complete search history.

(56) References Cited

PUBLICATIONS

Alvarez and Myerson, "Continuous plug flow crystallization of pharmaceutical compounds," Crystal Growth & Design, 10(5), 2219-2228, (2010).

(Continued)

*Primary Examiner* — Robert M Kunemund
(74) *Attorney, Agent, or Firm* — Brown Rudnick LLP; Adam M. Schoen

(57) ABSTRACT

The invention generally relates to systems with anti-fouling control and methods for controlling fouling within a channel of a plug flow crystallizer. In certain aspects, the invention provides a system that includes a plug flow crystallizer having a channel, one or more heating/cooling elements, each operably associated with a different segment of the channel, and a controller. The controller is operably coupled to the one or more heating/cooling elements and configured to implement a temperature profile within the channel of the plug flow crystallizer that grows crystals in a plug of fluid that flows through a first segment of the channel and dissolves encrust in a second segment of the channel while having minimal impact on crystal growth in the plug of fluid in the second segment of the channel. In certain embodiments, these segments may be cyclically alternated, in that the segment in which crystal grows in one cycle becomes the segment in which crystal dissolves in the next cycle and vice versa, to realize a fully continuous crystallization process.

20 Claims, 38 Drawing Sheets

(51) Int. Cl.
    *C07C 227/42*     (2006.01)
    *C07C 231/24*     (2006.01)
    *B08B 7/00*     (2006.01)
    *B08B 17/00*     (2006.01)
    *C30B 7/08*     (2006.01)
    *B01D 9/00*     (2006.01)

(56) References Cited

PUBLICATIONS

Atencia, et al., "The microfluidic palette: a diffusive gradient generator with spatio-temporal control," Lab on a Chip, 9(18), 2707-2714, (2009).
Baba, et al., "Giant improvement of timedelayed feedback control by spatio-temporal filtering." Physical review letters, 89(7), 074101, (2002).
Biondi, et al., "Controlled drug delivery in tissue engineering," Advanced Drug Delivery Reviews, 60(2), 229-242, (2008).
Bohnet, Fouling of heat transfer surfaces Chemical engineering & technology, 10(1), 113-125, (1987).
Brahim, et al., "Numerical simulation of the fouling process," International Journal of Thermal Sciences, 42(3), 323-334, (2003).
Chen, et al., "Spatio-temporal vegf and pdgf delivery patterns blood vessel formation and maturation," Pharmaceutical research, 24(2), 258-264, (2007).
Gunawan, et al., "High resolution algorithms for multidimensional population balance equations," AIChE Journal, 50(11), 2738-2749, (2004).
Ji and Yang, "Real-time eye, gaze, and face pose tracking for monitoring driver vigilance," Real-Time Imaging, 8(5), 357-377, (2002).
Kuczenski, et al., "Pressure-driven spatiotemporal control of the laminar flow interface in a microfluidic network," Lab on a Chip, 7(5), 647-649, (2007).
Lawton, et al., "Continuous crystallization of pharmaceuticals using a continuous oscillatory baffled crystallizer," Organic Process Research & Development, 13(6), 1357-1363, (2009).
Lin, et al., "Generation of dynamic temporal and spatial concentration gradients using microfluidic devices," Lab on a Chip, 4(3), 164-167, (2004).
Majumder and Nagy, "Fines removal in a continuous plug flow crystallizer by optimal spatial temperature profiles with controlled dissolution," AIChE Journal, 59(12), 4582-4594, (2013).
Nagy and Braatz, "Advances and new directions in crystallization control," Annual review of chemical and biomolecular engineering, 3, 55-75, (2012).
Pouyssegur, et al., "Fidelity and spatio-temporal control in map kinase (erks) signalling," Biochemical pharmacology, 64(5), 755-763, (2002).
Ridder, et al., Pop-ulation balance model-based multiobjective optimiza-tion of a multisegment multiaddition (msma) continuous plug-flow antisolvent crystallizer. Industrial & Engineer-ing Chemistry Research, 53(11), 4387-4397, (2014).
Silva and Mooney, "Spatiotemporal con-trol of vascular endothelial growth factor delivery from injectable hydrogels enhances angiogenesis," Journal of Thrombosis and Haemostasis, 5(3), 590-598, (2007).
Simmendinger, et al., "Con-trolling complex temporal and spatio-temporal dynam-ics in semiconductor lasers," Chaos Solitons and Fractals, 10(4), 851-864, (1999).
Utomo, et al., "Tem-poral, spatial, and cell type-specific control of cre- mediated dna recombination in transgenic mice," Nature biotechnology, 17(11), 1091-1096, (1999).
Vendel and Rasmuson, "Mechanisms of initiation of incrustation," AIChE Journal, 43(5), 1300-1308, (1997).

SYSTEMS WITH ANTI-FOULING CONTROL AND METHODS FOR CONTROLLING FOULING WITHIN A CHANNEL OF A PLUG FLOW CRYSTALLIZER

RELATED APPLICATION

The present application claims the benefit of and priority to U.S. provisional application Ser. No. 62/329,289, filed Apr. 29, 2016, the content of which is incorporated by reference herein in its entirety.

GOVERNMENT SUPPORT

This invention was made with government support under Contract No. 5U01FD004275 awarded by the U.S. Food and Drug Administration. The government has certain rights in the invention.

FIELD OF THE INVENTION

The invention generally relates to systems with anti-fouling control and methods for controlling fouling within a channel of a plug flow crystallizer.

BACKGROUND

Given the tremendous advances of pharmaceutical innovations in the area of drug development and discovery, the advancement of pharmaceutical manufacturing science has lagged in comparison. While the cost of drug discovery dominates the overall spending in pharmaceutical research, the cost of process development and manufacturing has reached an all-time high, consequently garnering both regulatory and industrial support for a shift from batch to continuous manufacturing. The advantages for continuous manufacturing include improved process integration, smaller equipment and facilities, and real-time process monitoring and control. These engineering improvements may lead to regulatory and economic benefits such as better and more consistent product quality, lower capital and operating cost, and increased safety, which then translate to more affordable and efficacious drug products. As in any chemical processes, the successful implementation of a continuous process is largely dependent on its design, scalability and robustness.

Plug-flow crystallization (PFC) has shown considerable promise in these regards due to its fast start-up dynamics, excellent mixing, and flexible temperature and (anti-)solvent control when compared with other types of continuous crystallizers, such as mixed-product mixed suspension reactors (MSPR). In addition, more advanced control of crystal quality using plug-flow crystallization has recently been demonstrated.

Nevertheless, plug-flow crystallization is plagued with fouling or encrustation, which prevents it from being the ideal continuous crystallizer. Encrustation is a phenomena by which uncontrolled crystallization takes place at the reactor surface, resulting in a number of operational issues, such as flow blockage, reduced heat transfer due to increased thermal resistance, and reduced supersaturation. These events result in limited continuous operation and reduced crystal quality and yield.

SUMMARY

The invention provides model-based anti-fouling control (AFC) via spatial and temporal heating and cooling cycles, in which a temperature profile across different segments of a plug flow crystallizer is determined such that encrust is periodically dissolved with minimal impact on product quality and yield. Aspects of the invention are based on a recognition that due to presence of a boundary layer between encrust and a channel of a plug flow crystallizer, there exists a temperature gradient between the two domains. Consequently, during cooling, a film temperature is lower than that of the channel, while during heating it is higher. Accordingly, a temperature profile is possible due to the difference in the film and channel temperature and, therefore, the different degree of supersaturation driving force for crystal and encrust dissolution. The invention takes advantage of that recognition and implements a temperature profile that can grow crystals in one segment of a channel of a plug flow crystallizer while dissolving encrust in another segment of the channel of the plug flow crystallizer while having minimal or no impact on crystal growth in that segment of the channel of the plug flow crystallizer. To this end, the invention provides a multi-segment plug flow crystallizer that may be divided into at least two parts, which periodically cycle between cooling and heating regions. In the cooling segment, the temperature is optimized such that crystal growth is maximized, while in the heating segment, encrust dissolution is enforced but with crystal dissolution minimized.

The systems and methods of the invention are readily implementable with feedback sensors to achieve desired control performance and product quality without cyclical calculation of an optimal control profile or knowledge of initial conditions at the start of each cycle.

Certain aspects of the invention provide systems with anti-fouling control that include a plug flow crystallizer having a channel, one or more heating/cooling elements, each operably associated with a different segment of the channel, and a controller. The controller is operably coupled to the one or more heating/cooling elements and configured to implement a temperature profile within the channel of the plug flow crystallizer that grows crystals in a plug of fluid that flows through a first segment of the channel and dissolves encrust in a second segment of the channel while having minimal impact on crystal growth in the plug of fluid in the second segment of the channel. In certain embodiments, these segments may be cyclically alternated, in that the segment in which crystal grows in one cycle becomes the segment in which crystal dissolves in the next cycle and vice versa, to realize a fully continuous crystallization process. The controller may be further configured to calculate the temperature profile based on encrust kinetics and crystal growth kinetics for a particular reaction.

Systems of the invention may include one or more sensors operably coupled to the system. For example, a first sensor may determine a period of output stream collection for as long as flow is within a predetermined product quality range. In such embodiments, the first sensor operably communicates to the controller, which manipulates a valve based on data received from the first sensor, to control collection of the one or more plugs of fluid. In another example, a second sensor monitors encrust within the channel. The second sensor may operably communicate to the controller, which manipulates the temperature within the channel, via the one or more heating/cooling elements, based on data received from the second sensor.

Other aspects of the invention provide methods for controlling fouling within a channel of a plug flow crystallizer. The methods may involve flowing one or more plugs of fluid through a channel of a plug flow crystallizer, and implementing, via a controller operably coupled to the plug flow crystallizer, a temperature profile within the channel of the plug flow crystallizer that grows crystals in the one or more plugs of fluid that are flowing through a first segment of the channel and dissolves encrust in a second segment of the channel while having minimal impact on crystal growth in the plugs of fluid in the second segment of the channel. Methods of the invention may further involve calculating, using an algorithm and via the controller, the temperature profile based on encrust kinetics and crystal growth kinetics for a particular crystallization reaction. Methods of the invention may additionally involve monitoring conditions within the channel via one or more sensors operably coupled to the controller, such as discussed above.

In the systems and methods of the invention, the segments can be symmetrical or asymmetrical and the encrust kinetics and crystal growth kinetics for a particular reaction will dictate the length of each segment and the configuration of the segments. In certain embodiments, the first segment of the channel has a same length as the second segment of the channel. In such embodiments, the temperature profile in the first segment may be configured for cooling the one or more plugs of fluid that flow in the first segment to thereby cause crystal growth. In such embodiments, the temperature profile in the second segment may be configured for heating the one or more plugs of fluid that flow in the second segment to thereby cause encrust dissolution while having minimal impact on crystal growth in the one or more plugs of fluid in the second segment of the channel.

BRIEF DESCRIPTION OF THE DRAWINGS

FIG. 8A shows crystal size distribution (CSD). FIG. 8B shows temperature profile. FIG. 8C shows crystal growth. FIG. 8D shows encrustation. Both CSD and temperature profile were taken at the 12th RT. FIGS. 8A-D show how the dynamics are initially dominated with encrust formation but later followed by crystal formation.

FIG. 13A corresponds to the CSD evolution. FIG. 13B shows temperature profiles. FIG. 13C shows the crystal growth rate. FIG. 13D shows the encrust formation and dissolution.

DETAILED DESCRIPTION

Figure 1:
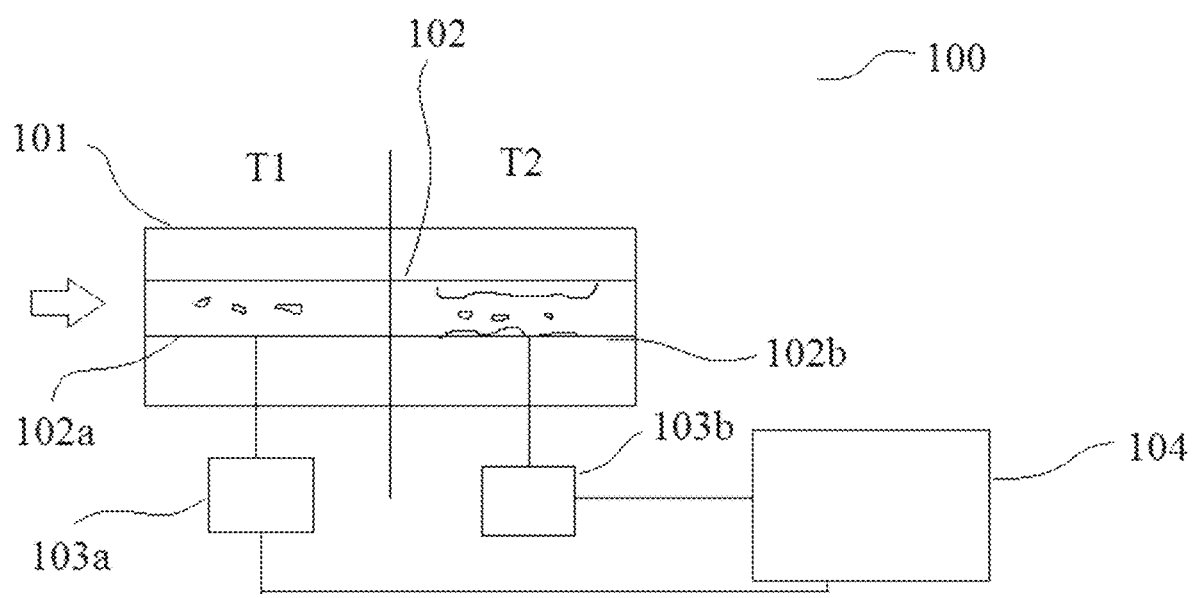
FIG. 1 is a schematic of an embodiment of a system of the invention.

The invention generally relates to systems with anti-fouling control and methods for controlling fouling within a channel of a plug flow crystallizer. FIG. 1 show an exemplary embodiment of a system 100 of the invention. System 100 generally includes a plug flow crystallizer 101 having a channel 102, one or more heating/cooling elements (e.g., 103a and 103b), each operably associated with a different segment of the channel 102, and a controller 104. The controller 104 is operably coupled to the one or more heating/cooling elements (in this case, element 103a and element 103b) and configured to implement a temperature profile within the channel 102 of the plug flow crystallizer 101 that grows crystals in a plug of fluid that flows through a first segment 102a of the channel 102 (T1 zone) and dissolves encrust in a second segment 102b of the channel 102 while having minimal impact on crystal growth in the plug of fluid in the second segment 102b of the channel 102 (T2 zone). The vertical line denotes the split between the two channel segments into the first segment 102a and the second segment 102b. Flow direction is shown by the block arrow.

The skilled artisan will appreciate that the design in FIG. 1 is exemplary and that other designs are within the scope of the invention. For example, FIG. 1 shows the channel bisected into two symmetrical segments. The channel can be sectioned to have more than two segments, e.g., four segments, six segments, eight segments, etc. Additionally, the segments do not have to be symmetrical. For example, in other embodiments, the segments are asymmetrical segments. Asymmetry may be desired when the kinetics of crystal growth and encrust dissolution are different from each other. Symmetrical segments work best when the kinetics of crystal growth and encrust dissolution are the same. The skilled artisan will appreciate that the encrust kinetics and crystal growth kinetics for a particular reaction will dictate the length of each segment and the configuration of the segments.

Figure 2:
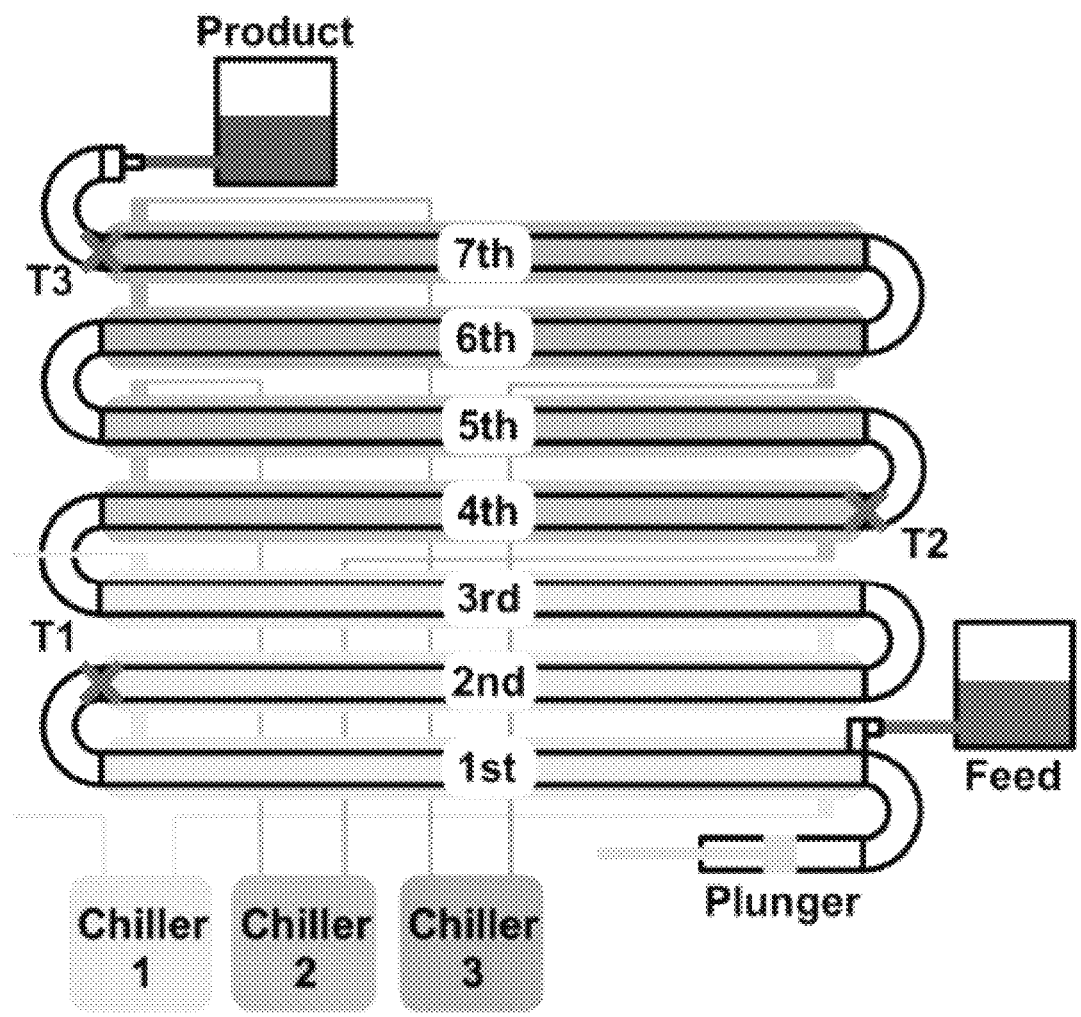
FIG. 2 is a schematic of another embodiment of a system of the invention.

The embodiment shown in FIG. 1 illustrated with a plug flow crystallizer having only a linear channel divided into two symmetrical segments. Other embodiments are within the scope of the invention. For example, FIG. 2 illustrates an embodiment using a serpentine channel within a plug flow crystallizer. In this embodiment, temperature zone T1 includes multiple serpentine sections of the channel and temperature zone T2 multiple serpentine sections of the channel. In this embodiment, T1 and T2 are symmetrical. T3 is the desired temperature for the product. Any number of serpentine sections can be coupled together and the number used in any particular reaction will depend on the desired crystal product yield.

In other embodiments, each section of the serpentine can be divided into two segments of T1 and T2. In such an embodiment, the plugs of fluid alternative between T1 and T2 at each section of the serpentine.

The different components of the system are described further herein.

Plug Flow Crystallizer

Plug flow crystallizers are described for example in each of Alvarez et al. (Cryst. Growth Des., 2010, 10 (5), pp 2219-2228), Neugebauer et al. (Cryst. Growth Des., 2015, 15 (3), pp 1089-1095), Kwon et al. (Chemical Engineering Science, Volume 119, 8 Nov. 2014, Pages 30-39), and Alvarez et al. (U.S. Pat. No. 8,216,363), the content of each of which is incorporated by reference herein in its entirety.

An exemplary plug flow crystallizer used to carry out the continuous crystallization process generally includes a plurality of continuous plug flow reactors connected in series, each of which may include a static mixer in order to reduce or eliminate axial mixing. The feed solution, including a solution of the compound of interest and a solvent, and an antisolvent are introduced to the first reactor module, which initiates formation of crystals of the compound of interest, and the resulting slurry comprising the feed solution, the antisolvent, and the crystals flows sequentially from one continuous plug flow reactor to the next. Such a series of plug flow reactors increases the flexibility of the process. In addition, temperature can be varied, for example lowered, through a temperature control jacket around the reactors, as cooling the solvent mixture (the mixture of the feed solution and the antisolvent) allows additional supersaturation control and increased yield.

In certain embodiments, multistage addition of an antisolvent to a continuous plug flow system is contemplated. Embodiments further include a system for carrying out the crystallization process disclosed above.

In certain embodiments, a first solution is a feed solution comprising a preferred compound in a suitable solvent or combination of solvents, and a second solution is an antisolvent capable of initiating the preferred compound's precipitation from the first solution. The antisolvent is chosen based on a relatively low solubility of the solute in the antisolvent. The first solution preferably can be unsaturated, undersaturated, or supersaturated. As is known in the crystallization art, the solvent and antisolvent are selected to be miscible so they can mix and form a solvent mixture in which the solubility is much less than the solute in the original solvent.

Compounds of interest preferably include organic compounds and active pharmaceutical ingredients. For example, paracetamol, ibuprofen, theophylline, carbamazepine, sulfathiazole, itraconazole, and other related compounds are presented as models as these compounds are of great interest to the medical and research communities. The example pharmaceutical compounds chosen are commercially important, have more than one polymorph, and/or will form an amorphous solid under high supersaturation.

Amino acids are also presented as compounds of interest, as (i) amino acids are relatively easy to grow in aqueous and alcohol solutions; (ii) almost all the amino acids have more than one crystal structure (or polymorph); (iii) there is an extensive background and information on the crystallization of each amino acids; and (iv) at high supersaturations, the nanometer and micron sized amino acid crystals are amorphous or semi-crystalline.

Solvents or antisolvents may include organic and inorganic solvents. The solvent, if used, should be compatible with the compound of interest in that the compound of interest must be soluble in the solvent. Further, the compound/solvent solution should be capable of supersaturation. Although the preferred solvent is water, other suitable solvents include, but are not limited to, organic, inorganic, ionic liquids, and supercritical solvents. Once a compound of interest is selected for producing crystals, the appropriate solvent is selected. Those of ordinary skill in the art can determine the appropriate solvent for a selected compound of interest without undue experimentation.

Other preferred solvents include alcohols, ethyl acetate, halogenated solvents, acids, bases, acetonitrile, hexanes, ethers, and water. Suitable illustrative examples of solvents and antisolvents include, but are not limited to, ethanol, methanol, ethyl acetate, methylene chloride, acetonitrile, acetic acid, hexane, ether, and water. Alternatively, the antisolvent can contain a suitable reactant compound that reacts with the compound to be crystallized in the feed solution. Given the compound to be crystallized by a reactant crystallization process, one of ordinary skill in the art also would be able to select suitable reactant compounds to initiate the crystallization process.

In certain embodiments, it is desirable to control the residence time of the feed solution in the one or more reactors for the optimal growth of crystals. Generally, the residence time for growing crystals preferably is on the order of a few minutes to a few days, depending on the growth rate of the compound, and more preferably is between about 5 minutes to about 120 minutes. Residence time is defined as the average time for processing of the feed solution in one reactor volume measured at specified conditions. It is also known as space time denoted by the symbol $\tau$. Residence time is calculated as the volume divided by the volumetric flow rate. Accordingly, if the dimensional volume of a reactor increases, while keeping the volumetric flow rate of the feed solution constant, the residence time of the feed solution in the reactor would increase. Conversely, if the volumetric flow rate were to increase, while keeping the total dimensional volume constant, the residence time would decrease.

In addition, optimal crystal size also depends on the type of flow of the feed solution within the crystallizer. The Reynold's number $R_e$ is a dimensionless unit used to identify and predict different flow regimes, such as laminar or turbulent flow, within the crystallizer. Laminar flow occurs at low Reynolds numbers, where viscous forces are dominant. Laminar flow occurs generally at $R_e$<50 and may be characterized as a smooth, constant, fluid motion. On the other hand, turbulent flow is a direct result of a high Reynold's number and primarily dominated by inertial forces. Turbulent flow occurs generally at $R_e$>200 and tends to produce random eddies, vortices and other flow fluctuations.

According to certain embodiments of the present invention, crystals can be grown within a temperature range of between about −25° C. to 150° C., but preferably are grown within a temperature range of 0° C. to 100° C., and more preferably between about 5° C. and about 40° C. One factor in choosing the temperature for the crystal growth is the temperature at which the compound of interest will precipitate out of the supersaturated solution. Other factors are primarily attributed to the physical and chemical characteristics of the compound of interest. Additionally, the solvent mixture (alternatively referred to as the crystal slurry) can be cooled as it progresses through the stages to provide additional supersaturation. Cooling can be accomplished through the jacket pipe and each stage can be at a lower temperature than the previous stage.

Figure 3:
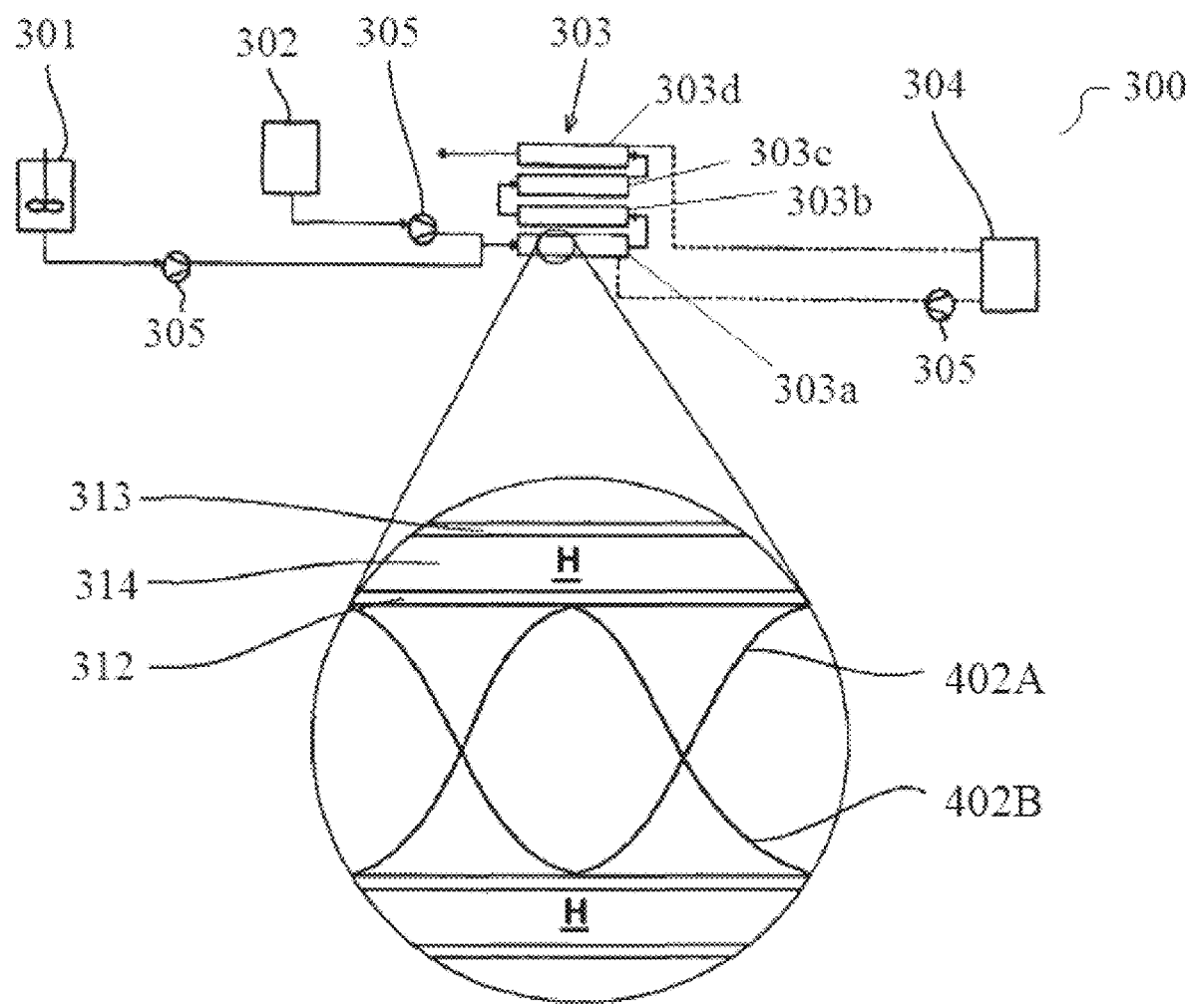
FIG. 3 illustrates an embodiment of a plug flow crystallizer.

FIG. 3 illustrates an embodiment of a plug flow crystallizer A solution of the first (feed) solution (i.e., an API or organic compound) is initially contained within a storage tank 301, and the second (antisolvent) solution is initially contained within a separate storage tank 302, such as volumetric flasks. The feed solution and the antisolvent are fed into a reactor 303, which preferably is a jacketed reactor comprising an interior core reactor 312 and a surrounding jacket pipe 313, as disclosed in more detail below. As disclosed in more detail below, the feed solution and the antisolvent solution are respectively injected into the first reactor module 303a of the core reactor 312 to initiate the crystallization reaction, and the crystal slurry is removed from the last of the reactor modules 303, in this case the fourth reactor module 303d, for drying and further processing.

The continuous plug flow system 300 comprises a crystallizer (reactor) 303 with multiple reactor modules 303 a-d. Four reactor modules 303 are disclosed in the illustrative embodiment, but it is possible to use more or fewer reactor modules 303. Each reactor 303 comprises a core reactor 312 where crystallization occurs. The illustrative core reactor 312 for proving the concept of this invention is tubular and can carry up to 76 cm$^3$ of solution. This illustrative core reactor 312 is 600 mm long and has an internal diameter of 12.7 mm. The reactor modules 303a-d are set up in series such that the solution and antisolvent flow consecutively through the reactor modules 303a-d. Moreover, reactor modules 303a-d can be added or omitted as necessary in order to obtain the desired crystal size distribution.

A sleeve or jacket pipe 313 preferably surrounds the core reactor 312, which, in the illustrative embodiment, creates a sleeve and tube reactor of concentric tubes, with the reactor core 312 being the inner tube and the jacket pipe being the outer tube. The illustrative jacket pipe 313 is 600 mm long and has an internal diameter of 35 mm. The jacket pipe 313 has a greater diameter than the core reactor 312 so as to leave a annular manifold space 314 between the core reactor 312 and the jacket pipe 313. Heat exchanging fluid H is circulated in the jacket pipe 313, specifically in the annular manifold space 314, in a known manner in order to regulate the temperature inside the core reactor 312.

Glass is a preferred material for fabricating the core reactor 312 and jacket pipe 313 so that the experiment could be visible (e.g., optically clear) for detecting abnormal patterns in the flow. Other materials are suitable and can be selected by those of ordinary skill in the art without undue experimentation based on the desired or necessary heat transfer characteristics of the fabricating materials.

The preferred temperature range for operation of the core reactors 312 is from about −25° C. to about 150° C. The range is controlled with a specificity of +−0.1° C. using a waterbath temperature controller (e.g., a NESLAB RTE Refrigerated Bath/Circulator is suitable for controlling the temperature at which crystallization is carried out). The controller 304 has a processor in order to carry out specific processes such as increasing or decreasing temperature and flow rate for the pumps 305. Preferred pumps 305 are peristaltic pumps (e.g., Masterflex L/S series, variable speed from Cole Parmer) with maximum feed rate of 1700 ml/min. Although FIG. 3 displays three pumps 305, one of ordinary skill may increase or decrease the number of pumps in order to obtain the desired flow rate.

Figure 4:
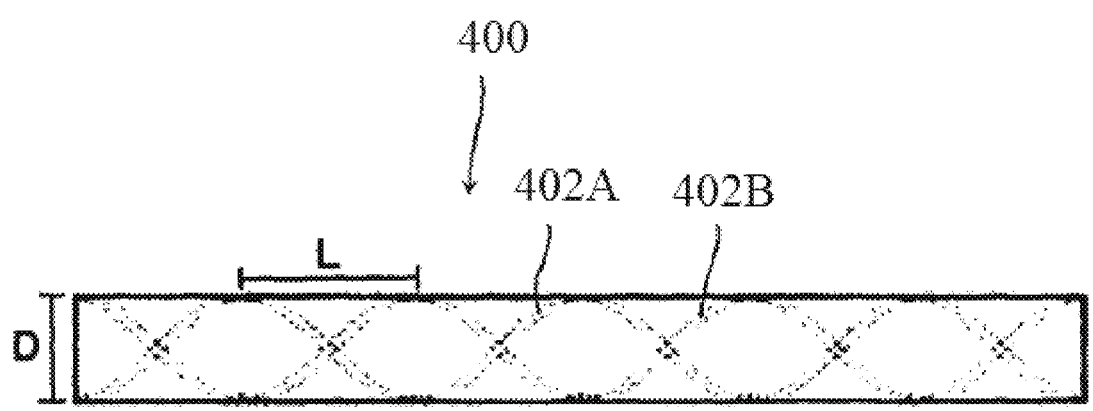
FIG. 4 illustrates a suitable static mixer.

FIG. 4 illustrates a suitable static mixer 400 that optionally operates within or optionally forms a part of the crystallization reactor 303 (e.g., a Kenics brand static mixer). Generally, a static mixer is a stationary obstacle placed in a tubular reactor in order to promote mixing and can be seen as the equivalent of the stirrer in a stirred tank reactor. It has the advantage that it has no moving parts and it extracts the energy required for mixing from the flow in the form of an increase in pressure drop. Furthermore, the maintenance cost and operating cost of static mixers are lower than conventional stirrers and a static mixer requires less space.

Static mixers consist of a series of elements of alternating clockwise 402A and counterclockwise 402B twist arranged axially within a tube (i.e., core reactor 312) to promote mixing. Static mixers cause feed solutions to approach plug flow when the number of mixing elements is increased. Operation of the present invention in a plug flow system is desirable because it leads to a narrow particle size distribution. The basic principle of these static mixers is to split, stretch and recombine the fluid in order to achieve mixing. In particular, the preferred static mixer includes a series of mixing elements, each consisting of a short helical length of approximately 1.5 times the tube's diameter. The helices have clockwise and counterclockwise rotations at an angle of 180°. The two converging helixes are placed at an angle of 90° with respect to each other.

At higher Reynolds numbers, the static mixer is comparable to a rotating plate that suddenly changes its rotation direction. At the suction side of the mixing element vortices appear, which are similar to vortices that appear when a plate is rotated. Furthermore, due to the sudden change in flow direction at the junction of two mixing elements, a large vortical structure appears at the center of the mixing element. These vortical structures play a significant role in the mixing efficiency. Residence time distribution can be evaluated under different flow conditions by means of tracer particles to determine if a desired level of mixing is being achieved.

Channels

The plug flow crystallizer can include one or more channels that form the boundary for a fluid. A channel, as used herein, refers to a feature on or in the plug flow crystallizer that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

The dimensions of the channel may be chosen such that fluid is able to freely flow through the channel. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, etc.

The plug flow crystallizer can also include one or more fluid channels to inject or remove fluid into another channel within the plug flow crystallizer. The channels of the plug flow crystallizer can be of any geometry as described. However, the channels of the plug flow crystallizer can comprise a specific geometry such that the contents of the channel are manipulated, e.g., sorted, mixed, prevent clogging, etc.

Driving Forces

The system can use pressure driven flow control, e.g., utilizing valves and pumps, to manipulate the flow of reagents in one or more directions and/or into one or more channels of a system. However, other methods may also be used, alone or in combination with pumps and valves, such as syringe pumps, electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155). The content of each reference is incorporated by reference herein in its entirety.

Positive displacement pressure driven flow is an exemplary way of controlling fluid flow as well as dielectrophoresis. Multiple different driving forces can be used within the system.

The pressure at the inlet of the system can also be regulated by adjusting the pressure on the channel coupled to the inlet. For example, a valve may be placed at or coincident to the inlet to control the flow of solution into the inlet channel of the plug flow crystallizer, thereby controlling the flow within the plug flow crystallizer. Flow may also depend on channel diameter, the viscosity of the fluids, and shear pressure.

Reservoir/Well

A systems of the invention can include a sample solution reservoir or well or other apparatus for introducing a fluid or reagent to the system, via an inlet of one of the system, which is typically in fluid communication with a channel within the plug flow crystallizer. Reservoirs and wells used for loading one or more reagents onto the system of the present invention, include but are not limited to, chambers within the system. A reservoir may facilitate introduction of reagents into the system.

Heating and Cooling Elements

Heating and cooling elements are discussed in connection with the plug flow crystallizer. Other exemplary heating/cooling elements are discussed here that are also suitable with the systems and methods of the invention. In certain embodiments, the system will include one or more heating elements. An exemplary heating element is a Peltier device. Peltier devices are commercially available, for example, from Custom Thermoelectric (Bishopville Md.). Peltier devices, also known as thermoelectric (TE) modules, are small solid-state devices that function as heat pumps. Generally, the device is formed by two ceramic plates with an array of small Bismuth Telluride cubes in between. Application of a DC current moves heat from one side of the device to the other, thus producing a temperature gradient in which a first side to which the device is connected is cooled and a second side to which the device is connected is heated. Changing the polarity across the surfaces, reverses the heating/cooling. To increase the efficiency of the Peltier module, a thermal interface material can be placed between the Peltier module and the surface. Exemplary thermal interface materials include silicone-based greases (e.g., zinc oxide silicone), elastomeric pads, thermally conductive tapes, and thermally conductive adhesives.

Peltier devices require that the heat generated from the hot side be removed from the device. In certain embodiments, the peltier device generally includes a heat sink couple to a fan to remove heat from the surface of the device.

In certain embodiments, the system will include one or more cooling elements. In certain embodiments, a single unit can have heating and cooling functions and therefore the heating and cooling elements are combined into a single unit. An exemplary cooling device is a chiller plate that is operably coupled to the plug flow crystallizer. The chiller plate cools the content of the channels.

In certain embodiments, the system including a heating and/or cooling element also includes a temperature sensor and/or a temperature controller. The temperature controller and sensor are operably coupled to each other and the sensor is operably coupled to the heating/cooling device and the system controller. For example, the peltier device includes a polarity controller. Any polarity controller known in the art may be used, such as an H-bridge controller (commercially available from Texas Instruments, manufacturer part number DRV8828PWP). The polarity controller is coupled to the temperature sensor. The polarity controller changes polarity of the peltier device in response to a signal sent from the temperature sensor. Changing the polarity changes the heating/cooling of the surface. For example, if the peltier device is configured such that the top portion of the surface is heating and the bottom portion is cooling, then changing the polarity will cause the top portion to cool and the bottom portion to heat.

The entire module can be controlled by any known commercially available controller, such as a programmable logic controller (PLC) or a computer running an operating system such as Windows. Particularly, the temperature sensor sends signals to the logical controller, which then takes the appropriate action (e.g., heating or cooling), based on the signal received from the temperature sensor.

The skilled artisan will recognize that other heating/cooling elements can be used with system, such as those described in Miralles et al. (Diagnostics (Basel). 2013 March; 3(1): 33-67), the content of which is incorporated by reference herein in its entirety.

As already discussed above, the plug flow crystallizer can be configured to have two or more temperature zones, e.g., two zones, four zone, six zones, eight zones, ten zones, etc. The channel or channels within the plug flow crystallizer can be configured to facilitate flow into the one or more temperature zones. For example, a serpentine configuration may be useful (as shown in FIG. 2).

Controller

Figure 5:
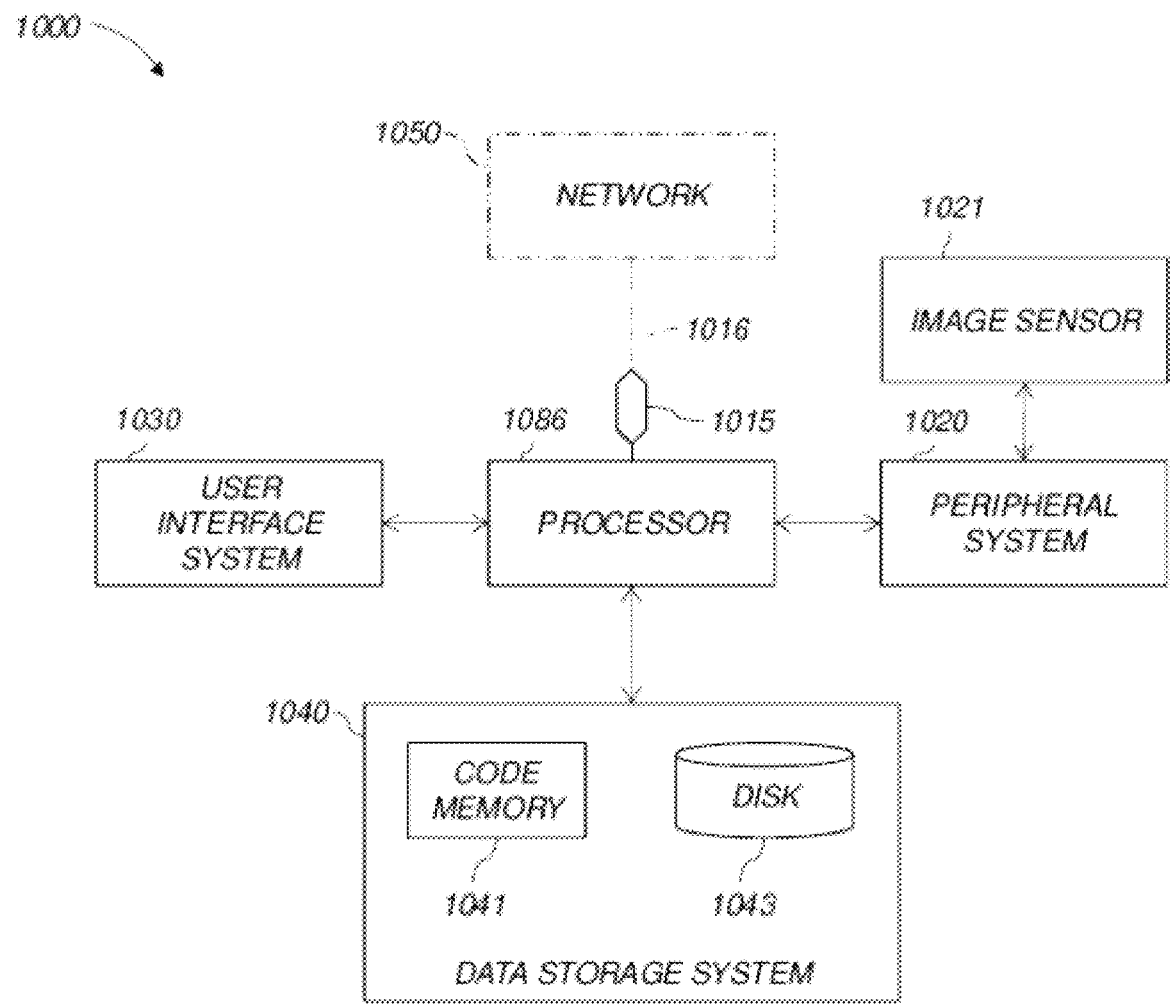
FIG. 5 is a high-level diagram showing the components of an exemplary data-processing system.

FIG. 5 is a high-level diagram showing the components of an exemplary data-processing system 1000 for analyzing data and performing other analyses described herein, and related components. The system includes a processor 1086, a peripheral system 1020 (chemical production system), a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The data described above may be obtained using detector 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 which in one embodiment may be capable of real-time calculations (and in an alternative embodiment configured to perform calculations on a non-real-time basis and store the results of calculations for use later) can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (e.g., a tablet) connected, e.g., via a network or a null-modem cable, or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), Universal Serial Bus (USB) interface memory device, erasable programmable read-only memories (EPROM, EEPROM, or Flash), remotely accessible hard drives, and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors) to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

As illustrated in FIG. 5, the processor controls all aspects of the system. Data is sent and received by the processor. The system can be configured to have a feedback loop architecture so that data received by the processor (e.g., by one or more sensors) can be acted on by the user (through manual adjustment via the processor) or processor (in automated embodiments) to correct or adjust one or more operating parameters of the system.

Valves

Any of the channels in the system can be equipped with one or more valves for flow control. Exemplary valves are rotary valves, but the skilled artisan will recognize that other valves can be used with systems of the invention, such as those described for example in Lee at al. (U.S. patent application publication number 2007/0141593), Neukermans et al. (U.S. Pat. No. 6,068,751), or Unger et al. (Science Vol 288 7 Apr. 2000), the content of each of which is incorporated by reference herein in its entirety. The valves are operably coupled to the central processor, which controls operation of the valves.

Monitoring within the System

As discussed further in the examples, the system of the present invention can also include one or more detection elements (apparatuses, devices, components, sensors) that assist in monitoring processing occurring within the system. One or more detection elements (e.g., sensors) are generally associated with the channels of the system, where reagents or chemical products are to be detected, identified, measured or interrogated on the basis of at least one characteristic. The reagents or chemical products can be examined one at a time or in bulk, and the characteristic is detected or measured.

Various analytical devices can be used to measure the type, size, and CSD of crystals produced as well as the characteristics of the solution in which the crystals are in, such as concentration. For example, an ultraviolet spectrophotometer (e.g., model GENESYS 20 from Thermo Spectronic with a wavelength range of about 325 to 1100 nm or a UV cell Fisher Scientific 14-385-918A 3 ml capacity) or an infrared spectrophotometer (e.g., model IdentifyIR from Smiths Detection Technology with a wavelength from about 4000 to 650 $cm^{-1}$) can be utilized for measuring the concentration of compounds, depending on the compounds, within the solution. The CSD of the solid product can be characterized with laser diffraction (e.g., Microtrac Standard Range Analyzer model SRA 150 from Leeds & Northrup, with measurement range from about 0.7 to 704 μm) or with focused beam reflectance measurement (FBRM) (e.g., Lasentec 5400 probe from Mettler Toledo, with a measurement range from about 785 nm to 100 μm), also depending on the compounds. The probe based FBRM technique allows for in situ particle analysis. The number of chord lengths (the product of the reflection time and the beam velocity) is measured during a time interval to yield a chord length distribution. The laser light diffraction instrument is able to produce a number distribution, area distribution, and volume distribution of the sample. The laser diffraction instrument assumes the measured crystals are spheres in order to calculate the CSD from the measured diffraction pattern. Another method of measurement includes raman spectroscopy probe (OCT-Prime 840-200 from Tornado Spectral Systems), which can characterize the type of crystal polymorph.

Other exemplary detector elements are optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement. However, other detection techniques can also be employed.

The term "determining," as used herein, generally refers to the analysis or measurement of a reagent or chemical product, for example, quantitatively or qualitatively, and/or the detection of the presence or absence of the reagent or chemical product. "Determining" may also refer to the analysis or measurement of an interaction between two or more reagents or a reagent with an intermediate of the chemical product, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements as described further herein.

A detection element is within, communicating or coincident with a portion of the channel at or downstream of the inlet. Precise boundaries for the detection element are not required.

In other embodiments, one or more sensors and/or processors may be positioned to be in sensing communication with the fluid within the channel. "Sensing communication," as used herein, means that the sensor may be positioned anywhere such that the fluid within the system (e.g., within a channel of the plug fluid crystallizer) may be sensed and/or determined in some fashion. For example, the sensor may be in sensing communication with the fluid such that the communication is fluidly, optically or visually, thermally, pneumatically, electronically, or the like. The sensor can be positioned proximate the fluid, for example, embedded within or integrally connected to a wall of a channel, or positioned separately from the system, but with physical, electrical, and/or optical communication with the system (e.g. one or more channels of the plug fluid crystallizer) so as to be able to sense and/or determine crystallization of one or more reagents, chemical product intermediates, and/or chemical products within the fluid or encrust within a channel. For example, a sensor may be free of any physical connection with a channel containing a fluid, but may be positioned so as to detect electromagnetic radiation arising from the fluid, such as infrared, ultraviolet, or visible light. The electromagnetic radiation may be produced by one or more reagents, chemical product intermediates, and/or chemical product within the fluid in such as a manner as to indicate one or more characteristics of the fluid, for example, through absorption, reflection, diffraction, refraction, fluorescence, phosphorescence, changes in polarity, phase changes, changes with respect to time, etc. As an example, a laser may be directed towards the fluid, and the fluorescence of the fluid may be determined. "Sensing communication," as used herein may also be direct or indirect. As an example, light from the fluid may be directed to a sensor, or directed first through a fiber optic system, a waveguide, etc., before being directed to a sensor.

Non-limiting examples of detection sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluid and/or the portion of the fluidic system containing the fluid. In some cases, the sensor may be connected to a processor, which in turn, cause an operation to be performed on the fluidic droplet, for example, by sorting the droplet.

Characteristics determinable with respect to the fluid and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, or pressure. In certain embodiments, one or more channels in the microfluidic modules include one or more pressure sensors.

A corresponding signal is then produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate completeness of a reaction. In response to the signal, data can be collected and/or a control system of sorting, if present, can be activated to divert fluid flow into one branch channel or another. The means of changing the flow path can be accomplished through mechanical, electrical, optical, or some other technique as described herein.

An exemplary detector/sensor is an optical detector, which may be coupled with a computer and/or other image processing or enhancement devices to process images or information produced by the optical detector using known techniques. There is no limit to the kind or number of characteristics that can be identified or measured using the techniques of the invention.

In certain embodiments, the detection element may include an apparatus to cause a crystallized reagent or chemical intermediate or chemical product to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection element. Where a laser is used, the laser can be set to scan across a set of detection modules from different analysis units. In addition, laser diodes or LED's may be microfabricated into the system. Alternatively, laser diodes or LED's may be incorporated into a separate element (i.e., a laser diode module) that is placed adjacent to the system such that the laser light from the diodes shines on the system.

An integrated semiconductor laser and/or an integrated photodiode detector can be included on the system, associated with one or more channels. This design provides the advantages of compactness and a shorter optical path for exciting and/or emitted radiation, thus minimizing distortion and losses. Fluorescence produced by a reporter, reagent, chemical intermediate, or chemical product, is excited using a laser beam.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Plug-flow crystallization (PFC) is a promising continuous pharmaceutical crystallization system. It is, however, prone to encrustation, a process by which uncontrolled crystallization takes place on the reactor surface. This phenomena results in operational issues such as flow blockage, increased thermal resistance, and reduced supersaturation, which in turn lead to limited continuous operation and reduced crystal quality and yield. The Examples herein introduce a model-based anti-fouling control (AFC) via spatial and temporal heating and cooling cycle. This work focuses on the open-loop implementation and its comparison with optimized PFC operation without AFC under two conditions: (1) maximization of crystal growth in the presence of encrustation and (2) minimization of encrustation while maintaining crystal growth. The Examples highlights the advantages and disadvantages of the AFC design. Additional Examples provide another embodiment of an AFC design with periodic and feedback control implementation accompanied with robustness and yield and productivity analysis.

Example 1: Population Balance Modeling with Encrustation Dynamics

The PFC-PBM dynamics is described as follows:

$$\frac{\partial}{\partial t}(A_f n) + \frac{\partial}{\partial z}(u_z A_f n) + \frac{\partial}{\partial L}(G A_f n) = 0, \quad (1)$$

Figure 6:
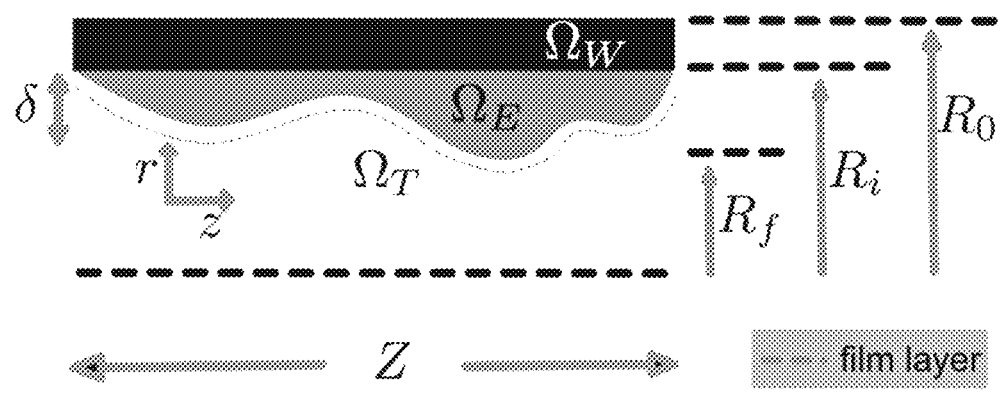
FIG. 6 shows domain schematics of encrustation-PBM-PFC dynamic model.

B.C.: $G(S)n(t, L, z)|_{L=0} = B(S)$, $n(t, L, z)|_{z=0} = n_{seed}(L)$,

Here, n is the crystal size distribution (CSD), $u_z$ is the slurry flow velocity, G is the crystal growth rate, B is the nucleation rate, n seed is the seed CSD, z is the reactor axis, L is the crystal size axis, and t is the time axis. $A_f(t, z) = \pi R_f^2(t, z)$ is the flow area within the tube which changes with time and along the reactor length due to encrustation. Majumder and Nagy have developed a model for encrustation in a PFC inspired from fouling kinetics commonly found in heat exchangers (FIG. 6). The encrustation dynamics can be summarized as follows:

$$\frac{d\delta}{dt} = k_E \frac{d\chi}{dt} = \frac{k_m}{\rho_E} \frac{dm}{dt} = \frac{k_m}{\rho_E}\left(\frac{dm_d}{dt} - \frac{dm_r}{dt}\right) \quad (2)$$

$$= \frac{k_m}{\rho_E}\left[\frac{1}{2}\frac{k_m}{k_R} + (C_b - C_{sat}) - \left(\frac{1}{4}\frac{k_m^2}{k_R^2} + \frac{k_m}{k_R}(C_b - C_{sat})\right)^{1/2}\right] -$$

$$\frac{\rho_E}{83.2\omega^{0.54}}(1 + \alpha\Delta T) d_p (\rho_L^2 \eta g)^{1/3} \omega^2 \delta,$$

where, $$k_R = k_{R0}\exp\left(-\frac{\Delta E_f}{RT_f}\right),$$

$$T_f = T + 0.55(T_R|_{r=R_f} - T).$$

Where $m_d$ and $m_r$ are the mass deposited and removed, respectively, $\delta$ is the encrust thickness, $k_E$ is the thermal conductivity, $\chi$ is the thermal resistance, $\rho_E$ is the encrust density, m is the encrust mass, $k_m$ is the mass transfer coefficient of solute from the bulk solution to the encrust film, $k_R$ is the adsorption rate of solute to encrust, $C_b$ is the bulk solute concentration, $C_{sat}$ is the saturation concentration within the boundary or film layer, w is the bulk fluid velocity. $\alpha$ is the linear expansion coefficient, $\Delta T$ is the temperature difference between the reactor wall and the encrust surface, $d_p$ is the encrust particle diameter, $\eta$, is the film viscosity, and g is the gravitational acceleration. The adsorption rate is modeled as an Arrhenius-type expression where $k_R 0$ is the adsorption rate constant, $\Delta E_f$ is the activation energy, R is the ideal gas constant, and $T_f$ is the film temperature. It is worthwhile to note here that the expression involving the deposition event is derived via mass transfer while the removal term is proposed constitutively but has been shown to be in precise agreement with experimental observations for the case of $CaSO_4$. In addition, the mass transfer coefficient can be semi-empirically calculated using the Sherwood number:

$$Sh = 0.034 Re^{0.875} Sc^{1/3}, Sh = \frac{2R_f k_m}{D}, Re = \frac{2R_f \omega \rho_L}{\eta}, \quad (3)$$

$$Sc = \frac{\eta}{\rho_L D}.$$

Here, $R_f$ is the PFC radius, D is the solute diffusivity, $\rho_L$ is the liquid bulk density, Re is the Reynold's number, and Sc is the Schmidt number. The encrustation kinetics is coupled with the PFC-PBM dynamics as well as the energy and mass balances. The energy balance is divided into three regions (FIG. 6), namely conduction across the reactor wall ($\Omega_W$: $r \in [R_f, R_0]$), conduction across the encrust ($\Omega_E$: $r \in [R_i, R_f]$) and the convection within the tube ($\Omega_T$: $r \in [0, R_i]$). Both the conduction and convection dynamics yield the following set of coupled differential equations:

Wall: $\frac{\rho_W C_{p,W}}{k_W}\frac{\partial T_W}{\partial t} = \frac{1}{r}\frac{\partial T_W}{\partial r} + \frac{\partial^2 T_W}{\partial r^2} + \frac{\partial^2 T_W}{\partial z^2},$ (4)

Encrust: $\frac{\partial T_E}{\partial t} = \frac{k_E}{\rho_E C_{p,E}}\left[\frac{1}{R_i - \tilde{r}\delta}\left(\frac{-1}{\delta}\right)\frac{\partial T_E}{\partial \tilde{r}} + \frac{1}{\delta^2}\frac{\partial^2 T_E}{\partial \tilde{r}^2} + \frac{\partial^2 T_E}{\partial z^2}\right],$ Tube: $\frac{\partial}{\partial t}(A_f T) =$ $-\frac{\partial}{\partial z}(u A_f T) + \frac{k}{\rho C_{p,L}} + \frac{\partial}{\partial z}\left(A_f \frac{\partial T}{\partial z}\right) + \frac{2\pi R_f h}{\rho C_{p,L}}(T_E|_{R_f} - T),$ where $\tilde{r} = R^{i-r}$ is a dimensionless radial coordinate defined such that its range stays between 0 ($r=R_i$) and 1 ($r=R_f$) irrespective of the encrust thickness. The boundary conditions are given as:

$$B.C.: \quad -k_W \frac{\partial T_W}{\partial r}\bigg|_{r=R_i} = -k_E \frac{\partial T_W}{\partial r}\bigg|_{\bar{r}=0}, \quad (5)$$

$$: T_W |_{r=R_i} = T_E |_{\bar{r}=0},$$

$$: -k_E\left(-\frac{1}{\delta}\right)\frac{\partial T_E}{\partial \bar{r}}\bigg|_{\bar{r}=1} = -h(T_E|_{r=R_f} - T),$$

$$: T|_{z=0} = T_{in},$$

where axial symmetry is assumed. h is the overall heat transfer coefficient and $C_{p,L}$ is the specific heat capacity of the liquid slurry. The mass balance in turn is given as:

$$\frac{\partial}{\partial t}(A_f C) = -\frac{\partial}{\partial z}(u_z A_f C) - \frac{\rho_c}{\rho_L}\phi_v\frac{\partial}{\partial t}(A_f \mu_3)2\pi\frac{\rho_E}{\rho_L}(R_i - \delta)\frac{\partial \delta}{\partial t}, \quad (6)$$

$$\rho_E = (1-\epsilon)\rho_c + \epsilon\rho_L,$$

where $\mu_3 = \int_0^\infty L^3 n(t,L,z)$ is the third moment of the CSD and $\alpha_v$ is the volumetric shape factor. $\rho E$ is the encrust density and is inferred from the encrust void fraction $\epsilon$. PBM is a nonlinear PDE known to have very sharp dynamics and discontinuities. A high-resolution finite volume method (HRFV) has proved to be a robust numerical method for solving the PBM equation and is thus applied on (1). In implementing the method, a 'cell' averaging of the CSD is defined initially:

$$n_{i,j} = \frac{1}{\Delta L \Delta z}\int_{L_{i-1/2}}^{L_{i+1/2}}\int_{z_{j-1/2}}^{z_{j+1/2}} n(t,L,z)dLdz. \quad (7)$$

When (7) is substituted into (1), this yields a set of finite difference ODEs:

$$\frac{d}{dt}(A_f n)_{i,j} = \frac{1}{\Delta L}(GA_f n|_{i+1/2,j} - GA_f n|_{i-1/2,j}) - \quad (8)$$
$$\frac{1}{\Delta z}(u_z A_f n|_{i,j+1/2} - u_z A_f n|_{i,j-1/2}).$$

Note that $A_f$ only varies in the z direction and is therefore only associated with the index j and is constant along i. The HRFV method uses Van Leer's Flux Limiter to ensure that the fluxes between the cell boundaries are sufficiently smooth. The flux is the weighted average of two cells given by:

$$n_{i+1/2,j} = n_{i,j} + \phi(r_{i+1/2,j})(n_{i+1,j} - n_{i,j}), \quad (9)$$

where $\varphi(r)$ is the Van Leer's Flux Limiter defined as:

$$r_{i+1/2,j} = \frac{n_{i,j} - n_{i-1,j} + e}{n_{i+1,j} - n_{i,j} + e}, \quad \phi(r_{i+1/2,j}) = \frac{r_{i+1/2,j} + |r_{i+1/2,j}|}{1 + |r_{i+1/2,j}|}. \quad (10)$$

Here, e is a small value to prevent division by 0. Analogous expressions can be defined in terms of the index j+½ for $n_{i,j}+½$, $r_{i,j}+½$ and $\varphi(r_{i,j}+½)$. The B.C.'s in (1) applies to the fluxes at the boundary as follows:

$$\text{for } i = 0: n_{i+1/2,j} = \frac{B(S_j)}{G(S_j)}, \quad (11)$$

$$i = 1: n_{i+1/2,j} = \frac{n_{i,j} + n_{i+1,j}}{2},$$

$$i = N_L: n_{i+1/2,j} = n_{N_L,j},$$

$$j = 0: n_{i+1/2} = n_{seed},$$

$$j = 1: n_{i,j+1/2} = \frac{n_{i,j} + n_{i,j+1}}{2},$$

$$j = N_z: n_{i,j+1/2} = n_{i,N_z}.$$

$N_L$ and $N_z$ corresponds to the grid size in the direction of crystal size and reactor length, respectively. In the case of under saturation, the PBM equation becomes:

$$\frac{\partial}{\partial t}(A_f n) + \frac{\partial}{\partial z}(u_z A_f n) - \frac{\partial}{\partial L}(DA_f n) = 0, \quad (12)$$

$$B.C.: n(t,L,z)|_{L=0} = 0,$$

where D is the dissolution rate. The HRFV flux expressions and the B.C's for the cell in which dissolution takes place may in turn be appropriately modified with respect to the crystal size index i (The B.C's in terms of j stays the same).

$$n_{i+1/2,j} = n_{i,j} + \phi(r_{i+1/2,j})(n_{i,j} - n_{i+1,j}), \quad (13)$$

$$\text{for } i = 0: n_{i+1/2,j} = n_{1,j},$$

$$i = N_L - 1: n_{i+1/2,j} = \frac{n_{N_L-1,j} + n_{N_L,j}}{2},$$

$$i = N_L: n_{i+1/2,j} = 0.$$

The list of parameters used in solving the coupled mass, energy and population balance equations are listed in Table 1. These dynamical models are subsequently used to simulate and analyze PFC case studies as well as propose a particular a model-based design of AFC.

TABLE 1

| Parameter | Value | Units |
| --- | --- | --- |
| ρW | 2230 | kg · m$^{-3}$ |
| $C_{P,W}$ | 753 | J · Kg$^{-1}$K$^{-1}$ |
| $k_W$ | 1.005 | W · m$^{-1}$K$^{-1}$ |
| ρE | 1750 | kg · m$^{-3}$ |
| $C_{P,W}$ | 870 | J · Kg$^{-1}$K$^{-1}$ |
| $k_d$ | 1.27 × 10$^{-2}$ | m · s$^{-1}$ |
| $k_E$ | 1.11 | W · m$^{-1}$K$^{-1}$ |
| $k_{RO}$ | 2.36 × 10$^6$ | m$^4$Kg$^{-1}$s$^{-1}$ |
| $d_p$ | 36 × 10$^{-6}$ | m |
| D | 1.57 × 10$^{-9}$ | m$^2$s$^{-1}$ |
| E | 37143 | J · mol$^{-1}$ |
| α | 1 × 10$^{-6}$ | K$^{-1}$ |
| η | 600 × 10$^{-6}$ | Pa · s |
| ε | 0.2 | — |
| ρl | 1080 | kg · m$^{-3}$ |
| $C_{P,l}$ | 4185.5 | J · Kg$^{-1}$K$^{-1}$ |
| k | 0.58 | W · m$^{-1}$K$^{-1}$ |
| h | 1000 | W · m$^{-2}$K$^{-1}$ |
| $j_a$ | 1.70 × 10$^8$ | #m$^{-3}$s$^{-1}$ |
| $j_b$ | 5.64 × 10$^6$ | K$^3$ |
| $k_b$ | 3.14 × 10$^7$ | m$^{-3}$s$^{-1}$ |
| j | 1 | — |
| b | 1.32 | — |
| $K_{G0}$ | 2.05 × 10$^5$ | m · s$^{-1}$ |
| g | 1.42 | — |
| γ | 7.18 × 10$^2$ | — |
| β | 6.10 × 10$^5$ | m |
| $\Delta E_G$ | 5.77 × 10$^4$ | J · mol$^{-1}$ |

TABLE 1-continued

| Parameter | Value | Units |
|---|---|---|
| $\alpha_v$ | — | — |
| $k_D$ | $10.72 \times 10^{-9}$ | $m \cdot s^{-1}$ |
| q | 0.51 | — |
| d | 0.34 | — |
| A | $4.58 \times 10^{-5}$ | — |
| B | $2.43 \times 10^{-4}$ | — |
| C | $4.63 \times 10^{-2}$ | — |
| $N_r$ | 20 | — |
| $N_L$ | 20 | — |
| $N_z$ | 20 | — |
| Segments | 4 | — |
| Z | 240 | cm |
| $R_f$ | 7.5 | mm |
| $R_o$ | 9.5 | mm |
| Q | 40 | $mL \cdot min^{-1}$ |
| κ | $1 \times 10^8$ | — |
| $\mu_{seed}$ | 54 | μm |
| $\mu_{seed}$ | 15 | μm |
| $T_{in}$ | 38 | °C |

Example 2: Solubility Phase Diagram in the Presence of Fouling

Figure 7:
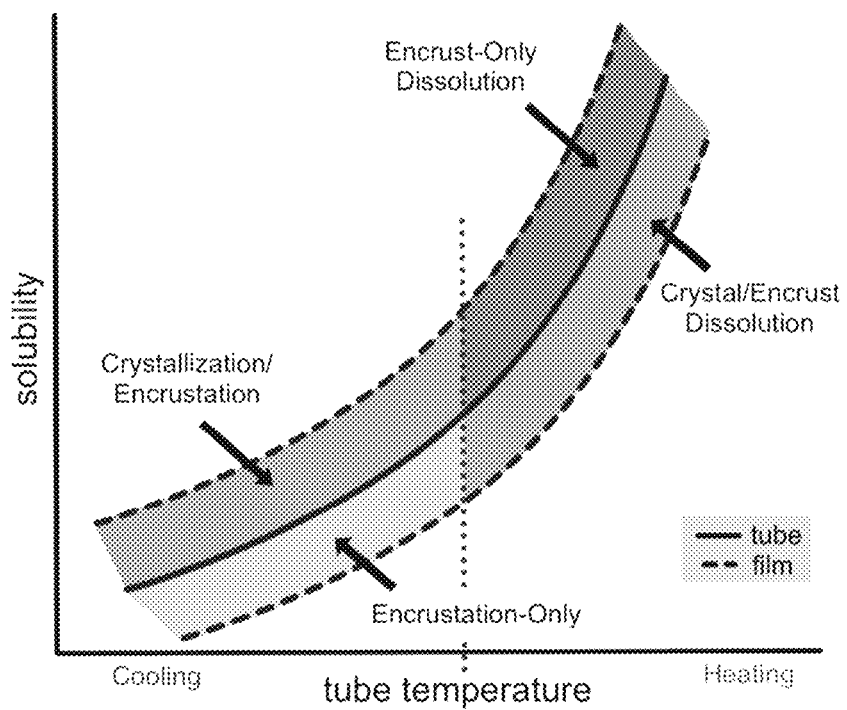
FIG. 7 is a solubility phase diagram in the presence of encrustation. During cooling (heating), the temperature of the encrust layer is lower (higher) than that of the tube resulting in higher (lower) film saturation within the boundary layer, which separates the encrust and the flow.

Due to the presence of a boundary layer between the encrust and the tube, there exists a temperature gradient between the two domains as is modeled explicitly in Eq. 2. Consequently, during cooling, the film temperature is lower than that of the tube, while during heating it is higher. The supersaturation in the growth phase and under saturation in the dissolution phase are thus always stronger for the encrust dynamics relative to that for crystallization (FIG. 7). The model is therefore consistent with the observation that in order to have crystal growth, encrustation must also take place. On the other hand, during heating, there is a small region in which dissolution of the encrust can happen without crystal dissolution. A temperature profile can therefore be theoretically designed which dissolves encrust while maintaining supersaturation within the tube to prevent loss of crystal yield. As will be discussed herein, this region is in fact too small for the temperature control to be practically realized in AFC. It does, however, provide a window for fouling mitigation without significant dissolution of the crystals. Nevertheless, it is important to note that while the super- and undersaturation driving force for the encrust dynamics in the boundary layer are always higher than those for crystals in the tube, the encrust growth or dissolution is not necessarily faster. These would depend on the magnitude of the mass transfer to the boundary layer and the adsorption and desorption rate onto the encrust, which themselves are a function of temperature. As these values are yet to be experimentally determined for our crystallization system of choice, i.e. potash-alum, known parameters for other systems are used. As would be mentioned in details herein, these values correspond to a lower rate of mass deposited onto the encrust when compared with crystal growth, but which is a fair assumption according to a recent laboratory observation, that encrust starts to become significant after several residence times.

Example 3: Optimization of Crystal Mean Size in the Presence of Fouling

The purpose of this example is to compare PFC operation which is optimized for maximizing CSD ($L_{43}$) in the presence of fouling with that in the absence of it. The optimization problem is formulated as follows:

$$\max_{T_i} \mathcal{J}(\mathcal{T}) = L_{43}(\mathcal{T}), \quad (14)$$

$$i \in [1, 4], \mathcal{T} = 12\tau, \tau = \frac{u_z}{Z},$$

s.t.: (1) to (6), $$20 \leq T_i \leq 40,$$

for $$S > 0: G(S, L) = k_G \exp\left(-\frac{\Delta E_G}{RT}\right) \times (1 - \exp(-\gamma(L + \beta)))(\sigma - 1)^g,$$

$$B(S) = J_{prim} + J_{sec},$$

$$J_{prim} = j_a \exp\left(\frac{j_b}{T^3 (\ln \sigma)^2}\right),$$

$$J_{sec} = k_b M_T^j S^b,$$

$$M_T = \rho_c \alpha_v \mu_3,$$

$$\sigma = \frac{C}{C_{sat}},$$

$$S = C - C_{sat},$$

$$C_{sat} = AT + BT^2 + CT^3$$

for $$S < 0: D(S, L) = \frac{k_D}{L^q}(-S)^d.$$

The above solubility and kinetic expressions, including primary and secondary nucleation as well as size-dependent growth, correspond to potash-alum crystals. The encrustation rate parameters are, however, unknown and values corresponding to a significant blockage after several residence times are assumed. The full list of parameter values with references are given in Table 1. Additionally, a seeded process is assumed and the seed density is modeled as a normal distribution:

$$n_{seed} = \frac{K}{\sigma_{seed}\sqrt{2\pi}} \exp\left(-\frac{(L - \mu_{seed})^2}{\sigma_{seed}^2}\right). \quad (15)$$

Figure 8A:
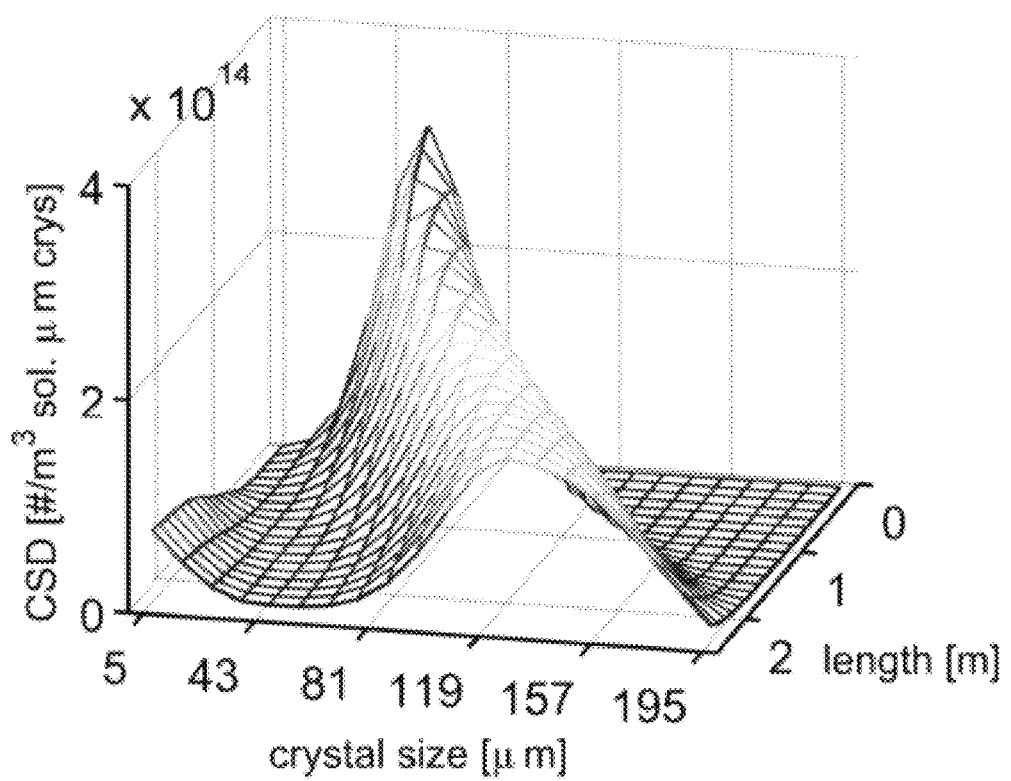
FIGS. 8A-D show optimization of crystal mean size ion the presence of encrustation.
Figure 8B:
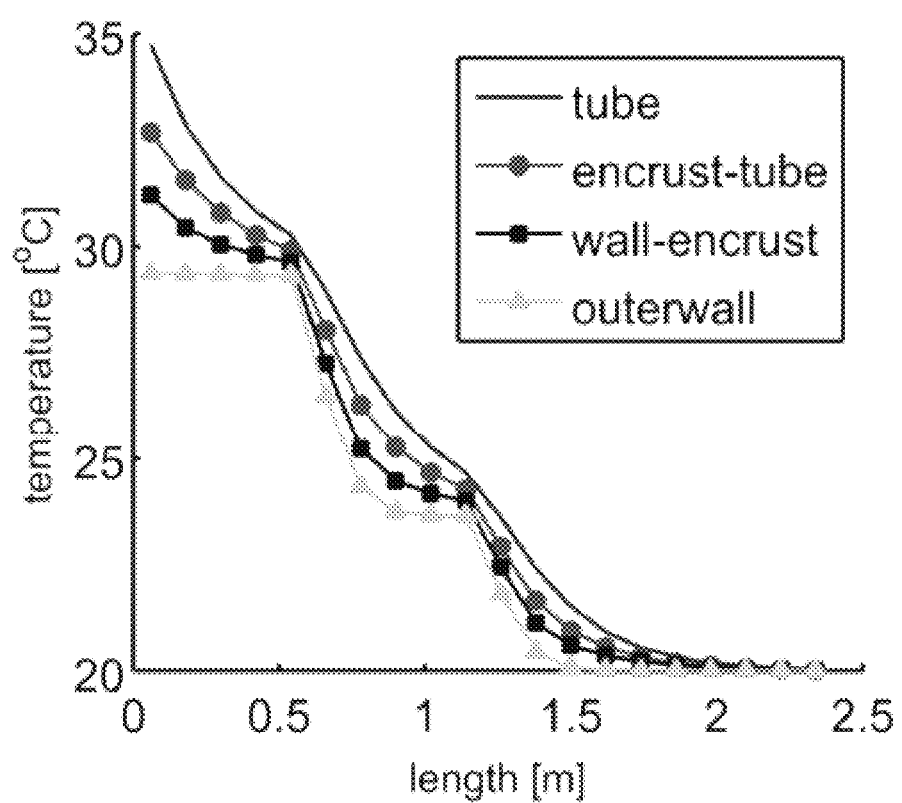
Figure 8C:
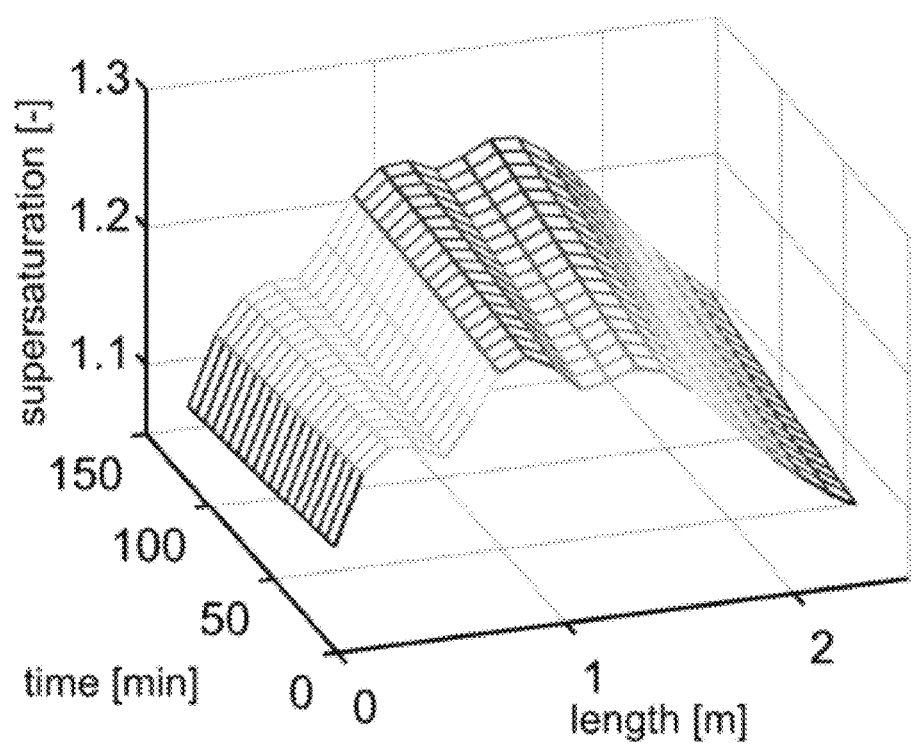

Here, κ is a scaling factor determined according to the desired seed mass fraction relative to that of slurry. The choice of optimization routine is genetic algorithm (GA) as it has been shown reliable in producing the optimal manipulated parameters corresponding to objective functions common in batch and continuous crystallizations. It is employed with the following initial conditions (I.C's): (1) the tube temperature equals the in-flow temperature, (2) the tube concentration starts at supersaturation, and (3) there is no initial crystal or encrust. The optimization is in turn performed with the fouling kinetics artificially turned off. The results of are summarized in FIGS. 8A-D and 9. The simulation shows that, as expected, the crystal's seed CSD increases as it moves along the PFC (FIG. 8A). Due to primary and secondary nucleation, some fine particles form and increases in size along the PFC as shown in the leading edge of the CSD profile. FIG. 8B indicates that the temperature profile of the tube lags in comparison with that of the jacket. This is expected due to heat conduction across the wall and the encrust and heat convection across tube.

Figure 8D:
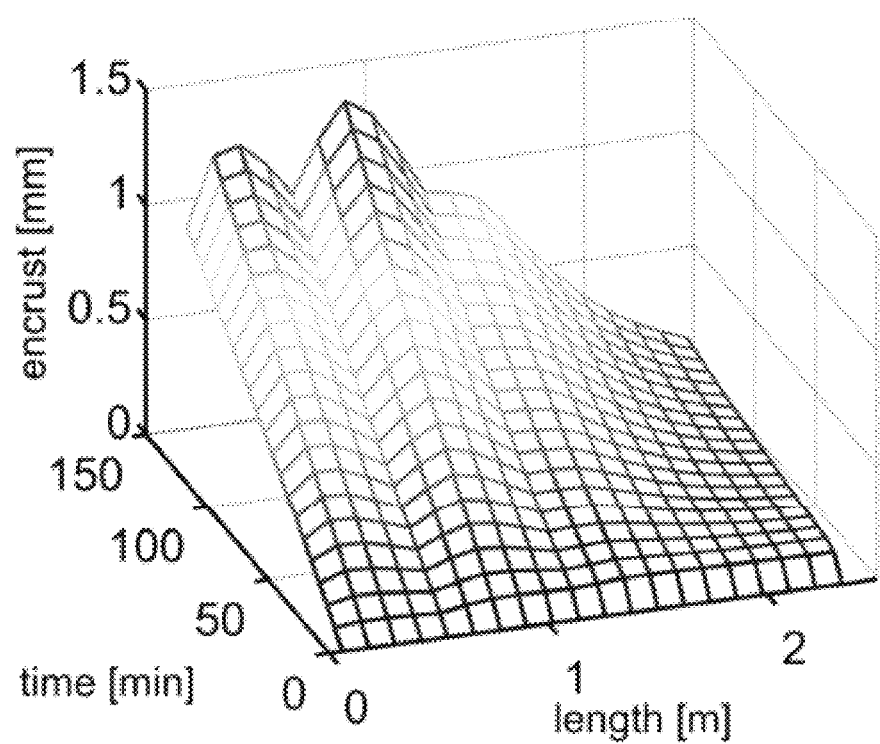
Figure 9:
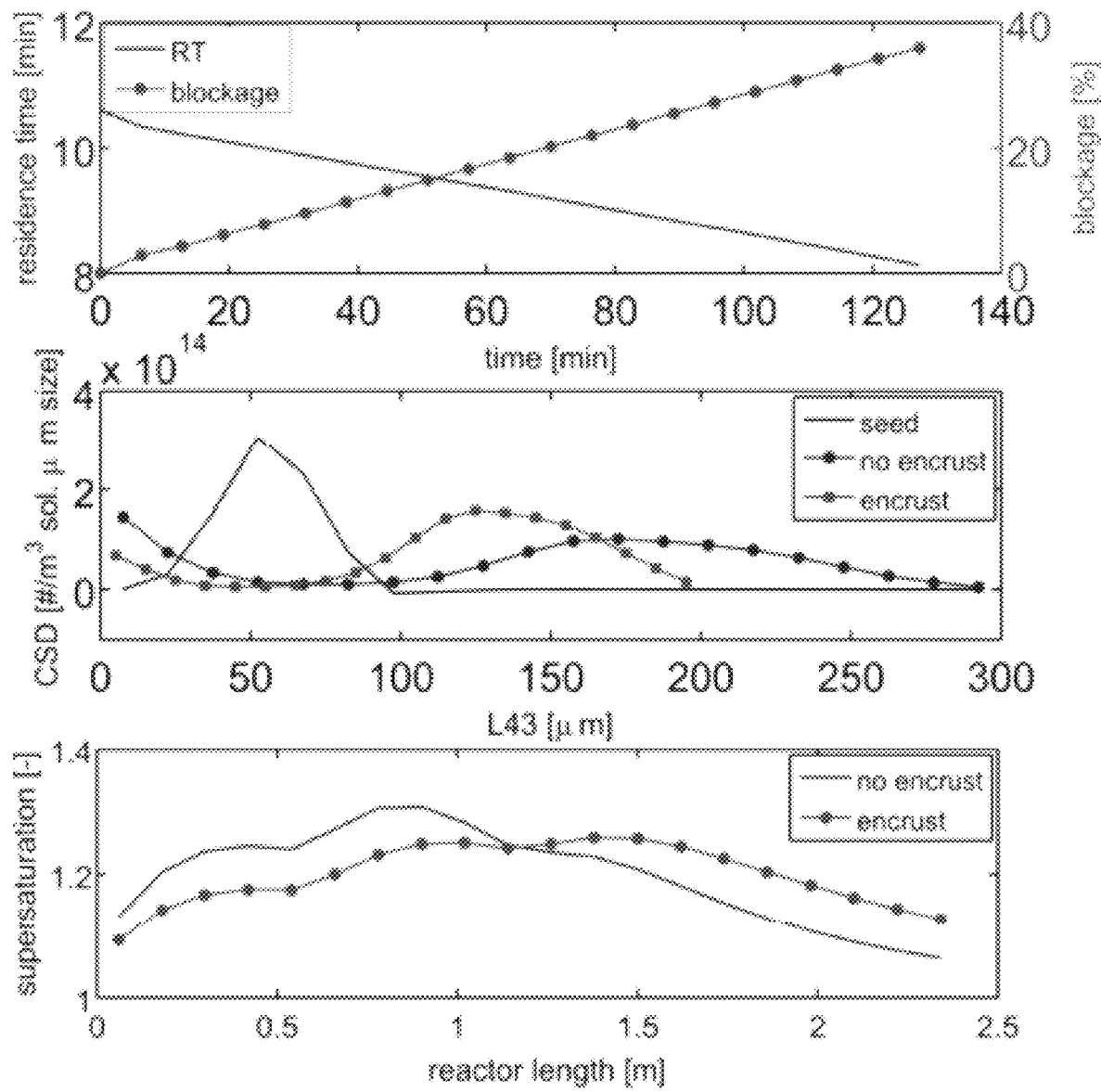
FIG. 9 are graphs showing a comparison between PFC with and without fouling. (Top) Residence time (RT) and % blockage—when fouling is not present the line stays flat from the beginning. (Middle) CSD, (Bottom) Supersaturation.

The thicker the encrust the more is the difference between the controlled jacket temperature and the tube temperature. The results also suggests that while the optimization leads to formation of large crystals, it results in significant encrust formation (FIG. 8D). As shown in FIG. 9 (top, circled line), assuming less than 40% blockage is required for normal operation the PFC must halt and be cleaned after 12th residence time (RT), essentially rendering it a batch process. It is important to note that contrary to the profile of supersaturation, which started at a low value and peaked around the middle point of the PFC, the largest encrust growth takes place in the leading segment of the PFC. This is because the encrustation rate is also a function of temperature which reduces further down the segment. The optimization in turn was able to pick the temperature profile which takes advantage of the trade-off between crystal and crust growth kinetics. In other words, the encrust kinetics differ from that of crystal growth, which is a much stronger function of supersaturation and thus have analogous profile across the PFC shown in FIG. 8C and FIG. 9 (bottom, red). When the results are compared to a crystallization process with fouling kinetics hypothetically switched off, blockage is avoided and in turn the heat transfer dynamics and super-saturation level is reduced such that both the crystal mean size and yield is higher (FIG. 9 (middle)). These phenomena can be further explained using the supersaturation curves of FIG. 9 (bottom), in which the encrust-off operating curve (blue) is situated at a higher supersaturation region relative to the encrust-on counterpart (red) at the beginning of cooling and approaching closer to the saturation point at the end to maximize yield. The yield of the process according to the difference between mass flow in and out (Eq. 16) and according to the theoretical yield (Eq. 17) is 37% and 97%, respectively.

$$\text{mass yield} = \frac{C_{in} - C_{out}}{C_{in}} \quad (16)$$

$$\text{theoretical yield} = \frac{C_{out}}{C_{sat}(T_{min})} \quad (17)$$

The latter value is used as a reference for the following Examples as well as the proposed AFC design.

Example 4: Minimization of Encrustation with Minimal Crystal Growth

In this Example, an optimization is performed to minimize encrust while maintaining desired crystal growth. The problem formulation is expressed analogously to the first case as follows:

$$\min_{T_i} \mathcal{J}(\mathcal{T}) = |\delta(\mathcal{T})|_\infty, \quad (18)$$

$$i \in [1, 4], \mathcal{T} = 12_\tau, \tau = \frac{Z}{u_z}$$

s.t.: (1) to (6), (14) and (15)

Figure 10:
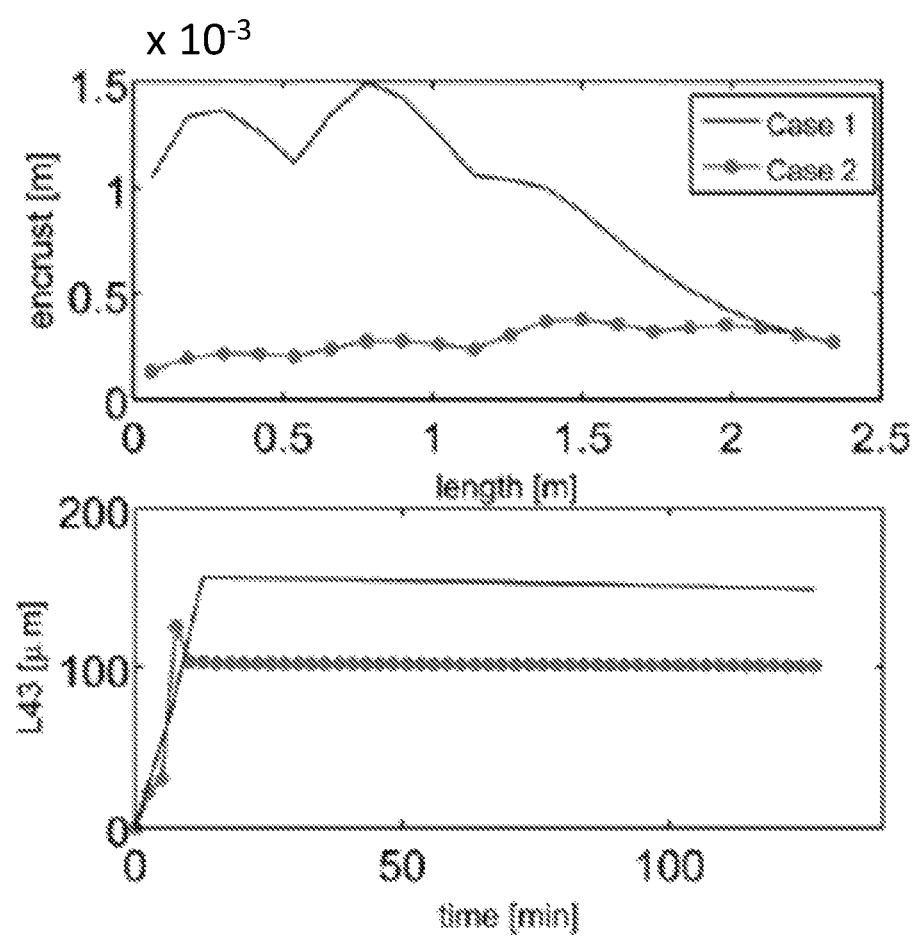
FIG. 10 are graphs showing a comparison between two different case studies. (Top) Encrust thickness and (Bottom) Crystal mean size (L43). The figure shows that fouling can be significantly reduced (10% vs. 40% blockage) at the expense of moderate crystal growth (100 µm vs. 150 µm).

The same simulation parameters, including the B.C's and I.C.'s, and optimization routine are used. The results, shown in FIG. 10, illustrate how the extent of encrust formation maybe significantly decreased (top), and PFC operation prolonged at the expense of moderate crystal mean size reduction (bottom). As implied from the supersaturation curve, the driving force for crystallization is only utilized as much as required to maintain minimal crystal growth so as to induce minimal encrustation. The lifetime of the PFC is in turn prolonged by as much as 6 times relative to that in the first case study, before the residence time is significantly reduced and the CSD fall below specification. At the same time, the theoretical yield of the process is also reduced significantly from 97% to 26%. The two case studies showed the trade-offs between crystal quality and prolonged operation and serve as comparative cases for the AFC design in which fouling is completely eliminated. The two case studies are the extremes of the PFC operations and a novel AFC design which can operate in between these two conditions while realizing continuous operation would improve the viability of PFC as a future crystallizer.

Example 5: Model-Based Anti-Fouling Control (AFC)

Figure 11:
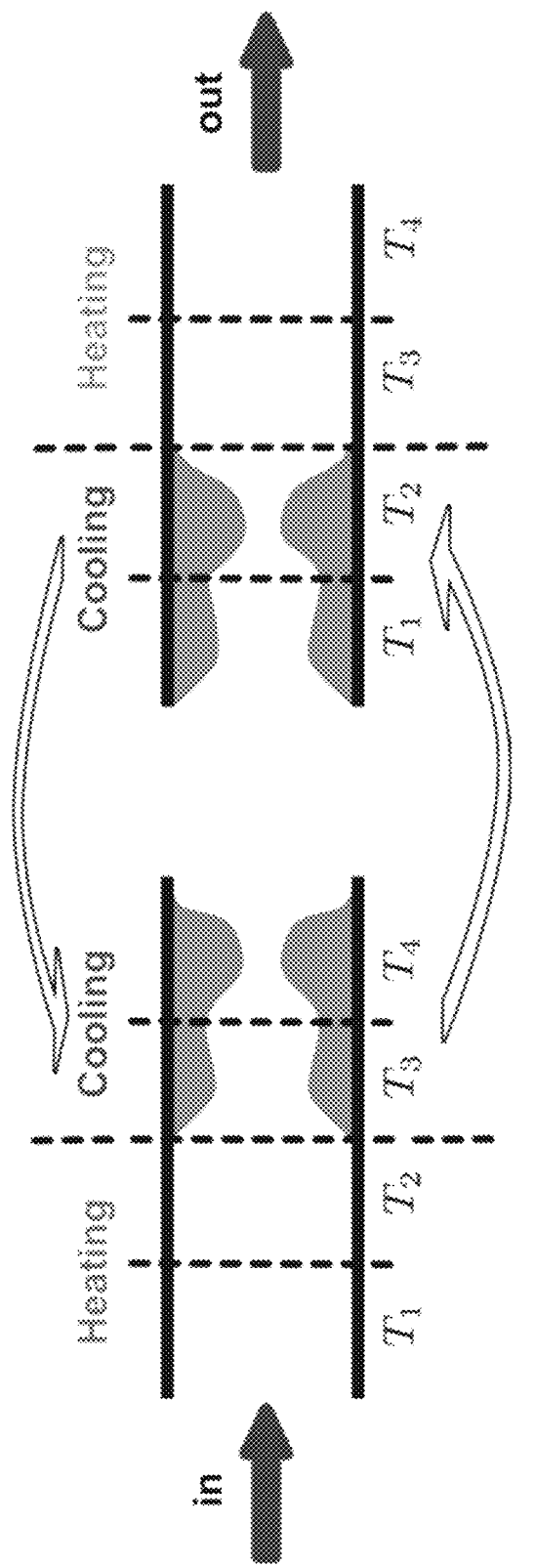
FIG. 11 is a schematic of an open-loop AFC. The PFC is divided into equal halves of heating and cooling segments. The spatial temperature profiles are optimized periodically (every multiples of residence time) to maximize growth in the cooling segment and minimize dissolution in the heating segment.

The AFC design is realized by implementing a temperature profile which can grow crystals in one segment while dissolving the encrust without impacting crystal growth in another segment in continuous cycles. As discussed above, such temperature profile is possible due to the difference in the film and tube temperature and, therefore, the different degree of supersaturation driving force for crystal and encrust dissolution. While the dissolution parameters for the encrust is not known a priori, the value of dissolution rate is chosen such that the magnitude in terms of thickness per unit time is comparable to that of the crystal. To this end, a multi-segment PFC is divided into two symmetric parts, which periodically cycle between cooling and heating regions (FIG. 11). In the cooling segment, the temperature is optimized such that crystal growth is maximized, while in the heating segment, complete encrust dissolution is enforced but with crystal dissolution minimized. The optimization problem can be formulated as follows:

$$\max_{T_i} \mathcal{J}(\mathcal{T}) = L_{43}(\mathcal{T}) \quad (19)$$

s.t.: (1) to (6), (14) and (15), and heating: $20 \leq T_i \leq 35$, cooling: $39 \leq T_i \leq 45$, $\delta(\mathcal{T}, x_{heat}) = 0$.

Figure 12:
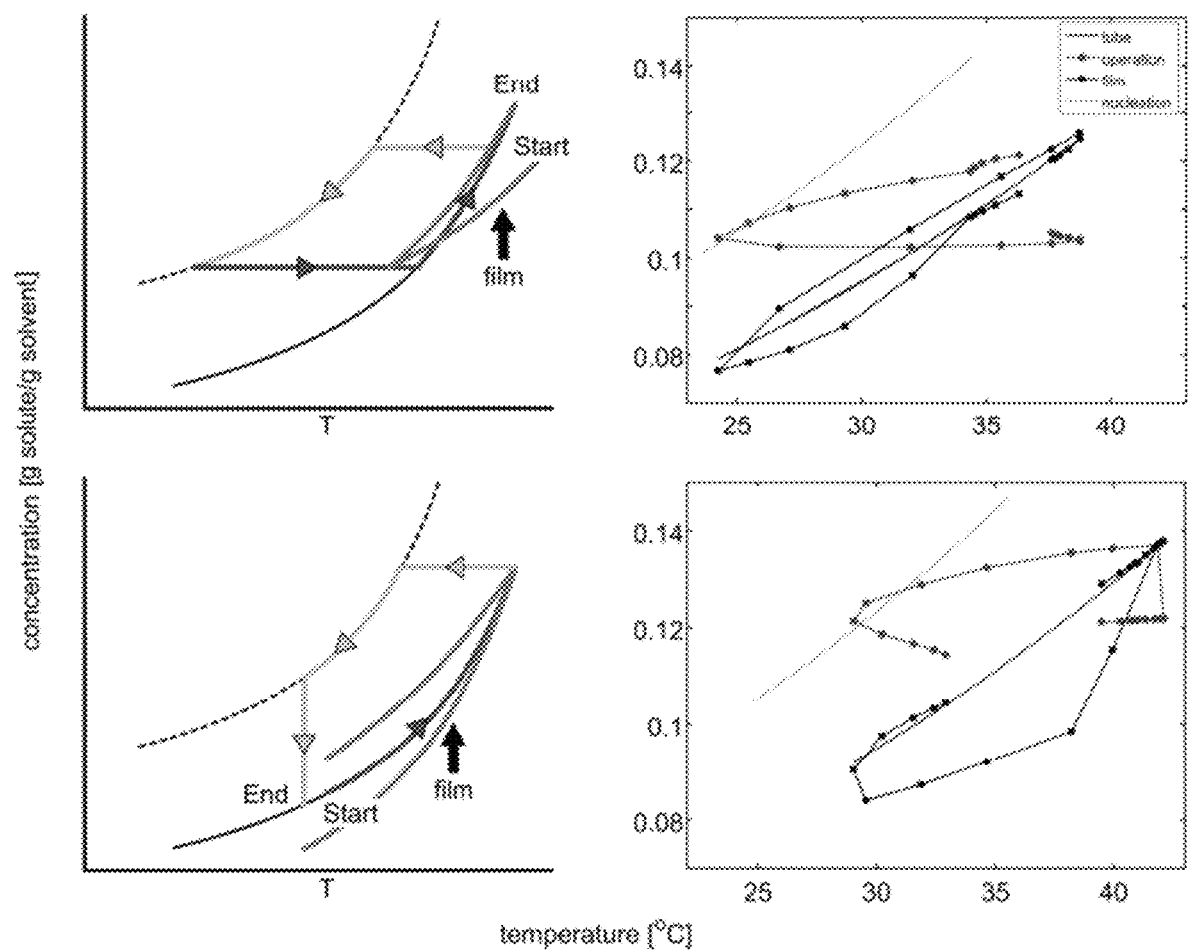
FIG. 12 is a set of graphs showing theoretical (left) and practical (right) operating curves of AFC. (Top) In the first cycle, the curve starts at supersaturation enforcing crystal and encrust growth and moves towards undersaturation for encrust dissolution along the PFC. (Bottom) In the second cycle, the reverse takes place in which the cycle starts at undersaturation to dissolve the encrust built up in the previous cycle and progress towards supersaturation in the later half of the PFC.
Figure 13A:
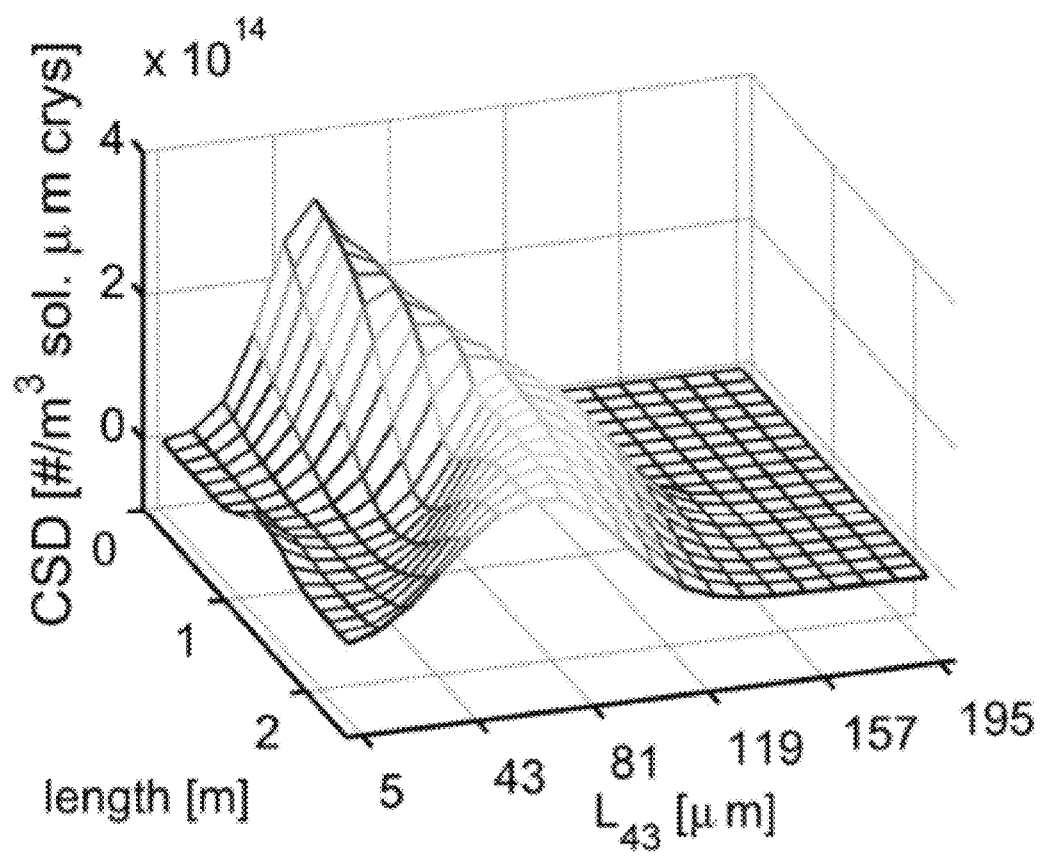
FIGS. 13A-D are simulations of AFC via spatial and temporal heating and cooling cycles.
Figure 13B:
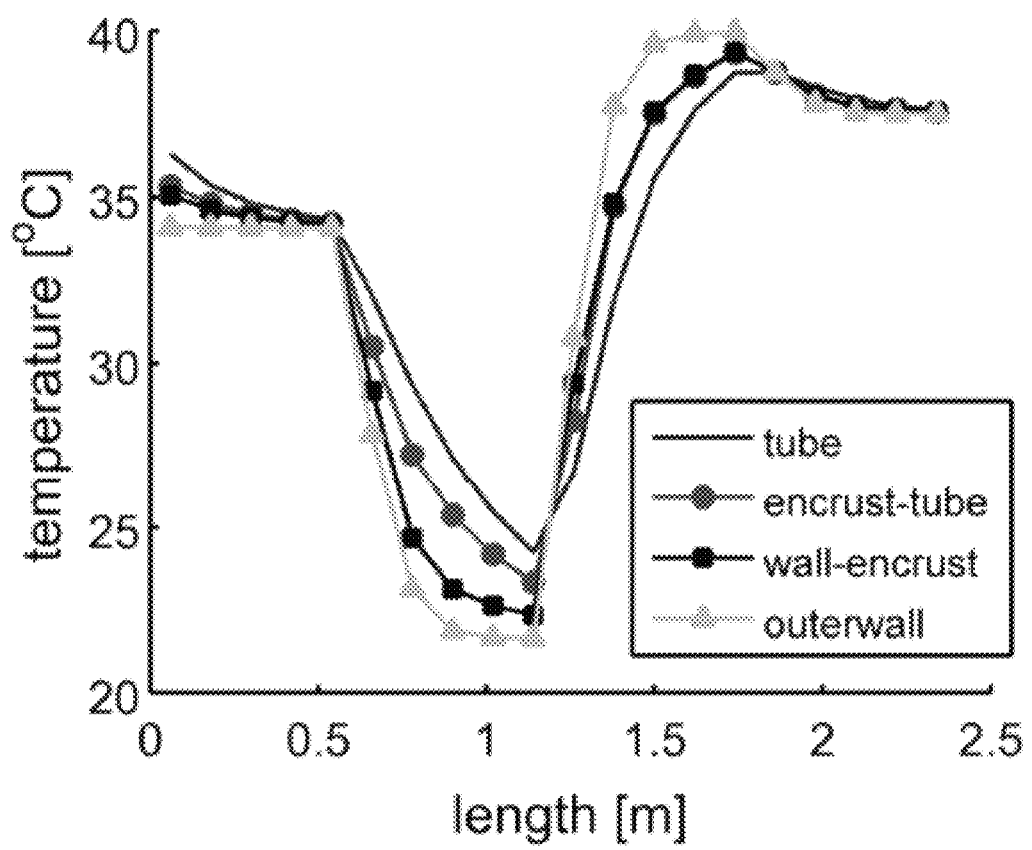
Figure 13C:
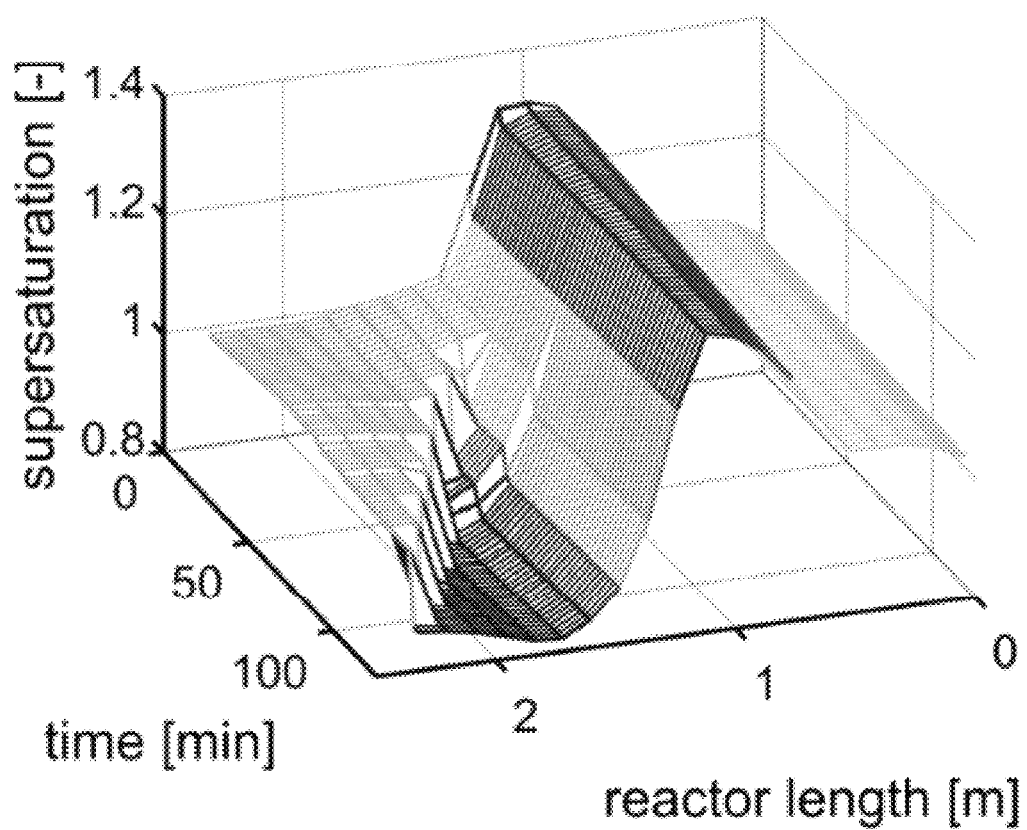
Figure 13D:
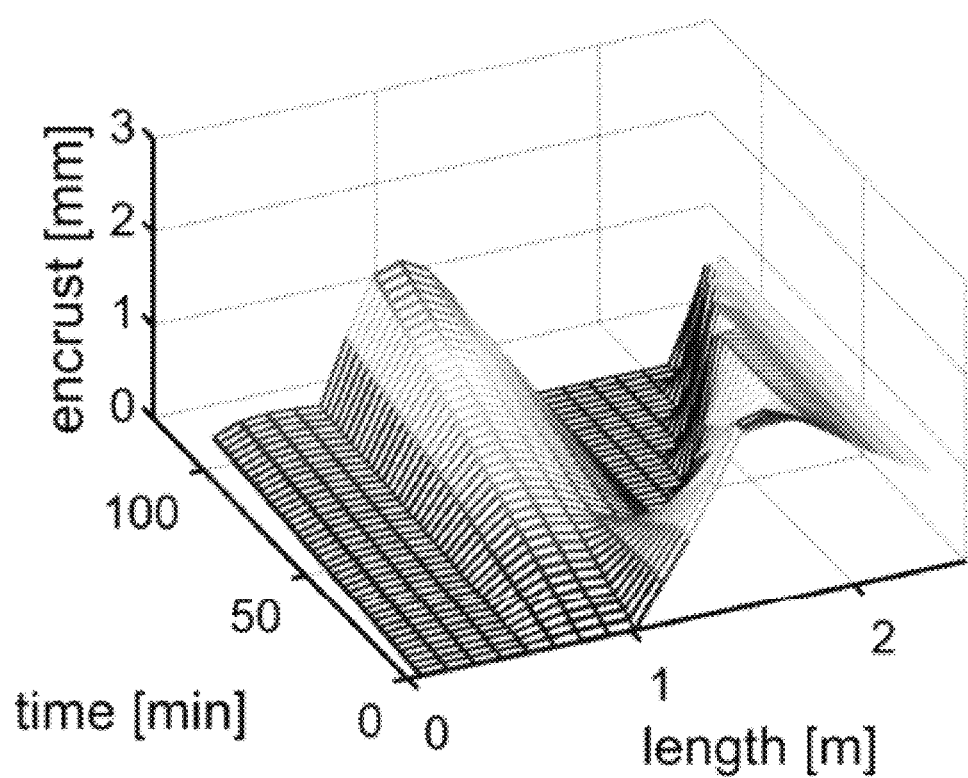

Note that the heating region does not automatically correspond to dissolution region. Depending on the rate of encrust and crystal growth, the concentration of slurry moving into the heating region may be such that it requires some time, and thus, over a reactor length, before prior dissolution takes place. Since the optimal temperature profile is to be calculated per cycle, the segments are alternating between heating and cooling cycle. In this work, the convention is that the leading segment is first cooled and the later segment heated resulting in an odd cycle of cooling-heating PFC and even-cycle of heating-cooling counterpart. In the theoretical limit, the optimal temperature profile within the tube would be one which allows optimal operating curve along the solubility diagram as shown in FIG. 12 (top and bottom left) for the odd and even cycle, respectively. The operating curve is not necessarily symmetric and, as a consequence, the I.C's for the next iteration of the optimization and in turn the optimal temperature profile may differ from cycle to cycle. The ideal AFC operating curve would maximize crystal growth without inducing primary nucleation in the metastable region during cooling while minimizing crystal dissolution but ensuring complete encrust dissolution during heating. Visually, this control profile is achieved by operating at the tube solubility and below the film solubility so as to enforce encrust dissolution but without dissolving the crystal. The results of the optimization, however, shows that this is not possible given the limitation of attainable temperature profile within the tube and since there is an operational constraint taken into account in the optimization which requires that the encrust dissolution complete within a specific duration. Instead, the optimization produces an operating curve close to the primary nucleation threshold during cooling while, during heating, the curve fall well beyond the encrust and crystal solubilities (FIG. 12 (top and bottom right)). The responses of this control profile for the first cycle and in terms of (1) CSD dynamics, (2) temperature gradients across the different PFC and encrust domains, (3) supersaturation dynamics, and (4) the encrustation dynamics are shown in FIGS. 13A-D. Specifically, the CSD oscillates from growth to dissolution as it moves along the cooling and the heating segment (FIG. 13A). As the encrust dissolves on the leading part of the tube (FIG. 13D), the dissolved solute prevents undersaturation in the tube as well as the film. As a result, the encrust dissolves gradually (FIG. 13C).

Figure 14A:
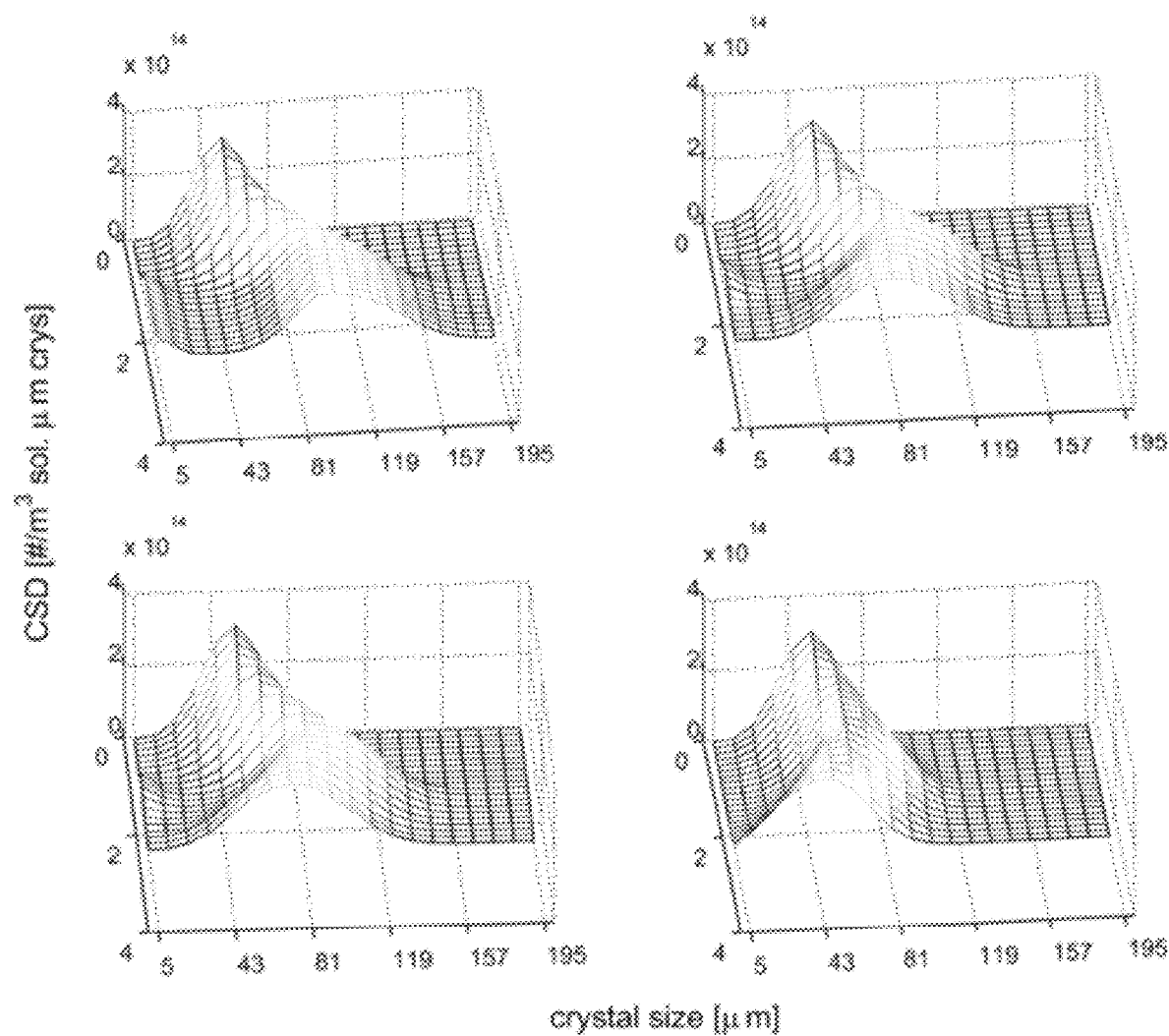
FIGS. 14A-B show the levels of super- and undersaturation in the tube and the film becomes more pronounces as time increases (FIG. 14B) and this corresponds to reduction in the output CSD (FIG. 14A). As the crystal travels along the reactor, the crystals grow in the cooling region and dissolve in the heating counterpart. The cooling effect, however, grows weaker due to the thickening of the encrust and the impact of dissolution becomes more significant as there is less encrust to dissolve to maintain supersaturation.
Figure 14B:
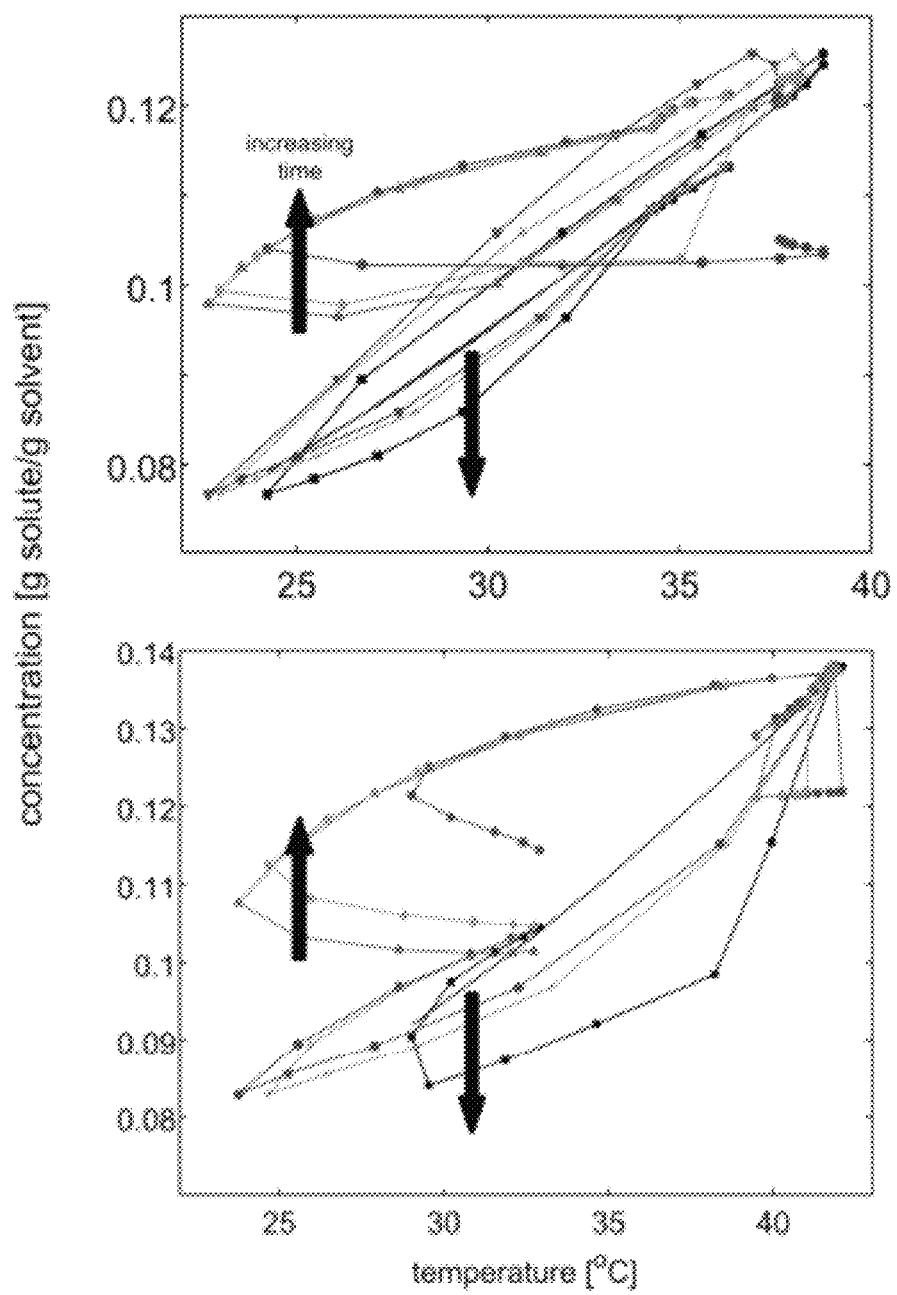

Furthermore, the levels of super- and undersaturation in the tube and the film becomes more pronounced as time increases (FIG. 14B) and this corresponds to reduction in the output CSD (FIG. 14A). The cooling effect grows weaker due to the thickening of the encrust and the impact of the dissolution becomes more significant as there is less encrust to dissolve to maintain supersaturation in the heating region. Thus, without accurate parameter estimation of the state of the system at the beginning of each AFC cycle, overheating and undercooling result in less then optimal. A comparison between the open-loop AFC method with the two case studies are summarized in Table 2.

TABLE 2

| Case | L43 | CV | Yield |
|---|---|---|---|
| Maximized growth | 148 | 0.17 | 97 |
| Minimized encrust | 100 | 0.19 | 26 |
| Open-loop AFC | 108 | 0.22 | 42 |

The results show that the performance of AFC is satisfactory over the first two cycles and is the intermediary between the two extremes of optimized PFC operations without anti-fouling mechanism in place. The yield of AFC is cut by approximately half since only half the PFC segment is used for cooling such that the lowest temperature is not reached and in turn the solute mass is not converted into solid. As discussed in later Examples, the yield may be overcome at the expense of 'over-designing' the PFC by making it twice as long. While the benefits of implementing model-based AFC are clear.

In this work, model-based AFC is proposed and described for treating fouling in a plug flow crystallizer. The method is compared with a couple of case studies in which optimized PFC operations without anti-fouling mechanism are described. The first case involves PFC operation where growth is maximized and the second concerns operation in which encrust is minimized. It was illustrated that an optimized PFC crystallization dynamics are affected by encrustation in the following number of ways:

The PFC process may not reach steady state such that encrust continues to build up until it blocks the flow completely, Encrustation leads to progressively decreasing resi-dence time which subsequently reduces the effective duration of crystal growth and, therefore, crystal size, Encrust deposits present additional thermal resis-tance, which prevents fast heat transfer across the PFC wall and limits the attainable temperature pro-file within the tube, As encrust competes with crystals for solutes, crystal product yield diminishes, and Finally, the above factors results in variability in the output CSD per "lot of time".

In order to overcome the limitations in a continuous PFC process, a model-based AFC design is introduced and compared with two case studies where crystal growth is maximized and encrust thickness is minimized. The control design demonstrates a proof-of-concept for a completely continuous PFC operation in which encrust is periodically negated and without significant reduction in crystal mean size and significant effect on CV. In addition, the theoretical yield of the process is approximately half as much as that of the optimized operation as only half of the reactor is being used for cooling at each cycle.

Example 6: Model-Free Anti-Fouling Feedback Control of Plug-Flow Crystallization Building upon the open-loop AFC design discussed in the Examples above, a model-free spatio-temporal anti-fouling control (AFC) of plug-flow crystallization (PFC) with on-off feedback controllers is herein demonstrated by simulation and experiments. The control is designed to achieve two-fold objectives, namely (1) the collection of in-spec products based on real-time measurements using available PAT tools and (2) ensuring encrust dissolution without crystal over-dissolution. The design of the crystallizer was studied to maximize the control performance in terms of the number of temperature segments, the segment length and the cycling frequency between the heating and cooling cycles. The results display that the model-free AFC is capable of enforcing product quality by design of the PFC (QbD) and, as importantly, by process monitoring and control (QbC) using readily available PAT tools, such as an FBRM probe and a gray-scale camera.

In this and the following Examples, embodiments are described for a model-free AFC design whereby the spatio-temporal heating and cooling cycles are coupled with a readily implementable CSD and encrust feedback sensors to achieve desired control performance and product quality without cyclical calculation of the optimal control profile or knowledge of the initial conditions at the start of each cycle.

Example 7: Encrustation-Coupled Crystallization Dynamic Model

A model for encrustation in a PFC inspired from the fouling studies of $CaSO_4$ crystals commonly found in heat exchangers have been described. The encrustation dynamics is summarized below:

$$\frac{d\delta}{dt} = k_E \frac{d\chi}{dt} = \frac{k_m}{\rho_E} \frac{dm}{dt} = \qquad (1)$$

$$\frac{k_m}{\rho_E}\left[\frac{1}{2}\frac{k_m}{k_R} + (C_b - C_{sat}^f)\right] - \left(\frac{1}{4}\frac{k_m^2}{k_R^2} + \frac{k_m}{k_R}(C_b - C_{sat}^f)\right)^{1/2}\right] -$$

$$\frac{\rho_E}{83.2\omega^{0.54}}(1 + \alpha\Delta T)d_P(\rho_L^2\eta g)^{1/3}\omega^2\delta,$$

where:

-continued $$k_R = k_{R0}\exp\left(-\frac{\Delta E_f}{RT_f}\right),$$

$$T_f = T + 0.55(T_R|_{r=R_f} - T).$$

Here, δ is the encrust thickness on the reactor's wall, $k_E$ is the thermal conductivity, x is the thermal resistance, ρ is the encrust density, m is the encrust mass, $k_m$ is the mass transfer coefficient of solute from the bulk solution to the encrust film, $k_R$ is the adsorption rate of solute to encrust and assumed to be of Arrhenius type, $C_b$ is the solute concentration in the bulk liquid, $C_f$ is the solubility within the film layer, w is the bulk fluid mixing velocity. α is the linear expansion coefficient, ΔT is the temperature difference between the reactor wall and the encrust surface, $d_p$ is the mean particle diameter within the encrust, η is the film viscosity, and g is the gravitational acceleration. In addition, $k_m$ is semi-empirically correlated with the Sherwood number:

$$Sh = 0.034Re^{0.875}Sc^{1/3}, Sh = \frac{2R_f k_m}{D}, Re = \frac{2R_f \omega \rho_L}{\eta}, Sc = \frac{\eta}{\rho_L D}. \quad (2)$$

The encrustation dynamics is coupled with the crystallization dynamics given by the population balance equation (PBE) as follows:

$$\frac{\partial}{\partial t}(A_f n) + \frac{\partial}{\partial z}(u_z A_f n) + \frac{\partial}{\partial L}(GA_f n) = 0, \quad (3)$$

and with the following boundary conditions (B.C.'s): G(S) n(t, L, z)|$_{L=0}$=B(S), n(t, L, z)| z=0=$n_{seed}$(L). Here, n is the crystal size distribution (CSD), uz is the slurry flow velocity, G is the crystal growth rate, B is the nucleation rate, and $n_{seed}$ is the seed CSD, z is the reactor axis, and L is the crystal length axis. $A_f$(t, z)=$\pi R_f^2$(t, z) is the flow area within the tube which changes with time and along the reactor length due to encrustation. $R_f$ is the PFC radius, D is the solute diffusivity, $\rho_L$ is the bulk liquid density, Re is the Reynold's number, and Sc is the Schmidt number. The encrustation and crystallization dynamics are also coupled with mass and energy transfer equations. The energy balance is divided into three domains, namely conduction across the reactor wall ($\Omega_W$: r∈[$R_f$, $R_o$]), conduction across the encrust ($\Omega_E$: r∈[$R_i$, $R_f$]) and convection within the tube ($\Omega_T$: r∈[0, $R_i$]). Both the conduction and convection dynamics yield the following set of coupled differential equations within the different domains:

$$\text{Wall:} \frac{\rho W C_p, W}{k_W}\frac{\partial T_W}{\partial t} = \frac{1}{r}\frac{\partial T_W}{\partial r} + \frac{\partial^2 T_W}{\partial r^2} + \frac{\partial^2 T_W}{\partial z^2}, \quad (4)$$

$$\text{Encrust:} \frac{\partial T_E}{\partial t} = \frac{k_E}{\rho_E C_{p,E}}\left[\frac{1}{R_i - \tilde{r}\delta}\left(\frac{-1}{\delta}\right)\frac{\partial T_E}{\partial \tilde{r}} + \frac{1}{\delta^2}\frac{\partial^2 T_E}{\partial \tilde{r}^2} + \frac{\partial^2 T_E}{\partial z^2}\right],$$

$$\text{Tube:} \frac{\partial}{\partial t}(A_f T) =$$

$$-\frac{\partial}{\partial z}(uA_f T) + \frac{k}{\rho C_{p,L}}\frac{\partial}{\partial z}\left(A_f \frac{\partial T}{\partial z}\right) + \frac{2\pi R_f h}{\rho C_{p,E}}(T_E|_{R_f} - T).$$

Here, $$\tilde{r} = \frac{R_i - r}{\delta}$$

is a dimensionless radial coordinate which ranges between 0 (r=$R_i$) and 1 (r=$R_f$) irrespective of the encrust thickness. Axial symmetry is assumed with h defined as the overall heat transfer coefficient and $C_{p,L}$ the specific heat capacity of the liquid slurry. The B.C.'s for the different domains can be summarized as follows: (i) first order continuity and identical temperature at the interface between the inner reactor wall and the encrust, (ii) first-order continuity between the rate of heat conduction and heat convection at the interface between the encrust and the tube, and (iii) the inlet temperature along the reactor is defined as the feed temperature. The mass balance in turn is given as:

$$\frac{\partial}{\partial t}(A_f C) = -\frac{\partial}{\partial z}(u_z A_f C) - \frac{\rho_c}{\rho_L}\phi_v \frac{\partial}{\partial t}(A_f \mu_3) - 2\pi \frac{\rho_E}{\rho_L}(R_i - \delta)\frac{\partial \delta}{\partial t}, \quad (5)$$

$$\rho_E = (1 - \epsilon)\rho_c + \epsilon \rho_L,$$

where $\mu_3$=$\int_0^\infty L^3 n(t,L,z)$ dL is the third moment of the CSD and $\alpha_v$ is the volumetric shape factor. $\rho_E$ is the encrust density and can be calculated from the encrust void fraction ε. The resulting encrustation-PBE dynamics is a non-linear and highly stiff PDE which is solved using the high-resolution finite volume method (HRFV). The mass and energy balances are solved via finite differences.

Figure 15:
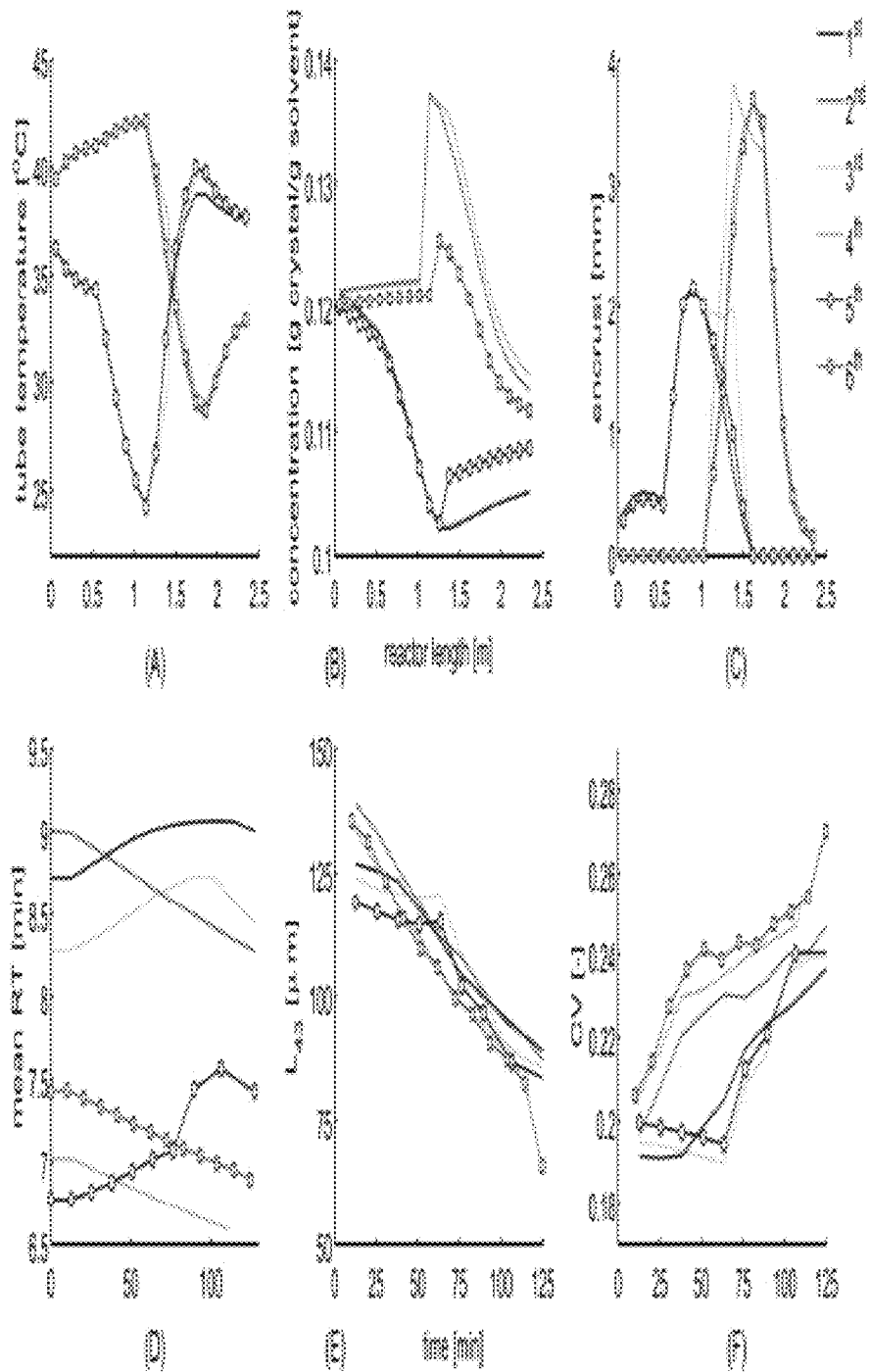
FIG. 15 panels A-F are a set of graphs showing that a PFC system response to periodic AFC control profile implemented over 6 cycles are non-periodic. Panel A is temperature, panel B is concentration, panel C is encrust thickness, panel D is mean RT, panel E is L43, and panel F is CV.

Using the model summarized above, the optimization formulation for the model-free AFC may be identical to that of the open-loop AFC described in. This is summarized as follows: The resulting temperature control profiles for the first two cycles are applied for another 6 cycles for demonstration in this study. The corresponding system's state responses are summarized in FIG. 15 panels A-F where its non-periodicity is illustrated. This is due to the system's non-linear dynamics and the fact that the initial conditions are not periodic, as would be expected in an actual setting.

Moreover, the temperature profile within the tube is governed by the heat transfer dynamics from the temperature jacket through the wall and encrust and into the tube. While the tube temperature profiles (FIG. 15 panel A) are virtually identical for both even and odd cycles, none of the other responses, including solute concentration (FIG. 15 panel B), encrust thickness (FIG. 15 panel C), residence time (FIG. 15 panel D), $L_{43}$ (FIG. 15 panel E) and CV (FIG. 15 panel F), repeats from cycle-to-cycle. Thus, a set of feedback controllers are essential in assuring that despite these variations, the process is still controlled to desired setpoints.

Example 8: CSD and Encrust On-Off Feedback

Figure 16:
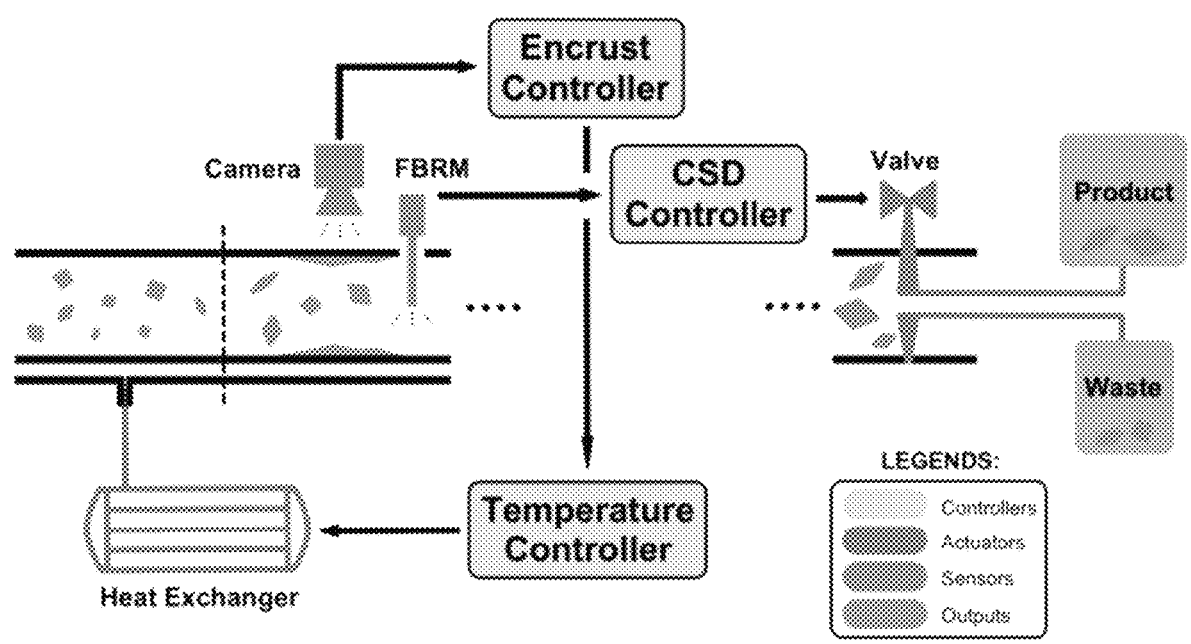
FIG. 16 is a schematic of an SF-AFC. The CSD controller reads input from the FBRM sensor and calculates the difference between the product quality set-point in terms of L43 or CV. The controller manipulates the output valve in order to ensure only the collection of in-spec output stream. Additionally, the on-off encrust feedback controller receives input from a gray-scale camera, which determines the presence of encrustation and manipulates, via the temperature controller, the duration and the magnitude of the heating cycle.
Figure 17:
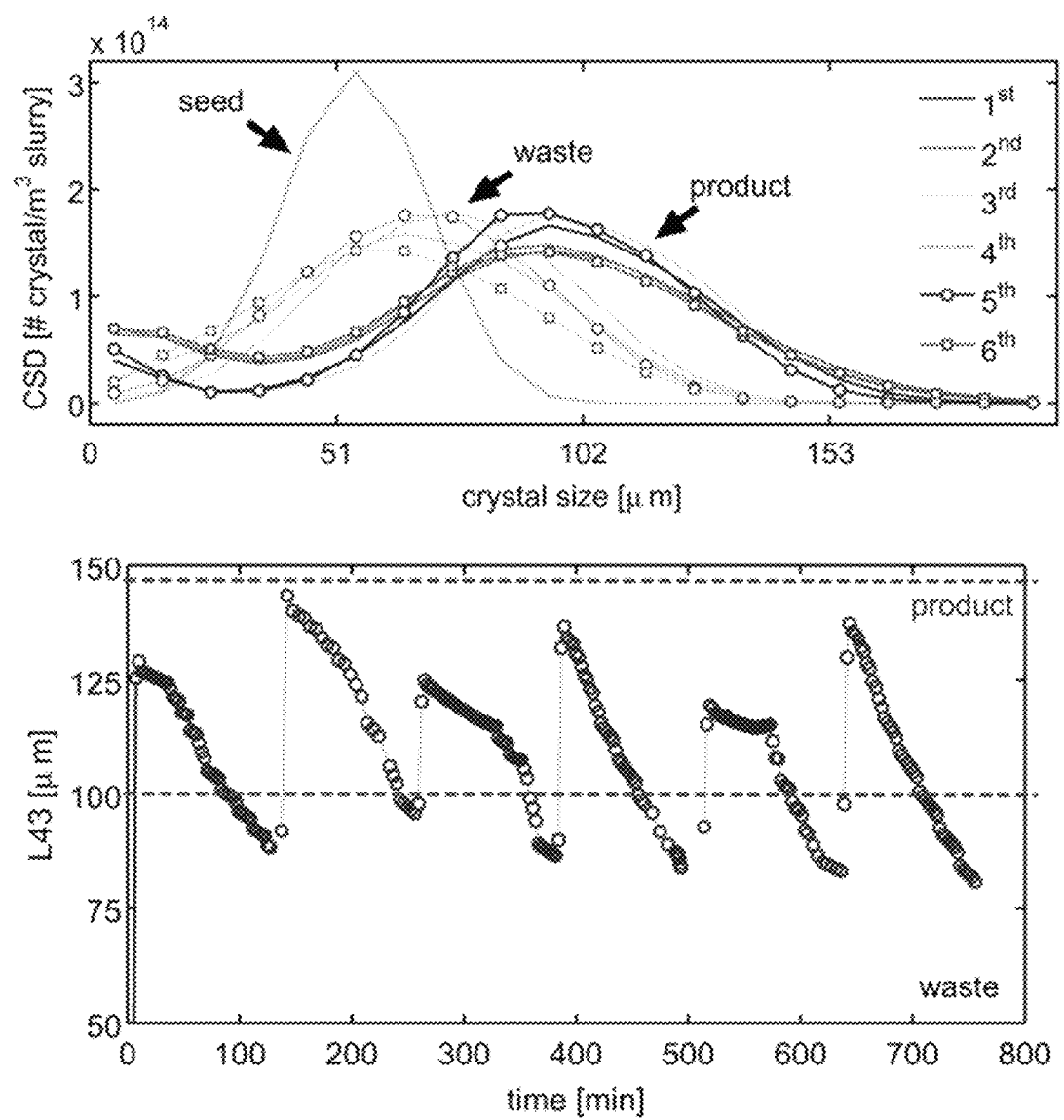
FIG. 17 is a set of graphs showing response of a PFC with an on-off CSD feedback sensor. (Top) Simulated product output (solid line) and waste (dashed line) with 100 µm cut-off as the set-point for the feedback controller. (Bottom) Response of the AFC implementation in terms of the L43 with the feedback sensor turned on between the dashed line. The product lot is indicated with the blue region while the waste with the orange region.
Figure 18:
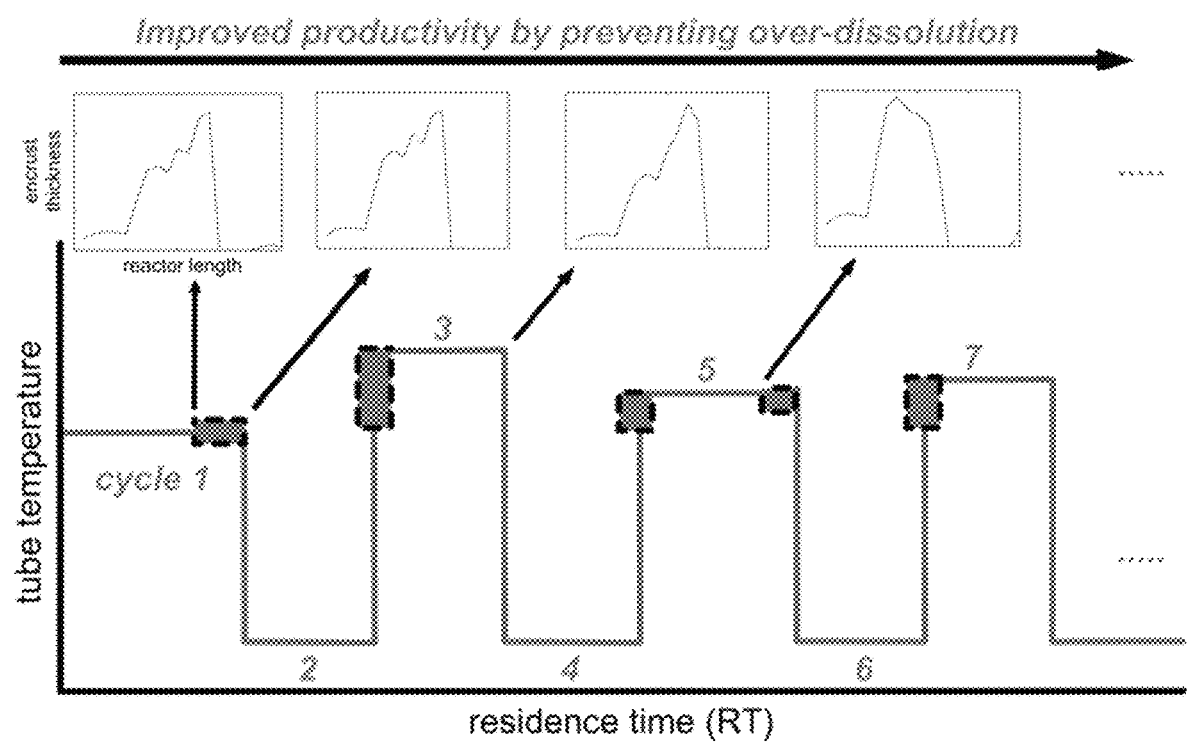
FIG. 18 shows action of the encrust feedback controller and its response in terms of the evolution of encrust thickness from cycle-to-cycle. The controller increases the duration of the heating (and, thus, cooling) in the first cycle as it recognizes the presence of encrust after the allotted cycle time. It then increases the heating temperature in the next odd-cycle by a preset constant and this case, it reduces the duration of the allotted time to prevent over-dissolution. The next odd-cycle uses a temperature profile that is the midpoint of the previous two heating temperatures. The controller then repeats this 3-step procedure.

The schematic of model-free AFC shown in FIG. 16 delineates the various components within the design, including the controllers, sensors, actuators and outputs, and the flow of data between them. The model-free AFC utilizes two types of on-off feedback sensors and controllers using a readily available CSD sensor (e.g. an FBRM or a PVM) and an encrust sensor (e.g. a grayscale camera) coupled with an algorithmic switch to the operation of the heat exchangers and valves (actuators) based on the sensor measurements. The CSD sensor determines the period of output stream collection for as long as the flow is within upper and lower bound specifications (FIG. 17) while the latter actively modifies the duration and magnitude of the heating action such that complete dissolution of the encrust occurs without crystal over-dissolution. Specifically, the CSD controller receives input from the FBRM sensor and detects the difference between the set-point and subsequently manipulates the valve which collects the output stream as either product or waste using a simple on-off switch. This switch is an algorithm written in a software which can interact with both the sensors and actuators (e.g. LabView). On the other hand, the encrust controller obtains input from a gray-scale camera, which determines the presence of encrustation. It communicates with the temperature controller of the heat exchanger to manipulate the duration and magnitude of the heating cycle at the beginning of the process. The mechanism of the encrust feedback controller is illustrated in FIG. 18.

The encrust controller works following a simple set of procedures: (i) it increases (decreases) the duration of the heating cycle if it detects that encrust is under-dissolved (completely dissolved prior to) in the allotted time in the first odd or even cycle, (ii) it increases (decreases) the temperature in the next iteration by a pre-specified magnitude should the heating cycle need be extended in the previous cycle. At this point, should the encrust be completely dissolved (under-dissolved) prior to the allotted time, the current cycle is cut short (prolonged) before the next cycle begins, (iii) Should complete encrust dissolution (under-dissolution) be observed, the temperature in the next cycle is reduced (increased) via midpoint calculation of the difference between the two previous temperature profiles, and (iv) the steps in (ii) and (iii) are repeated for odd and even cycle in any order depending on whether over- or under-dissolution is first observed such that a heating setting is set for which the cycle finishes in the allotted time with complete dissolution of the encrust and without over-dissolution of the crystal. An illustration of the encrust feedback implementation is shown in FIG. 18 (top) and its response, in terms of $L_{43}$ as compared with one without the feedback implemented is shown in FIG. 18 (bottom). In summary, while the CSD feedback controller guarantees product quality over the whole operation duration, the encrust counterpart prevents blockage and minimizes waste.

The comparison of model-free AFC implementations with and without feedback are compared. The results are summarized in Table 3.

TABLE 3

| Cases | $L_{43}$ (μm) | CV (—) | Yield (%) | Throughput (%) |
|---|---|---|---|---|
| Optimized PFC | 138 | 0.17 | 97 | 66 |
| Minimized Encrustation | 90 | 0.19 | 10 | 100 |
| Open-loop AFC | 103 | 0.22 | 42 | 100 |
| AFC with CSD feedback | 107 | 0.22 | 34 | 100 |
| AFC with CSD + encrust feedback | 109 | 0.22 | 35 | 100 |

While the optimized PFC without AFC produces the best product quality and the highest yield, it suffers from discontinuous operation. For throughput comparison across the different case studies, it is assumed that the cleaning process takes approximately one third (66% throughput) of the process duration when it reaches a 40% blockage. By contrast, encrustation may be minimized such that the PFC is operational for the whole duration of the intended process—100% throughput over 6 cycles—but with low product quality and yield. With open-loop AFC implementation, the process becomes continuous with expected product quality and reduced yield. As was discussed previously, this is due to the fact that only half of the PFC is utilized for cooling and generating crystals while the other half for heating and dissolving the encrust formed in the preceding cycle. When only CSD feedback is implemented, the crystal size increases at the same time as the yield decreases. With both the encrust and CSD feedback implemented the crystal size and yield is slightly improved due to prevention of over-dissolution, but, most importantly, without the risk of encrust build-up.

Example 9: Segment Length

Figure 19:
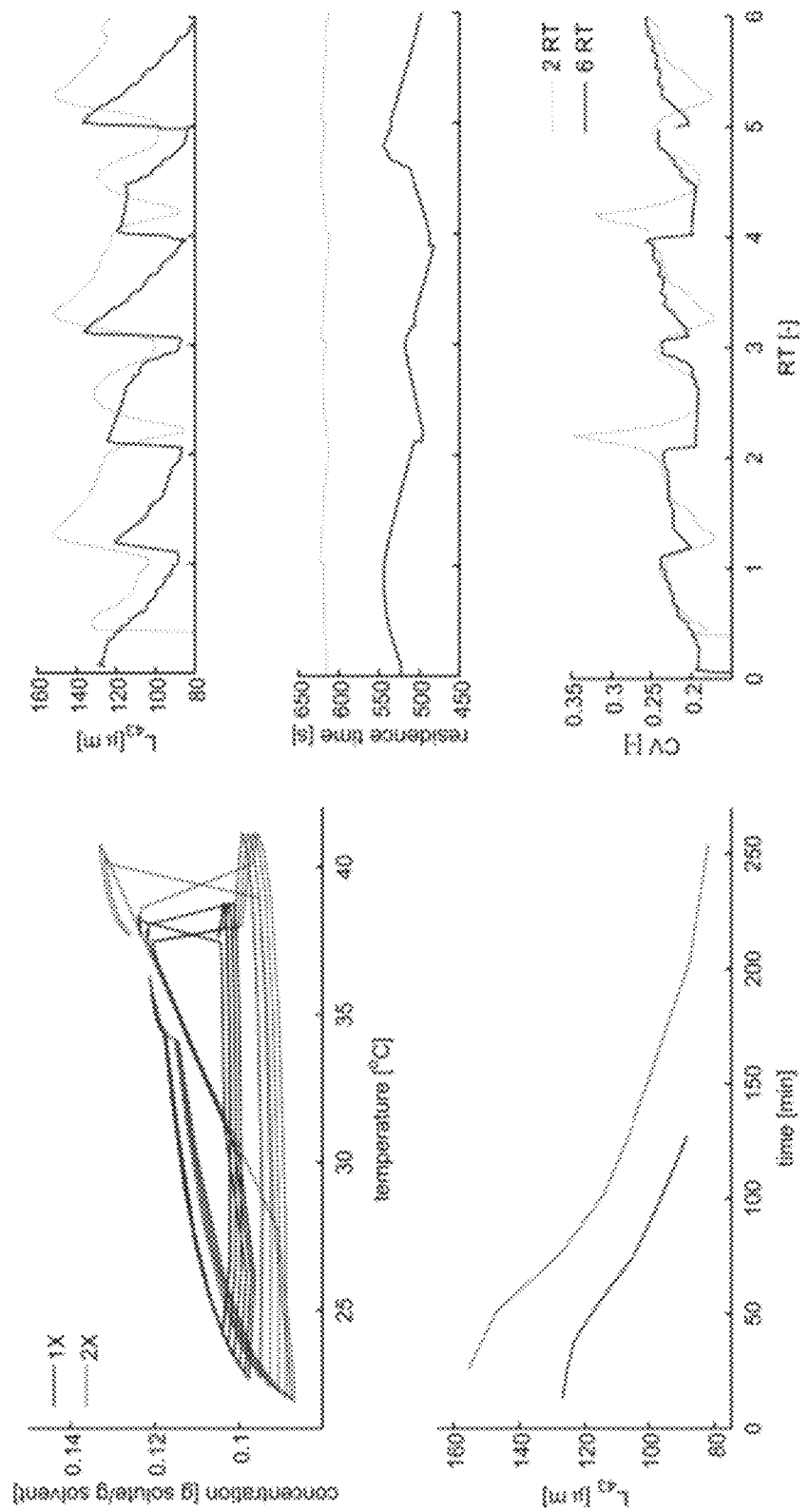
FIG. 19 is a set of graphs showing the effect of increase in segment size on the performance of AFC: sufficiently long segment length allows for complete heat transfer between the jacket and the tube temperature such that the supersaturation driving force is maximized during cooling (top). This not only translates to larger crystal yield, but also high throughput (bottom).
Figure 20A:
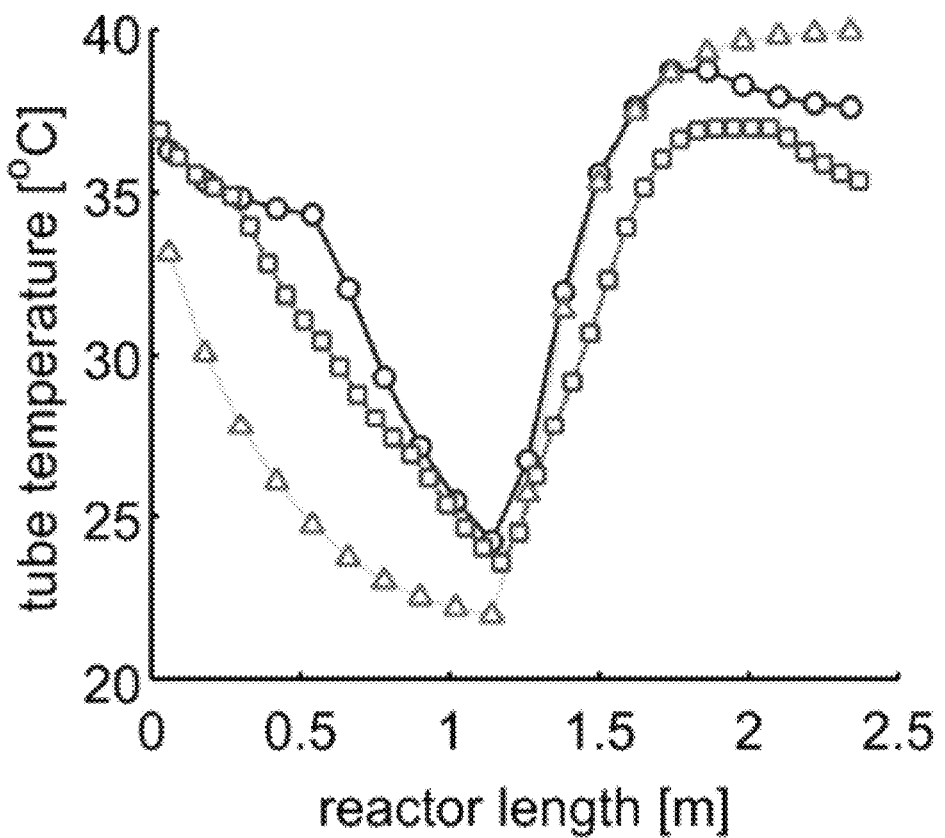
FIGS. 20A-D show the effect of PFC segmentation on AFC performance. Larger number of segmentations allow for a more flexible jacket temperature profile, which translates to improved control over the tube temperature and is reflected on the operating curves, encrust response, and L43 response.
Figure 20B:
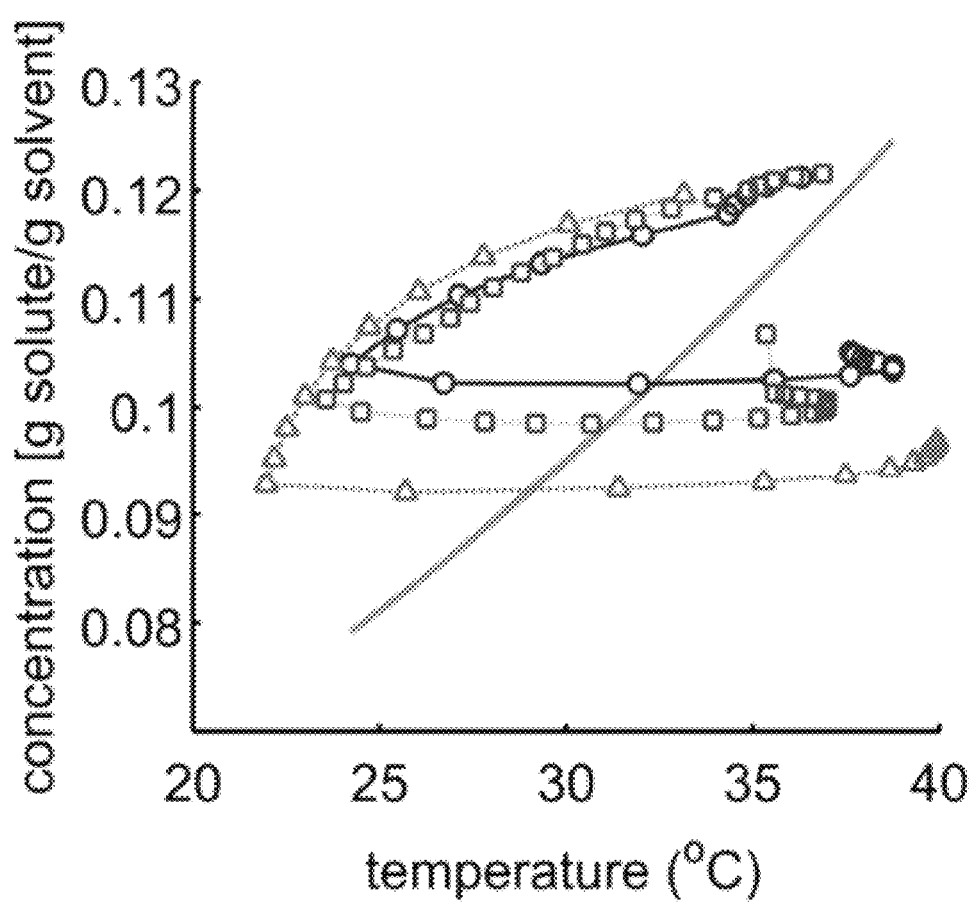
Figure 20C:
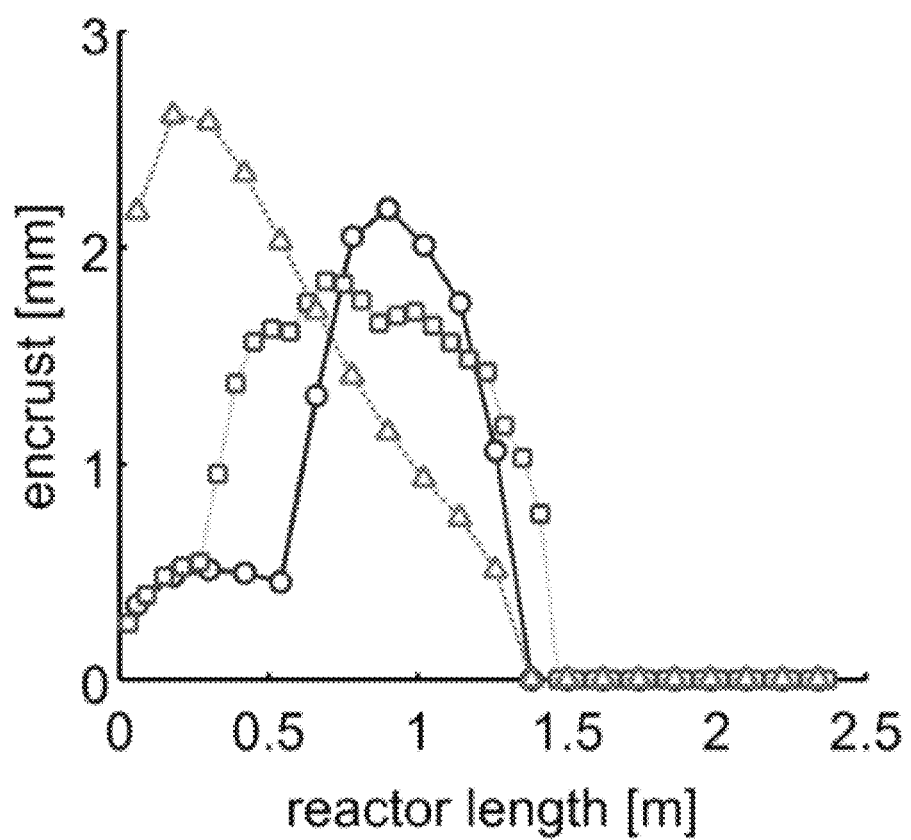
Figure 20D:
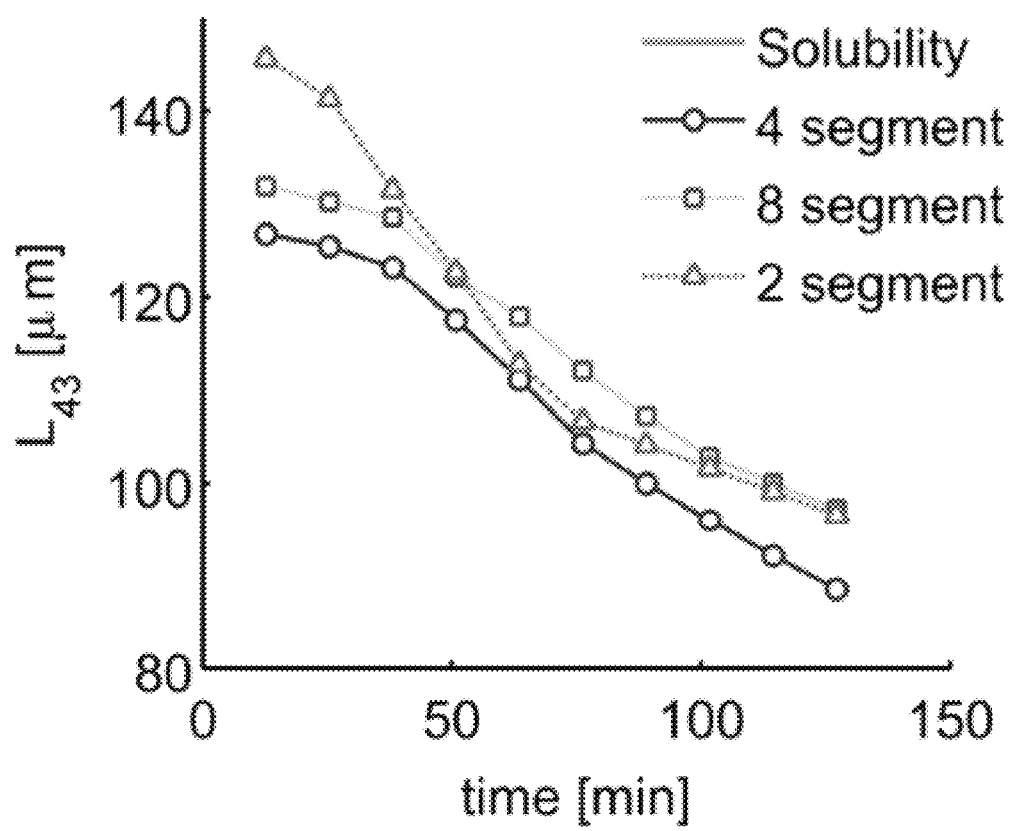

In the presence of encrustation, the PFC design may be further refined to improve the continuous operation utilizing the model-free AFC. Here, the effect of PFC segmentations, segment length and temperature cycling frequency are investigated. The results are summarized in FIG. 19. FIG. 19 illustrates that the longer the PFC is the larger is the residence time and, therefore, the crystal quality and yield. In turn, the upper and lower bounds on the crystal size may be tuned by modifications of the PFC segment length based on simulation and experiments. Specifically, while the residence time is directly proportional to the segment length, the crystal growth is not due to limitation in the heat transfer across the encrust. The yield of the process at the beginning is close to the theoretical yield and diminishes over time as the encrust builds. Nevertheless, sufficiently long segment length allows for complete heat transfer between the jacket and tube temperature such that the supersaturation driving force is maximized by ensuring that tube temperature reaches the lowest cooling temperature. This, however, means that the PFC is over-designed such that in the nominal case in which encrustation is not significant, the second half of the PFC would occupy an extra footprint and not harness any more crystal mass from the slurry. It is worthwhile to note that the longer segment length not only translates to higher crystal yield, but also larger throughput.

Example 10: Number of Segmentations

It is also demonstrated by simulation that larger number of temperature jackets per segment allow for more flexible control over the tube temperature (FIGS. 20A-D). For this study, the behavior of temperature segmentations are not studied in the optimal case, i.e. optimal control calculation was not performed for different number of segmentations. Instead, the temperature profile in each case is the approximation of the optimal control profile obtained for the 4 segment case. Specifically, for the 2-segment PFC the temperature profile is the lower and upper bound of the attainable temperature for cooling and heating, respectively, and for the 8-segment PFC, the 2 extra segments in each of the cooling and heating regions are the midpoint of the adjacent segments. The results are presented on the trajectory of the operating curves, encrust response and $L_{43}$ response. More segmentations lead to smoother temperature profile, which then translates to better control of growth and dissolution trajectories. While the 2 segment operates readily within the upper and lower bound of the heating and cooling profiles, it maximizes both crystal and encrust growth in the leading edge of the cooling segment. This leads to higher crystal yield but also blockage (~50%) such that the blockage constraint (~40%) is not met. On the other hand, the 8-segment counterpart produces a more refined form of the 4-segment temperature profile such that blockage is further reduced (~30%) via spreading of the encrust mass along the cooling segment and that the crystal mean size is improved due to better control of encrust dissolution, which leads to complete dissolution of the encrust but with weakened product dissolution.

Example 11: Cycling Frequency

The temperature cycling frequency is thus far based on the point at which 40% blockage of the flow area is reached. Given the assumed encrustation rate, this corresponds to ~12 RT in each cycle. However, this cycling frequency may be modified rather than predetermined based on a different criteria. As shown in FIGS. 20A-D, shorter heating and cooling cycles can lead to higher crystal quality and yield as the residence time of the operation is maintained at a high value prior to significant encrust formation. Here, the heating temperature has been reduced by a degree as this readily results in complete dissolution of the encrust during optimization in the first two cycles. While the rate of crystal dissolution is comparable to that of higher cycling frequency, there is less waste since the cooling segment allows for stronger driving force and, in turn, larger crystal output. It is essential to note that here we assume that the temperature switching in the heat exchangers between heating and cooling is instantaneous and in turn represents the ideal scenario which does not account for the reduction in yield and throughput when delay in the change of temperature control set-points is present.

Example 12: Effect of Crystal and Encrust Kinetics

Figure 21:
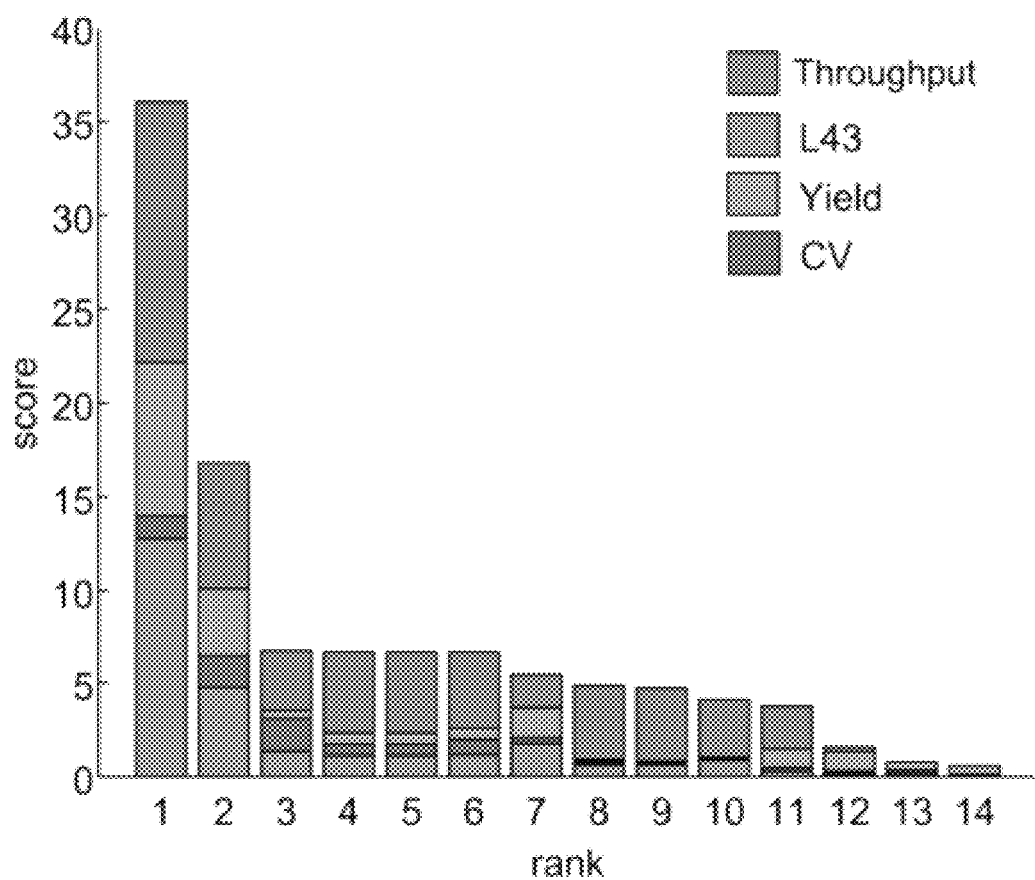
FIG. 21 shows full factorial design space analysis of model-free AFC. The results are obtained by varying the crystal and encrust growth kinetic parameters, namely kg, kE, kd, and α, by ±30%. The score associated with each response categories, such as L43, CV, yield, and waste, are calculated as the % change relative to the nominal counterpart with the stacked bar graphs representing the sum of % changes.

The effectiveness of the model-free AFC scheme depends on its robustness to the variations or uncertainties in the crystal and encrust kinetics (e.g. in the presence of other factors such as impurities). Should the rate of encrust formation be larger than expected, the calculated temperature profile may not be sufficient to dissolve the encrust in the allotted time. This subsequently leads to encrust accumulation over multiple cycles and eventually blockage. Additionally, if the encrust dissolves quicker than expected the crystal would dissolve sooner and the yield would lessen. Similarly, should the crystal growth be smaller (larger) than predicted, the crystal output would also be lower (higher) as a result. Hence, a robust model-free AFC design should consistently perform as expected in spite of these deviations such that the product quality and yield are always within specifications. In this example, the sensitivity of the feedback control method is approximated using a full-factorial design space analysis and by relatively aggressively varying the crystal and encrust kinetics by +/−30%. The analysis is performed only for one cycle with the results expressed in terms of the % change of the $L_{43}$, CV, yield and waste, relative to the nominal values. Note that here the yield is calculated as in Example 7, which is the difference between theoretical solubility of the crystal at the lowest temperature during the cooling segment and the tube concentration. By contrast, the waste is calculated as the mass of output stream designated as waste. The overall yield would therefore be the multiplication of the yield and waste. The scores in each category are then added up for each kinetic parameter in order to summarize its effect on the control performance. The results are summarized in Table 4 and FIG. 21 and they show that the crystal growth kinetics are twice as influential (with a score of 36) as the encrust counterpart when evaluated within the range of the design.

TABLE 4

| Ranked Parameters | L43 | CV | yield | productivity |
| --- | --- | --- | --- | --- |
| $k_g$ | 12.731 | −1.265 | 8.151 | 13.906 |
| $k_R$ | −4.658 | 1.759 | 3.704 | −6.682 |
| $k_d$ | −1.202 | 1.884 | −0.454 | −3.139 |
| $k_R \times \alpha \times k_G \times k_D$ | −1.148 | 0.602 | 0.594 | −4.247 |
| $k_R \times \alpha$ | −1.184 | 0.529 | 0.612 | −4.247 |
| $k_R \times k_D$ | −1.176 | 0.807 | 0.601 | −3.963 |
| $k_R \times k_G$ | −1.797 | 0.244 | −1.648 | 1.719 |
| $\alpha \times k_D$ | −0.665 | 0.126 | 0.104 | −3.920 |
| $\alpha \times k_G$ | −0.673 | 0.027 | 0.096 | −3.920 |
| $k_G \times k_D$ | −0.839 | 0.053 | 0.106 | −3.069 |
| $k_R \times k_G \times k_D$ | 0.258 | −0.189 | −1.029 | −2.244 |
| $k_R \times \alpha \times k_G$ | 0127 | −0.089 | −1.014 | 0.313 |
| $\alpha$ | 0.122 | −0.168 | −0.455 | −0.014 |

While there are notable interactions between different parameters, they are relatively small. Specifically, the kinetics have the biggest effect on the amount of waste, followed by $L_{43}$ and yield. None of the factors appear to have a significant effect on the CV which is consistent with what is usually observed in a seeded crystallization process. In particular, there is not a point within the design space which suggests that model-free AFC operation may fail to produce the expected control performance, albeit at the expense of lower yield and larger waste. Nevertheless, yield and throughput may be significantly improved and tuned according to process specifications and uncertainties by the design of the PFC. This observation, thus, suggests that a combination of feedback controllers (QbC) and PFC design (QbD) would realize the potential of the model-free AFC implementation.

Example 13: System Implementation with Feedback Control

Three unseeded PFC experiments were performed to study the effect of encrustation and heating and cooling cycle in a plug-flow crystallization using a 1.1-L continuous oscillatory baffled reactor (COBR) (Nitech Solutions, Model: DN-15 Lite). In the first experiment, glycine (Sigma Aldrich, CAS: 103-90-2) was chosen as the crystallization system to demonstrate a PFC operation without significant fouling, and thus serve as a negative control case. On the other hand, paracetamol (Sigma Aldrich, CAS: 56-40-6) was used in the second experiment for implementation of AFC as it has a significantly higher encrustation rate suitable for evaluation of the effect of encrustation—the positive control case—as well as implementation of heating and cooling cycle. The output is collected on a 80 mL surge tank, in which an FBRM probe (Mettler Toledo, Model: G400) monitors the chord length distribution (CLD) at every residence time interval and after which the collected solution is recycled into the feed. A 10-30 mL glycine samples were also collected at each RT for image analysis using a microscope and processed using ImageJ. The COBR settings for all the three experiments are as follows: the bulk flow rate is 35 mL/min corresponding to a 31 min mean residence time (RT) and the amplitude and frequency of the imposed oscillatory flow is 20 mm and 2 Hz, respectively. The temperature of the flow within the COBR is monitored using three thermocouples each placed in the beginning of the 2nd and the 4th segment and at the end of the 7th segment (Table 5).

TABLE 5

| Design Parameter | $L_{43}$ (μm) | CV (—) | yield (%) |
|---|---|---|---|
| Switching Period | | | |
| 2 RT | 123 | 0.22 | 43 |
| 6 RT | 108 | 0.22 | 34 |
| Segmentation | | | |
| 2 | 114 | 0.22 | 62 |
| 4 | 106 | 0.21 | 42 |
| 8 | 112 | 0.20 | 49 |
| Segment Length | | | |
| 2X | 111 | 0.24 | 59 |

Negative Control Experiment Using Glycine

Figure 22A:
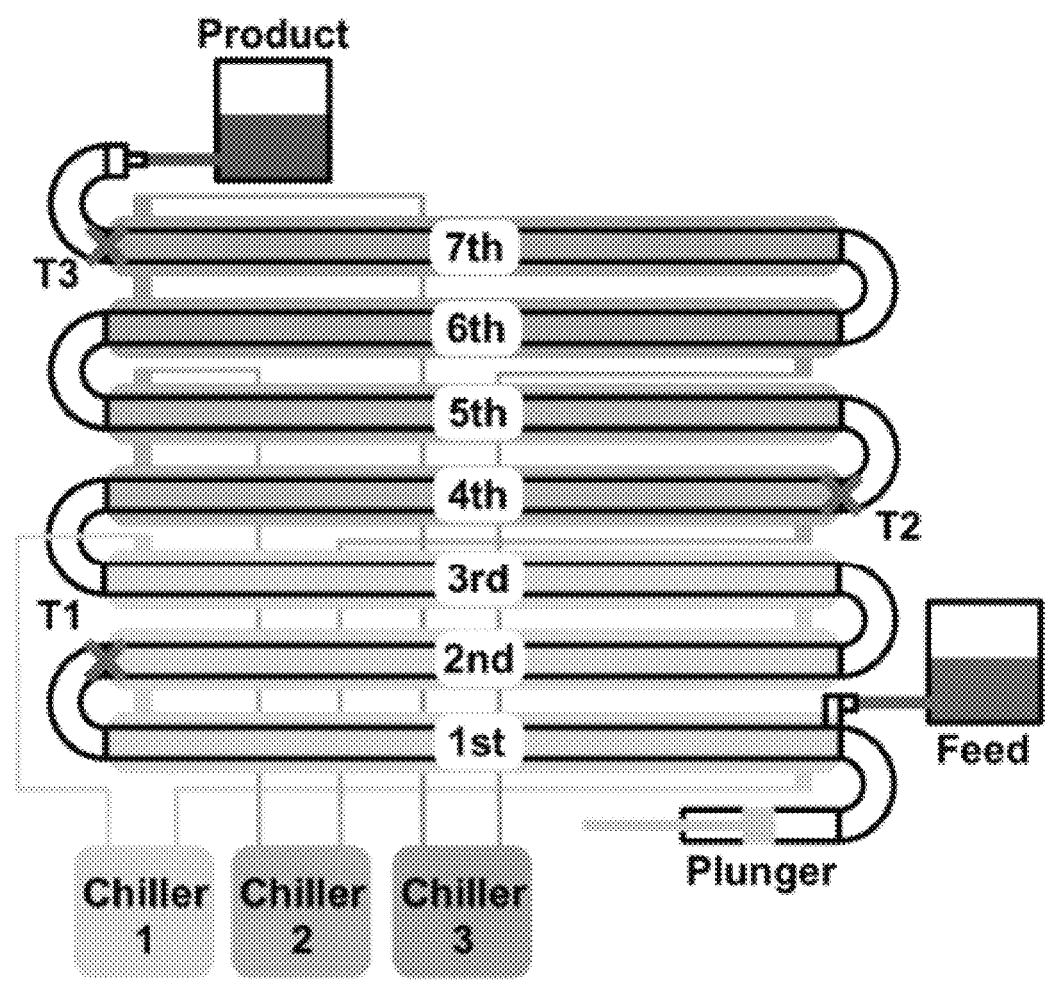
FIGS. 22A-B show COBC set-up for glycine and paracetamol crystallization experiments.
Figure 22B:
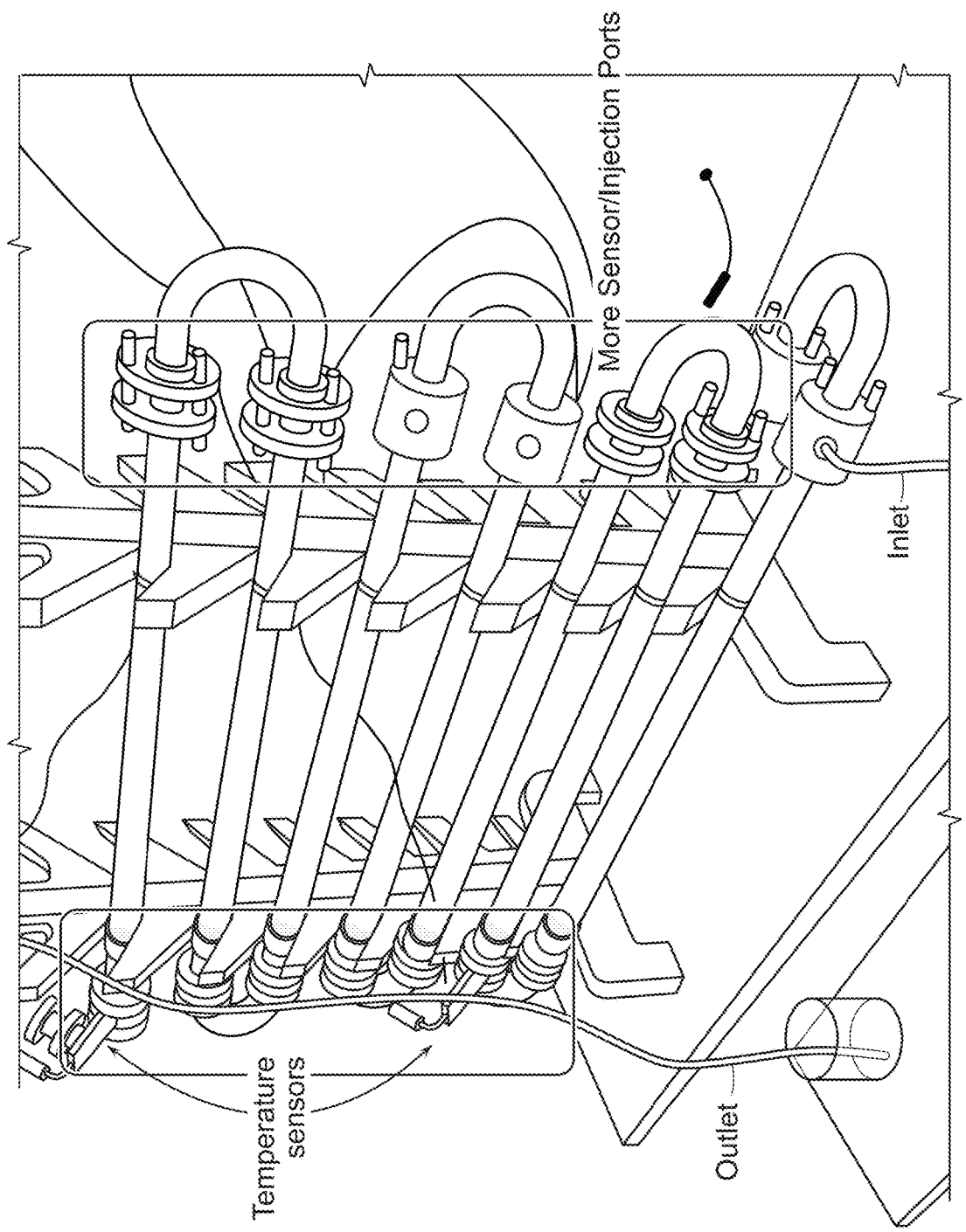

The experimental set-up and schematics for the glycine experiment are shown in FIGS. 22A-B. Here, the COBR is divided into three sections each of which is connected to a chiller. The first section is the first three segments of the COBC while the second and third sections are the 4th and 5th, and the 6th and 7th segment, respectively. The feed solution is glycine dissolved in deionized water (DIW) at a solubility of 0.4 g/g $H_2O$ corresponding to a saturation temperature of 55° C. The feed temperature is maintained at 65+/−5° C. to ensure undersaturation in the inlet transfer lines so as to prevent clogging due to crystal formation and deposits. The system is initially equilibrated with DIW at the different temperature set-points and the water is circulated through the COBC at a high linear and oscillatory flow until all apparent bubbles had been flushed out. The experiment commenced by setting the flow set-point and replacing the water inlet with the supersaturated feed solution. When the system reaches steady state, the outlet is placed into the inlet and the system operates in recycle mode.

AFC Experiment Using Paracetamol

The paracetamol COBR set-up for investigating the effect of encrust formation and heating and cooling cycle is analogous to that of glycine experiment except that it involves different section and chiller configurations and different temperature set-points. In this study, the feed paracetamol are prepared in DIW at a saturation temperature of 50° C. and is slowly cooled at temperature set-points of 47° C., 37° C., and 22° C. in the first, second, and third section of the COBR, respectively. The slow cooling experiments were performed for 4 RT and, as the encrust accumulated, the heating and cooling cycling experiment commenced. Note that due to encrustation, the system does not reach steady state and the product is recycled at the beginning or the third RT. It is assumed that while the concentration of the recycled feed changes due to encrustation, it is not sufficient to significantly reduce the crystallization and encrustation kinetics. The cycling experiments were performed for two cycles each for two RT. The first cycle implements the temperature control set-points of 50° C., 50° C., and 22° C. and the second 50° C., 22° C. and 38° C. corresponding to the three sections of the COBR.

Results and Discussion

Figure 23A:
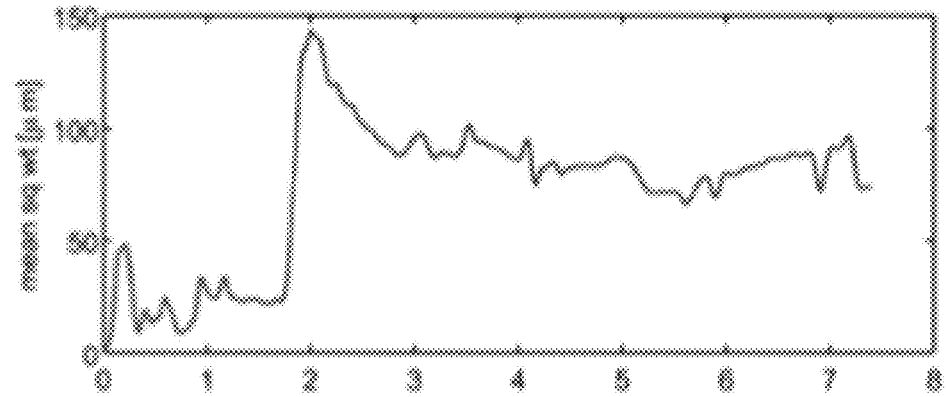
FIGS. 23A-D show a summary of glycine crystallization. The results include the dynamics of L43, normalized mean square weight of the CLD, temperature at the end of each segment, and the temperature profile across the reactor.
Figure 23B:
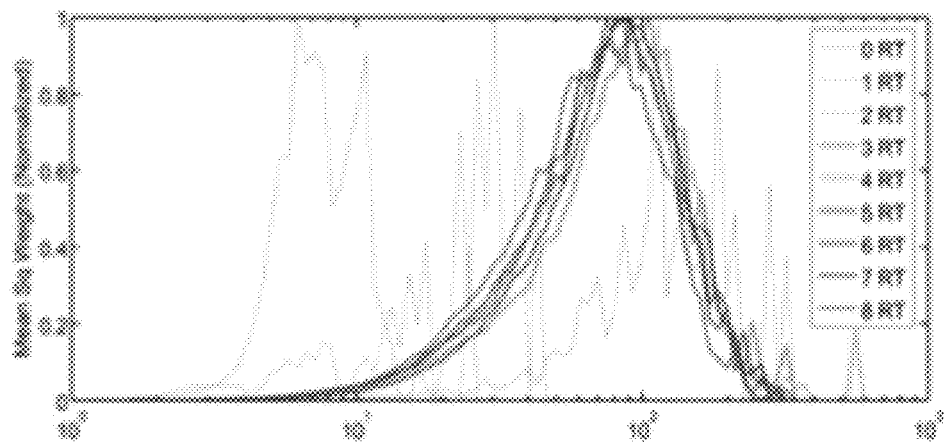
Figure 23C:
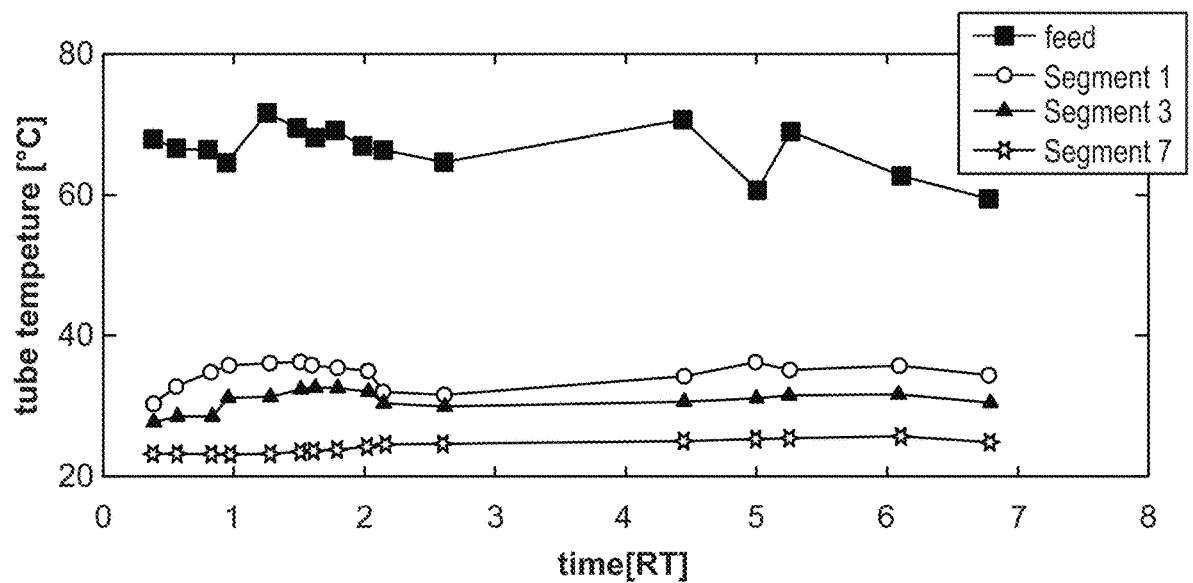
Figure 23D:
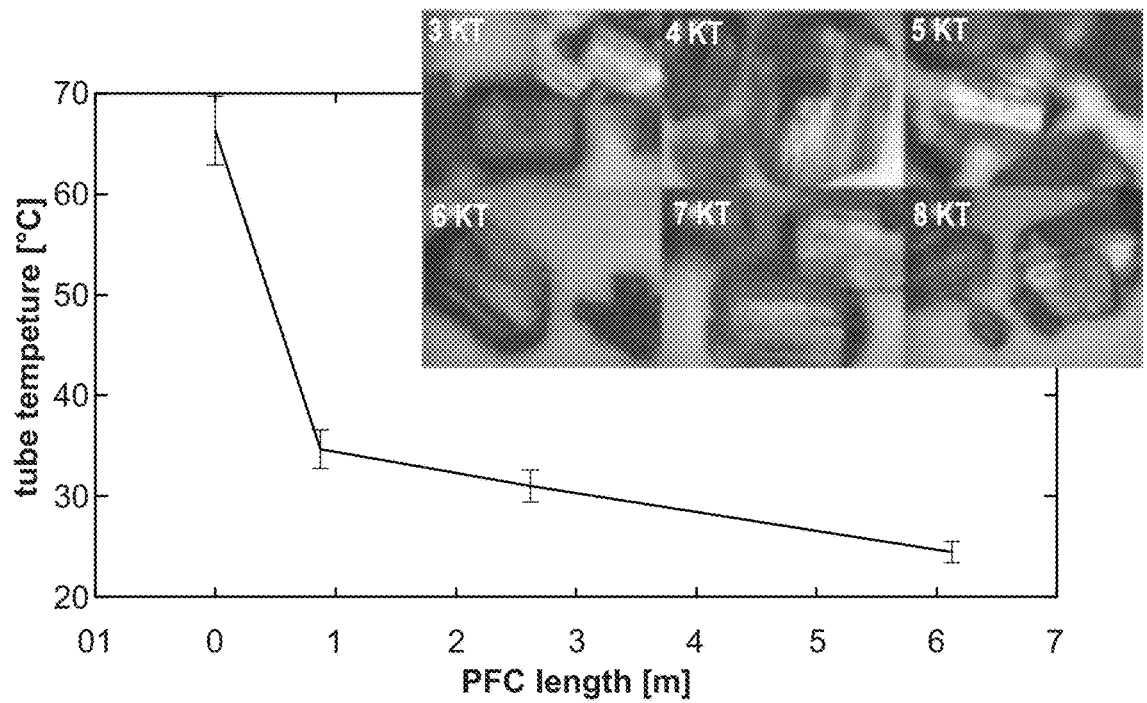
Figure 24A:
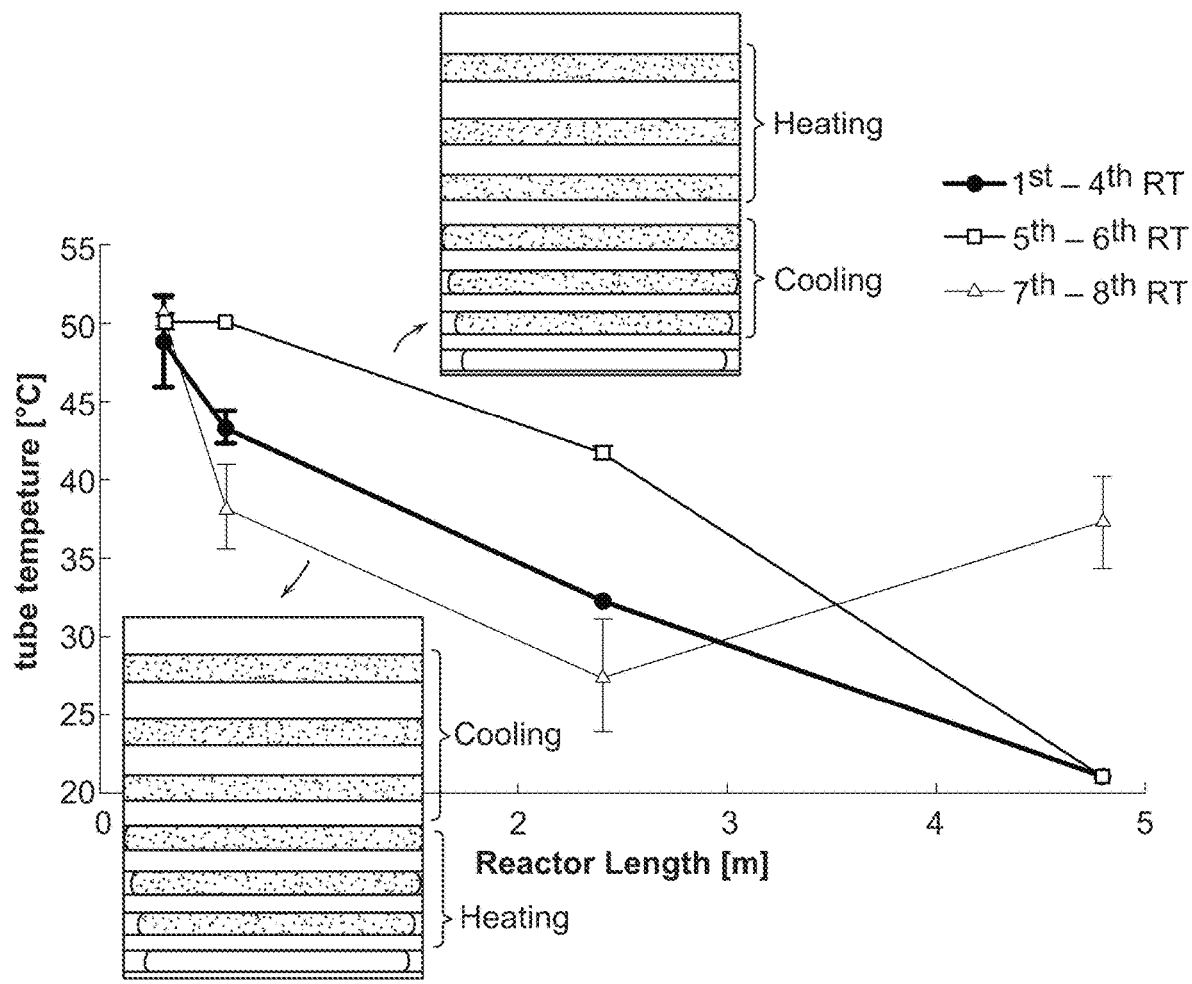
FIGS. 24A-D show COBR heating and cooling cycle. The heating and cooling segments periodically alternate upon dissolution of the encrust.
Figure 24B:
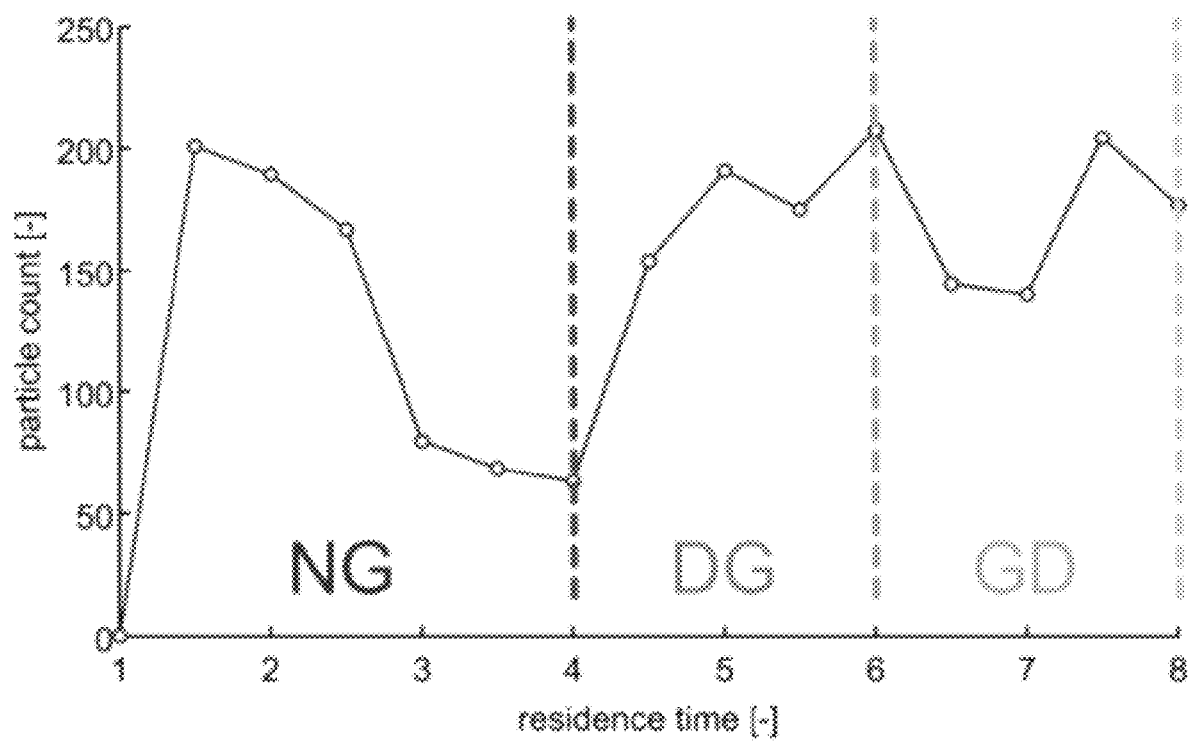
Figure 24C:
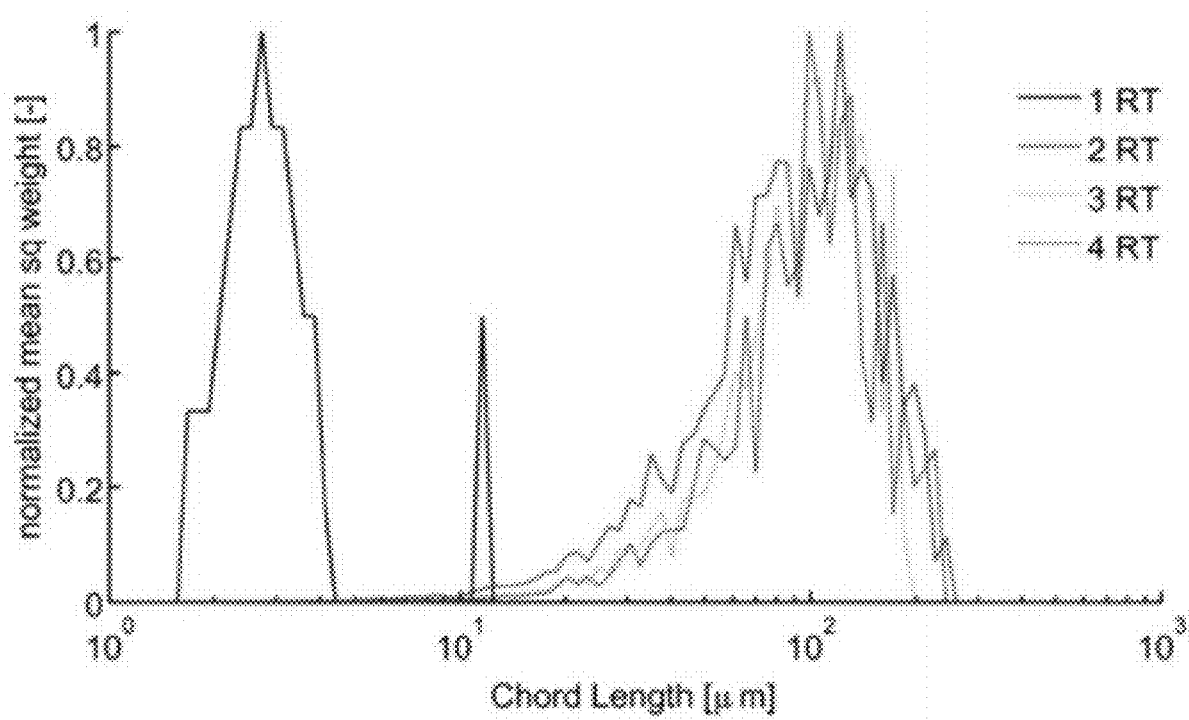
Figure 24D:
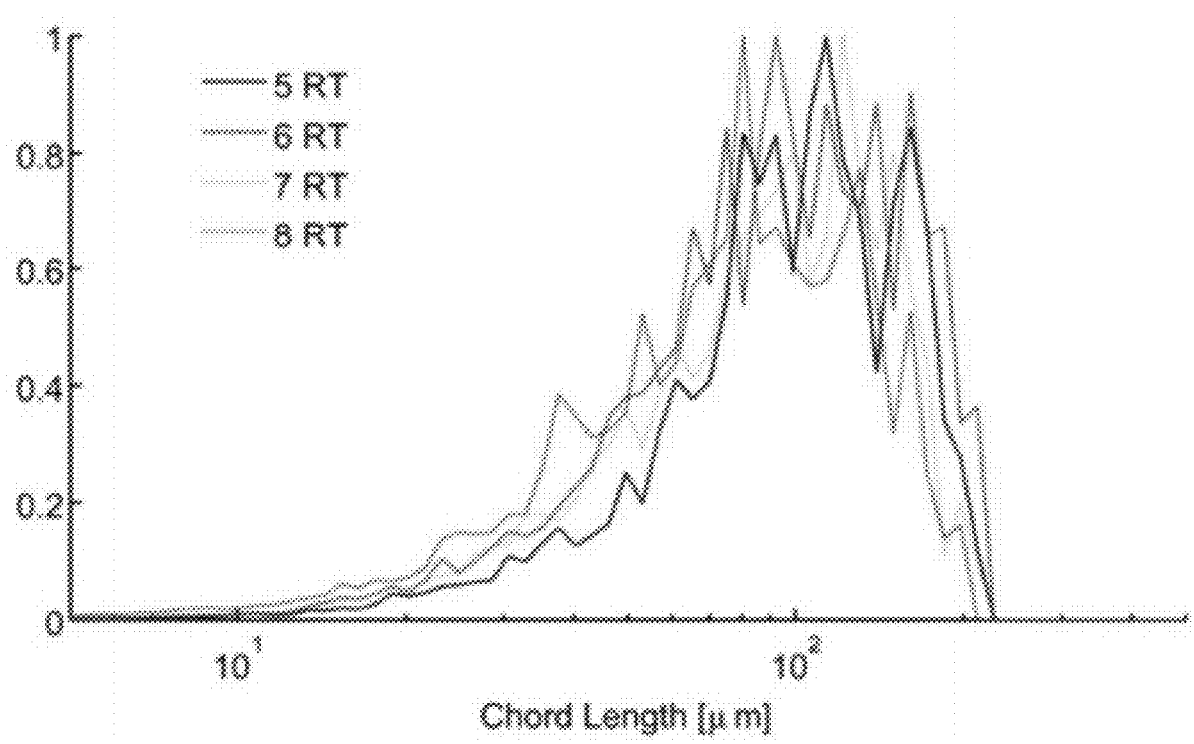

The experiment using glycine represents the crystallization process in which significant encrustation does not take place and the CSD reaches steady state by the third RT. It suggests that it takes 1 RT to completely replace water out of the system and another RT for the crystallization dynamics to stabilize. FIGS. 23A-D show the operation of glycine crystallization. FIG. 23A corresponds to crystal count while FIG. 23B the CLD. The latter is accompanied by several light microscope images of glycine crystals sampled at various RTs. FIG. 23C shows the temperature readings along the crystallizer, which are relatively constant as controlled, and FIG. 23D shows the temperature profile across the device over the whole duration of the experiment. A similar experiment but with slow cooling profile was performed for paracetamol crystallization. Here, the process never reaches steady state as the encrust continues to build in the second segment and the crystal count continue to decrease (FIGS. 24A-D). The heating and cooling cycle proceeded right after the slow cooling stage at the 5th RT. Given that the second segment was fouled, in the first cycle the second segment implements heating and the third segment cooling. This was performed at the following temperature set-points in the 50° C., 50° C. and ° C. in the 1st, 2nd and 3rd segment, respectively and for 2 RT. In the proceeding cycle, the heating and cooling segment alternated and the temperature set-points are 50° C., 27° C., and 39° C., respectively. The results of the experiments are summarized in FIGS. 24A-D. The particle count (and $L_{43}$) oscillates over the two cycles and were not periodic as predicted. The CLD, however, does not fluctuate as may have been expected in the case of fouling. There appears to be an increase in the level of aggregates which should be accounted for in the future modeling of AFC. Specifically, the experiment showed how the fouled segments are cycled and during which both the CSD data and encrust picture may be used as input to the on-off feedback controllers for a fully automated solution of fouling control.

CONCLUSION

A PFC may be designed to operate according to a set of crystal product criteria only for encrustation to prevent the process from ever reaching steady state and maintaining the desired set-points. Building upon an open-loop AFC scheme described in the earlier Examples, the later Examples, provide embodiments of a model-free AFC, which utilizes readily available PAT tools and on-off feedback controller to maintain continuous operations. Specifically, optimal cooling and heating profiles are calculated for the first two cycles and implemented indefinitely in the process such that overall crystal growth occurs along the reactor while encrust formation and dissolution are periodically cycled between the cooling and heating segments. This control execution is coupled with an on-off CSD and encrust feedback controllers, which guarantee control performance and product quality.

The CSD feedback controller ensures collection of only the material with desired product properties while the encrust counterpart enforce complete encrust dissolution without crystal over-dissolution. Sensitivity studies using full-factorial design space analysis were performed to investigate the robustness of the feedback control scheme and show that the method would continue to work. The performance of the PFC may be further enhanced via the PFC designs in terms of the PFC segmentations, segment length, as well as the switching period or cycling frequency. It is shown that a sufficiently long PFC is helpful in ensuring that crystallization completes during cooling in order to maximize yield, and that a generally higher number of temperature jackets allow for more precise control of the growth and dissolution dynamics such that yield may be improved without overdesigning the PFC. Additionally, the cycling frequency affects the rate at which the amount of encrust is counter-balanced with the crystal yield. The faster the switching times are the less is the blockage and the longer is the residence time during cooling, leading to overall larger crystal growth. It is important to note that the switch between cooling and heating is assumed to take place instantaneously and that a delay would subsequently reduce the process yield and throughput.

Experiments were performed to compare the performance of a PFC with and without significant encrustation and with heating and cooling cycle applied. Using a COBR to represent an ideal PFC, glycine is used to demonstrate the former while paracetamol the latter. The heating and cooling cycle serves as a proof-of-concept for the model-free AFC, in which the switch between heating and cooling cycles are performed manually. The results show that when no fouling takes place the PFC process reached steady state in 3 RT in terms of particle count and CLD. When encrustation takes place the process did not reach steady state in terms of particle count, while the CLD remained constant. Nevertheless, the number of aggregates appeared to have increased as encrust built, which may be responsible in maintaining the CLD while the CSD may have actually decreased. As the heating and cooling cycle was implemented, the encrust dissolved and the number of particles increased. The count then decreased as a new layer of encrust built in the cooling section and the cycle repeats with the cooling section experiencing heating and vice versa. In general, both seeded PFC simulation and unseeded PFC experiment served as a proof-of-concepts for implementing a model-free AFC in both seeded and unseeded operations during which the CLD data and encrust picture may be used as input to the on-off feedback controllers for a fully automated solution of fouling control.

What is claimed is:

1. A system with anti-fouling control, the system comprising:
   a plug flow crystallizer comprising a channel;
   one or more heating/cooling elements, each operably associated with a different segment of the channel; and
   a controller operably coupled to the one or more heating/cooling elements and configured to implement, via an algorithm, a temperature profile within the channel of the plug flow crystallizer that grows crystals in a plug of fluid that flows through a first segment of the channel and dissolves encrust in a second segment of the channel while having minimal impact on crystal growth in the plug of fluid in the second segment of the channel, wherein the algorithm accounts for existence of a boundary layer between the encrust and the channel such that there exists a temperature gradient between the encrust and the channel so that during cooling, a film temperature is lower than that of the channel, while during heating it is higher such that supersaturation in a growth phase and under saturation in a dissolution phase are stronger for encrust dynamics relative to that of crystallization.

2. The system according to claim 1, wherein the first segment of the channel has a same length as the second segment of the channel.

3. The system according to claim 2, wherein the temperature profile in the first segment is configured for cooling the one or more plugs of fluid that flow in the first segment to thereby cause crystal growth.

4. The system according to claim 3, wherein the temperature profile in the second segment is configured for heating the one or more plugs of fluid that flow in the second segment to thereby cause encrust dissolution while having minimal impact on crystal growth in the one or more plugs of fluid in the second segment of the channel.

5. The system according to claim 1, wherein the controller is further configured to calculate the temperature profile based on encrust kinetics and crystal growth kinetics for a particular reaction.

6. The system according to claim 1, further comprising one or more sensors operably coupled to the system.

7. The system according to claim 6, wherein a first sensor determines a period of output stream collection for as long as flow is within a predetermined product quality range.

8. The system according to claim 7, wherein the first sensor operably communicates to the controller, which manipulates a valve based on data received from the first sensor, to control collection of the one or more plugs of fluid.

9. The system according to claim 6, wherein a second sensor monitors encrust within the channel.

10. The system according to claim 9, wherein the second sensor operably communicates to the controller, which manipulates the temperature within the channel, via the one or more heating/cooling elements, based on data received from the second sensor.

11. A method for controlling fouling within a channel of a plug flow crystallizer, the method comprising:
   flowing one or more plugs of fluid through a channel of a plug flow crystallizer; and
   implementing, via an algorithm running on a controller operably coupled to the plug flow crystallizer, a temperature profile within the channel of the plug flow crystallizer that grows crystals in the one or more plugs of fluid that are flowing through a first segment of the channel and dissolves encrust in a second segment of the channel while having minimal impact on crystal growth in the plugs of fluid in the second segment of the channel, wherein the algorithm accounts for existence of a boundary layer between the encrust and the channel such that there exists a temperature gradient between the encrust and the channel so that during cooling, a film temperature is lower than that of the channel, while during heating it is higher such that supersaturation in a growth phase and under saturation in a dissolution phase are stronger for encrust dynamics relative to that of crystallization.

12. The method according to claim 11, wherein the first segment of the channel has a same length as the second segment of the channel.

13. The method according to claim 12, wherein the temperature profile in the first segment is configured for cooling the one or more plugs of fluid that flow in the first segment to thereby cause crystal growth.

14. The method according to claim 13, wherein the temperature profile in the second segment is configured for heating the one or more plugs of fluid that flow in the second segment to thereby cause encrust dissolution while having minimal impact on crystal growth in the one or more plugs of fluid in the second segment of the channel.

15. The method according to claim 11, wherein the method further comprises calculating, via the controller, the temperature profile based on heat transfer, encrust kinetics and crystal growth kinetics for a particular crystallization reaction.

16. The method according to claim 11, further comprising monitoring conditions within the channel via one or more sensors operably coupled to the controller.

17. The method according to claim 16, wherein a first sensor determines a period of output stream collection for as long as flow is within a predetermined product quality range.

18. The method according to claim 17, wherein the first sensor operably communicates to the controller, which manipulates a valve based on data received from the first sensor, to control collection of the one or more plugs of fluid.

19. The method according to claim 16, wherein a second sensor monitors encrust within the channel.

20. The method according to claim 19, wherein the second sensor operably communicates to the controller, which manipulates the temperature within the channel, via one or more heating/cooling elements, based on data received from the second sensor.

* * * * *